(12) United States Patent
Harris et al.

(10) Patent No.: US 9,727,692 B2
(45) Date of Patent: *Aug. 8, 2017

(54) METHODS AND SYSTEMS FOR GENOMIC ANALYSIS

(71) Applicant: Personalis, Inc., Menlo Park, CA (US)

(72) Inventors: Jason Harris, San Carlos, CA (US);
Mark R. Pratt, Menlo Park, CA (US);
John West, Cupertino, CA (US);
Richard Chen, Burlingame, CA (US);
Ming Li, Fremont, CA (US)

(73) Assignee: Personalis, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/871,020

(22) Filed: Sep. 30, 2015

(65) Prior Publication Data

US 2016/0019341 A1    Jan. 21, 2016

Related U.S. Application Data

(63) Continuation of application No. 14/474,034, filed on Aug. 29, 2014, now Pat. No. 9,183,496.

(60) Provisional application No. 61/872,611, filed on Aug. 30, 2013.

(51) Int. Cl.
*G06F 19/22* (2011.01)
*G06F 15/00* (2006.01)
*G06F 19/18* (2011.01)
*G06N 3/12* (2006.01)

(52) U.S. Cl.
CPC ............... *G06F 19/22* (2013.01); *G06F 19/18* (2013.01); *G06N 3/126* (2013.01)

(58) Field of Classification Search
None
See application file for complete search history.

(56) References Cited

U.S. PATENT DOCUMENTS

| | | | |
|---|---|---|---|
| 4,988,617 A | 1/1991 | Landegren et al. | |
| 5,242,794 A | 9/1993 | Whiteley et al. | |
| 5,494,810 A | 2/1996 | Barany et al. | |
| 5,641,658 A | 6/1997 | Adams et al. | |
| 5,928,907 A | 7/1999 | Woudenberg et al. | |
| 6,015,674 A | 1/2000 | Woudenberg et al. | |
| 6,582,938 B1 | 6/2003 | Su et al. | |
| 6,818,395 B1 | 11/2004 | Quake et al. | |
| 7,169,560 B2 | 1/2007 | Lapidus et al. | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,280,922 B2 | 10/2007 | Mei et al. | |
| 7,282,337 B1 | 10/2007 | Harris | |
| 7,300,788 B2 | 11/2007 | Matsuzaki et al. | |
| 7,323,305 B2 | 1/2008 | Leamon et al. | |
| 7,335,762 B2 | 2/2008 | Rothberg et al. | |
| 7,361,488 B2 | 4/2008 | Fan et al. | |
| 9,183,496 B2 * | 11/2015 | Harris | G06F 19/18 |
| 2002/0164629 A1 | 11/2002 | Quake et al. | |
| 2009/0026082 A1 | 1/2009 | Rothberg et al. | |
| 2009/0127589 A1 | 5/2009 | Rothberg et al. | |
| 2009/0191565 A1 | 7/2009 | Lapidus et al. | |
| 2010/0035252 A1 | 2/2010 | Rothberg et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0004413 A1 | 1/2011 | Carnevali et al. | |
| 2011/0009296 A1 | 1/2011 | Kain et al. | |
| 2013/0124100 A1 | 5/2013 | Drmanac et al. | |
| 2013/0178389 A1 | 7/2013 | Lapidus et al. | |
| 2015/0066824 A1 | 3/2015 | Harris et al. | |

FOREIGN PATENT DOCUMENTS

| | | |
|---|---|---|
| WO | WO 00/18957 A1 | 4/2000 |
| WO | WO 2011/091046 A1 | 7/2011 |
| WO | WO 2012/142611 A2 | 10/2012 |

OTHER PUBLICATIONS

Pasanuic et al. Extremely low-coverage sequencing and imputation increases power for genome-wide association studies. Nature Genetics vol. 44, pp. 631-635 (2012).*

Adessi, et al. Solid phase DNA amplification: characterisation of primer attachment and amplification mechanisms. Nucleic Acids Res. Oct. 15, 2000;28(20):E87.

Asan, et al. Comprehensive comparison of three commercial human whole-exome capture platforms. Genome Biol. Sep. 28, 2011;12(9):R95. doi: 10.1186/gb-2011-12-9-r95.

Bainbridge, et al. Whole exome capture in solution with 3 Gbp of data. Genome Biol. 2010;11(6):R62. doi: 10.1186/gb-2010-11-6-r62. Epub Jun. 17, 2010.

Boulesteix, et al. Evaluating microarray-based classifiers: an overview. Cancer Inform. 2008;6:77-97. Epub Feb. 29, 2008.

(Continued)

*Primary Examiner* — John S Brusca
(74) *Attorney, Agent, or Firm* — Wilson Sonsini Goodrich & Rosati

(57) ABSTRACT

A computer-implemented method for processing and/or analyzing nucleic acid sequencing data comprises receiving a first data input and a second data input. The first data input comprises untargeted sequencing data generated from a first nucleic acid sample obtained from a subject. The second data input comprises target-specific sequencing data generated from a second nucleic acid sample obtained from the subject. Next, with the aid of a computer processor, the first data input and the second data input are combined to produce a combined data set. Next, an output derived from the combined data set is generated. The output is indicative of the presence or absence of one or more polymorphisms of the first nucleic acid sample and/or the second nucleic acid sample.

36 Claims, 6 Drawing Sheets

(56) References Cited

OTHER PUBLICATIONS

Braslavsky, et al. Sequence information can be obtained from single DNA molecules. Proc Natl Acad Sci U S A. Apr. 1, 2003;100(7):3960-4. Epub Mar. 21, 2003.
Choi, et al. Genetic diagnosis by whole exome capture and massively parallel DNA sequencing. Proc Natl Acad Sci U S A. Nov. 10, 2009;106(45):19096-101. doi: 10.1073/pnas.0910672106. Epub Oct. 27, 2009.
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.
Fahy, et al. Self-sustained sequence replication (3SR): an isothermal transcription-based amplification system alternative to PCR. PCR Methods Appl. Aug. 1991;1(1):25-33.
Fishel, et al. Meta-analysis of gene expression data: a predictor-based approach. Bioinformatics. Jul. 1, 2007;23(13):1599-606. Epub Apr. 26, 2007.
Guo, et al. Exome sequencing generates high quality data in non-target regions. BMC Genomics. May 20, 2012;13:194. doi: 10.1186/1471-2164-13-194.
Illumina Technical Note: Informatics. Sequencing coverage information methods for human whole-genome sequencing. A overview of Illumina coverage calculation methods using BaseSpace or third party analysis tools. 2014. 2 pages.
Illumina Technical Note: Sequencing. Estimating sequencing coverage. Before starting a sequencing experiment, you should know the depth of sequencing you want to achieve. This technical note helps you estimate that coverage. 2014. 2 pages.
International search report and written opinion dated Dec. 2, 2014 for PCT Application No. US2014/053295.
Kiialainen, et al. Performance of microarray and liquid based capture methods for target enrichment for massively parallel sequencing and SNP discovery. PLoS One. Feb. 9, 2011;6(2):e16486. doi: 10.1371/journal.pone.0016486.
Leamon, et al. A massively parallel PicoTiterPlate based platform for discrete picoliter-scale polymerase chain reactions. Electrophoresis. Nov. 2003;24(21):3769-77.
Lizardi, et al. Mutation detection and single-molecule counting using isothermal rolling-circle amplification. Nat Genet. Jul. 1998;19(3):225-32.
Margulies, et al. Genome sequencing in microfabricated high-density picolitre reactors. Nature. Sep. 15, 2005;437(7057):376-80. Epub Jul. 31, 2005.
Marsh. Pyrosequencing applications. Methods Mol Biol. 2007;373:15-24.
Mitra, et al. In situ localized amplification and contact replication of many individual DNA molecules. Nucleic Acids Res. Dec. 15, 1999;27(24):e34.
Moudrianakis, et al. Base sequence determination in nucleic acids with the electron microscope. 3. Chemistry and microscope of guanine-labeled DNA. Proc Natl Acad Sci U S A. Mar. 1965;53:564-71.
Ng, et al. Targeted capture and massively parallel sequencing of 12 human exomes. Nature. Sep. 10, 2009;461(7261):272-6. doi: 10.1038/nature08250. Epub Aug. 16, 2009.
Notice of allowance dated Aug. 14, 2015 for U.S. Appl. No. 14/474,034.
Ochman, et al. Genetic applications of an inverse polymerase chain reaction. Genetics. Nov. 1988;120(3):621-3.

Office action dated May 14, 2015 for U.S. Appl. No. 14/474,034.
Office action dated Dec. 2, 2014 for U.S. Appl. No. 14/474,034.
Ozsolak, et al. Direct RNA sequencing. Nature. Oct. 8, 2009;461(7265):814-8. doi: 10.1038/nature08390. Epub Sep. 23, 2009.
Pierce, et al. Linear-after-the-exponential polymerase chain reaction and allied technologies. Real-time detection strategies for rapid, reliable diagnosis from single cells. Methods Mol Med. 2007;132:65-85.
Robinson, et al. Strategies for exome and genome sequence data analysis in disease gene discovery projects. Clinical Genetics, vol. 80, No. 2, pp. 127-132 (2011) See the whole document.
Rosenfeld, et al. Novel multi-nucleotide polymorphisms in the human genome characterized by whole genome and exome sequencing. Nucleic Acids Research, Article No. gkq408, pp. 1-10 (2010) See abstract; and pp. 8-9.
Ross, et al. Characterizing and measuring bias in sequence data. Genome Biology, vol. 14, No. 5, Article No. R51, pp. 1-20 (e-pub, May 29, 2013) See the whole document.
Saeys, et al. A review of feature selection techniques in bioinformatics. Bioinformatics. Oct. 1, 2007;23(19):2507-17. Epub Aug. 24, 2007.
Saiki, et al. Analysis of enzymatically amplified beta-globin and HLA-DQ alpha DNA with allele-specific oligonucleotide probes. Nature. Nov. 13-19, 1986;324(6093):163-6.
Shigemizu, et al. A practical method to detect SNVs and indels from whole genome and exome sequencing data. Scientific Reports, vol. 3, No. 2161, pp. 1-6 (e-pub, Jul. 8, 2013) See abstract; pp. 2, 5; and tables 1-2.
Smyth. Limma: linear models for microarray data. In: Bioinformatics and Computational Biology Solutions using R and Bioconductor. R. Gentleman, V. Carey, S. Dudoit, R. Irizarry, W. Huber (eds.), Springer, New York, pp. 397-420.
Soni, et al. Progress toward ultrafast DNA sequencing using solid-state nanopores. Clin Chem. Nov. 2007;53(11):1996-2001. Epub Sep. 21, 2007.
Stemmer, et al. Single-step assembly of a gene and entire plasmid from large numbers of oligodeoxyribonucleotides. Gene. Oct. 16, 1995;164(1):49-53.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Velculescu, et al. Characterization of the yeast transcriptome. Cell. Jan. 24, 1997;88(2):243-51.
Velculescu, et al. Serial analysis of gene expression. Science. Oct. 20, 1995;270(5235):484-7.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995;23(21):4407-14.
Walker, et al. Strand displacement amplification—an isothermal, in vitro DNA amplification technique. Nucleic Acids Res. Apr. 11, 1992;20(7):1691-6.
Westin, et al. Anchored multiplex amplification on a microelectronic chip array. Nat Biotechnol. Feb. 2000;18(2):199-204.
Pasaniuc, et al. Extremely low-coverage sequencing and imputation increases power for genome-wide association studies. Nat Genet. May 20, 2012;44(6):631-5. doi: 10.1038/ng.2283. With Supplementary Information.
European Search Report dated Feb. 28, 2017 for EP Application No. 14840405.6.
Warren, R.L. et al., Targeted assembly of short sequence reads. PLOS One, 6(5): May 5, 2011; p. e19816, XP055347747, DOI:10.1371/journal.pone.0019816.

\* cited by examiner

METHODS AND SYSTEMS FOR GENOMIC ANALYSIS

CROSS-REFERENCE

This application is the continuation application of U.S. patent application No. 14/474,034, filed Aug. 29, 2014, now U.S. Pat. No. 9,183,496, which application claims priority to U.S. Provisional Patent Application Ser. No. 61/872,611, filed Aug. 30, 2013, each of which is entirely incorporated herein by reference.

BACKGROUND

Exome sequencing, while cost effective, may have the shortcoming of only probing 1-2% of the genome. For many clinical applications of genetic analysis, sensitivity to large copy number variations and micro-deletions can be achieved using competitive hybridization array or whole genome sequencing. However, the former has little or no sensitivity to novel or rare single nucleotide variations and/or other small variants while the latter is substantially more expensive than exome sequencing but adds little sensitivity for clinically interpretable variants.

SUMMARY

The present disclosure provides computer systems and methods that can analyze a sample of a subject to, for example, identify the presence or absence of one or more polymorphisms in the sample. Methods provided herein advantageously employ untargeted (e.g., whole genome) sequencing and target-specific sequencing to generate an output that indicates the presence or absence of one or more polymorphisms in the sample of the subject.

The present disclosure provides an assay that can generate a first set of data containing at least some or all variants (e.g., single nucleotide variations or insertion deletion polymorphism) from the exome of a nucleic sample of a subject, in addition to at least another assay that can generate a second set of data that contains at least some or all variants (e.g., structural variants or copy number variations) from the whole genome of the nucleic sample of the subject. The first set of data and second set of data can be combined into a combined output. In some cases, variants from the first set of data and variants from the second set of data are combined into the combined output. This can provide a rapid and economical approach to identifying the presence or absence of one or more polymorphisms in the nucleic sample of the subject. Such assaying can be accomplished using nucleic acid sequencing or nucleic acid amplification (e.g., polymerase chain reaction (PCR)) with two different sample preparation methods that are directed to identifying variants in the exome and variants in the genome. For example, variants in the exome can be identified using target-specific sequencing (e.g., using target specific primers), and variants in the whole genome can be identified using untargeted sequencing.

An aspect of the present disclosure provides a computer-implemented method, comprising: (a) receiving a first data input, wherein the first data input comprises untargeted sequencing data generated from a first nucleic acid sample of a subject; (b) receiving a second data input, wherein the second data input comprises target-specific sequencing data generated from a second nucleic acid sample of the subject; (c) combining, with the aid of a computer processor, the first data input and the second data input to produce a combined data set; and (d) generating, with the aid of a computer processor, an output derived from the combined data set, wherein the output is indicative of the presence or absence of one or more polymorphisms of the first nucleic acid sample and/or the second nucleic acid sample.

In some embodiments, the first nucleic acid sample and the second nucleic acid sample are the same sample. Alternatively, the first nucleic acid sample and the second nucleic acid sample are different samples.

In an embodiment, combining the first data input and the second data input comprises removing redundant sequences. In another embodiment, the combined data set contains no redundant sequence information. In an embodiment, the output comprises a first alignment, wherein the first alignment is generated by mapping the first data input onto a first reference sequence. In another embodiment, the output further comprises a second alignment, wherein the second alignment is generated by mapping the second data input onto a second reference sequence. In another embodiment, the output comprises a uniform alignment, wherein the uniform alignment is generated by combining the first alignment with the second alignment. In another embodiment, combining the first alignment with the second alignment comprises removing redundant sequences. In another embodiment, the output comprises a uniform alignment, wherein the uniform alignment is generated by mapping the combined data set onto a reference sequence. In another embodiment, the uniform alignment contains no redundant sequence information.

In an embodiment, some or all of the reference sequences can include sequences that are from a human subject.

In an embodiment, the target-specific sequencing data is based on targeted sequencing of exomes, specific genes, genomic regions, or a combination thereof. In another embodiment, the target-specific sequencing data is generated from the use of one or more non-random primers. In another embodiment, the non-random primers are chemically synthesized. In another embodiment, the non-random primers comprise primers targeting one or more genes, exons, untranslated regions, or a combination thereof. In another embodiment, a target specific primer can be a non-random primer. For example, a primer targeting one or more exons can be a non-random primer. In another embodiment, the non-random primers have sequences that are designed to be complementary to known genomic regions. In another embodiment, the genomic regions comprise one or more polymorphisms, sets of genes, sets of regulatory elements, micro-deletions, homopolymers, simple tandem repeats, regions of high GC content, regions of low GC content, paralogous regions, or a combination thereof. In another embodiment, the one or more polymorphisms comprise one or more single nucleotide variations, copy number variations, insertions, deletions, structural variant junctions, variable length tandem repeats, or a combination thereof. In another embodiment, the untargeted sequencing data is generated from the use of one or more random primers. In another embodiment, the random primers are chemically synthesized. In another embodiment, the random primers have sequences that are not designed to be complementary to known genomic regions. In another embodiment, the random primers comprise random hexamer primers. In another embodiment, the hexamer primers comprise oligonucleotide sequences of 6 bases which are synthesized entirely randomly. In another embodiment, the untargeted sequencing data comprises between about 0.5 to about 5 gigabases. In another embodiment, the untargeted sequencing data comprises at least about 10 megabases. In another embodiment, the untargeted sequencing data comprises at least about 300 megabases. In another embodiment, the untargeted sequencing data comprises less than about 100 gigabases. In another embodiment, the untargeted sequencing data comprises less than about 5 gigabases. In another embodiment, the analysis of the first data input comprises assigning data into genomic bins of between about 100 to about 1,000,000 basepairs. In another embodiment, the analysis of the first data input comprises assigning data into genomic bins of at least about 1 kilobasepairs. In another embodiment, the analysis of the first data input comprises assigning data into genomic bins of less than about 100 megabasepairs. In another embodiment, the analysis of the first data input comprises assigning data into genomic bins of 50 kilobasepairs. In another embodiment, the analysis of the first data input comprises assigning data into genomic bins of 1 megabasepairs. In another embodiment, the untargeted sequencing data is whole genome sequencing data, off-target data arising from a targeted assay, or a combination thereof. In another embodiment, the whole genome sequencing data comprises single reads. In another embodiment, the whole genome sequencing data comprises paired-end reads. In another embodiment, the whole genome sequencing data comprises mate-pair reads. In another embodiment, the paired-end reads have insert-sizes of larger than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 30.0, 40.0, 50.0, 60.0, 70.0, 80.0, 90.0, or 100.0 kilobasepairs. In another embodiment, the mate-pair reads have insert-sizes of larger than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 30.0, 40.0, 50.0, 60.0, 70.0, 80.0, 90.0, or 100.0 kilobasepairs. In another embodiment, the untargeted sequencing data is obtained at a single nucleotide variations detection sensitivity that is less than or equal to about 80%. In another embodiment, the untargeted sequencing data is obtained at a single nucleotide variations detection sensitivity that is at least about 5%, 10%, 20%, 30%, 40%, 50%, 60%, 70%, 75%, 80%, 85%, 90%, 95%, or 99%. In another embodiment, the untargeted sequencing data is obtained at a single nucleotide variations detection sensitivity that is from about 5% to 50%.

In another embodiment, the first data input and the second data input are combined to produce a combined data set. In another embodiment, an output is generated from the combined data set. In another embodiment, the generation of the output comprises assigning data from the combined data set into genomic bins of between about 100 to about 1,000,000 basepairs. In another embodiment, the generation of the output comprises assigning data from the combined data set into genomic bins of at least about 100, 200, 300, 400, 500, 600, 700, 800, or 900 basepairs. In another embodiment, the generation of the output comprises assigning data from the combined data set into genomic bins of at least about 1, 2, 3, 4, 5, 6, 7, 8, 9, 10, 20, 30, 40, 50, 60, 70, 80, 90, 100, 200, 300, 400, 500, 600, 700, 800, or 900 kilobasepairs. For example, the generation of the output comprises assigning data from the combined data set into genomic bins of at least about 1 kilobasepairs. In another embodiment, the generation of the output comprises assigning data from the combined data set into genomic bins of at least about 1, 2, 3, 4, 5, 6, 7, 8, 9, 10, 20, 30, 40, 50, 60, 70, 80, 90, 100, 200, 300, 400, 500, 600, 700, 800, 900 or 1000 megabasepairs. In another embodiment, the generation of the output comprises assigning data from the combined data set into genomic bins of less than about 100, 200, 300, 400, 500, 600, 700, 800, or 900 basepairs. In another embodiment, the generation of the output comprises assigning data from the combined data set into genomic bins of less than about 1, 2, 3, 4, 5, 6, 7, 8, 9, 10, 20, 30, 40, 50, 60, 70, 80, 90, 100, 200, 300, 400, 500, 600, 700, 800, or 900 kilobasepairs. In another embodiment, the generation of the output comprises assigning data from the combined data set into genomic bins of less than about 1, 2, 3, 4, 5, 6, 7, 8, 9, 10, 20, 30, 40, 50, 60, 70, 80, 90, 100, 200, 300, 400, 500, 600, 700, 800, 900 or 1000 megabasepairs. For example, the generation of the output comprises assigning data from the combined data set into genomic bins of less than about 100 mega basepairs. In another embodiment, the generation of the output comprises assigning data from the combined data set into genomic bins of about 1, 2, 3, 4, 5, 6, 7, 8, 9, 10, 20, 30, 40, 50, 60, 70, 80, 90, 100, 200, 300, 400, 500, 600, 700, 800, 900 or 1000 kilobasepairs. For example, the generation of the output comprises assigning data from the combined data set into genomic bins of 50 kilobasepairs. In another embodiment, the generation of the output comprises assigning data from the combined data set into genomic bins of less than about 1, 2, 3, 4, 5, 6, 7, 8, 9, 10, 20, 30, 40, 50, 60, 70, 80, 90, 100, 200, 300, 400, 500, 600, 700, 800, 900 or 1000 megabasepairs. For example, the generation of the output comprises assigning data from the combined data set into genomic bins of 1 mega basepairs. In another embodiment, the output is based on data from one or more databases or data sources. In another embodiment, the first and/or second reference sequence comprises data from one or more databases or data sources. In another embodiment, the first reference sequence and the second reference sequence are the same sequence. In another embodiment, the first reference sequence and the second reference sequence are different sequences. In another embodiment, the one or more databases or data sources are selected from the group consisting of medical records, clinical notes, genomic databases, biomedical databases, clinical databases, scientific databases, disease databases, variant databases and biomarker databases. In another embodiment, the one or more databases or data sources comprise proprietary databases. In another embodiment, the proprietary databases are selected from the group consisting of a disease database, variant database and pharmacogenomics database. In another embodiment, the one or more databases or data sources comprise publicly-available databases. In another embodiment, the publicly-available databases are selected from the group consisting of Orphanet, Human Phenotype Ontology, Online Mendelian Inheritance in Man, Model Organism Gene Knock-Out databases, Kegg Disease Database, and dbSNP. In another embodiment, the one or more polymorphisms are selected from the group consisting of copy number variations, single nucleotide variations, structural variants, micro-deletions, polymorphisms, insertions and deletions. In another embodiment, the output is generated with the aid of one or more machine-executed algorithms. In another embodiment, the output is generated with the aid of one or more statistical models. In another embodiment, the one or more statistical models comprise a Markov model. In another embodiment, the Markov model is a Hidden Markov Model. In another embodiment, the Hidden Markov Model is given an internal state, wherein the internal state is set according to an overall copy number of a chromosome in the first or second nucleic acid sample. In another embodiment, the Hidden Markov Model is used to filter the output by examination of measured insert-sizes of reads near a detected feature's breakpoint(s). In another embodiment, the output further comprises detection of one or more haplotypes. In another embodiment, the target-specific sequencing data is obtained at a single nucleotide variations sensitivity that is greater than or equal to about 50%, 60%, 70%, 75%, 80%, 85%, 90%, 95%, or 99%. In another embodiment, the output of the combined data set is displayed on a graphical user interface of an electronic display coupled to the computer. In another embodiment, the output is displayed in numeric and/or graphical form. In another embodiment, the output is an electronic report. In another embodiment, the first nucleic acid sample and the second nucleic acid sample are the same sample. In another embodiment, the output has coverage of at least about 50%, 60%, 70%, 75%, 80%, 85%, 90%, 95%, or 99% of the whole genome of the subject. In another embodiment, the output has coverage of the whole genome of the subject.

In some embodiments, the target-specific sequencing data comprises a specific portion and a non-specific portion, and wherein at least a portion of the untargeted sequencing data is the non-specific portion of the target-specific sequencing data. In an embodiment, the untargeted sequencing data is the non-specific portion of the target-specific sequencing data. In another embodiment, the targeted-specific sequencing data is whole exome sequencing data. In another embodiment, the specific portion is exonic portion of the whole exome sequencing data and the non-specific portion is non-exonic portion of the whole exome sequencing data.

In some embodiments, each of the first data input and the second data input comprises variant data, and the combining comprises combining the variant data from the first data input and the second data input into the combined data set. In an embodiment, the first data input comprises copy number and/or structural variant data, and the second data input comprises single nucleotide variations (SNV) and/or insertion deletion polymorphism (indel) data. In another embodiment, the method further comprises performing untargeted sequencing on the first nucleic acid sample to generate the first data input. In another embodiment, the method further comprises performing target-specific sequencing on the second nucleic acid sample to generate the second data input.

In another aspect of the present disclosure, a system for genomic sequencing comprises: (a) one or more memory locations (e.g., flash memory, hard disk) comprising a first data input and second data input, wherein the first data input comprises untargeted sequencing data and the second data input comprises target-specific sequencing data of or related to a genome of a subject or a portion thereof; (b) a computer processor operably coupled to the one or more memory locations, wherein the computer processor is programmed to combine the first data input and the second data input to produce a combined data set; and (c) an electronic display coupled to the computer processor, wherein the electronic display presents an output derived from at least a portion of the combined data set, which output is indicative of the presence or absence of one or more polymorphisms in the genome of the subject or the portion thereof. In an embodiment, the electronic display comprises a graphical user interface that is configured to display the at least the portion of the combined data set.

In another aspect of the present disclosure, a system for genomic sequencing comprises: (a) at least one memory location comprising a first data input and second data input, wherein the first data input comprises untargeted sequencing data and the second data input comprises target-specific sequencing data of or related to a genome of a subject or a portion of the genome, wherein the first data input is obtained from a first nucleic acid sample of the subject and the second data input is obtained from a second nucleic acid sample of the subject; (b) a computer processor operably coupled to the at least one memory location, wherein the computer processor is programmed to (i) combine the first data input and the second data input to produce a combined data set and (ii) generate an output from at least a portion of the combined data set, wherein the output is indicative of the presence or absence of one or more polymorphisms in the genome of the subject or a portion of the genome; and (c) an electronic display coupled to the computer processor, wherein the electronic display provides the output for display to a user. In an embodiment, the first data input does not contain target-specific sequencing data. In another embodiment, the second data input contains less than 5%, 10%, 15%, 20%, 25%, 30%, 35%, 40%, 45%, or 50% non-targeted sequence. In another aspect, the computer processor of the system herein is programmed to map the first data input onto a first reference sequence in memory to generate a first alignment. In one embodiment, the computer processor is programmed to map the second data input onto a second reference sequence in memory to generate a second alignment. In another embodiment, the computer processor is programmed to combine the first alignment and the second alignment to generate a uniform alignment in the output. In another embodiment, the computer processor is programed to remove redundant sequences upon combining the first alignment and the second alignment. In another embodiment, the computer processor is programmed to remove redundant sequences upon combining the first data input and the second data input. In another embodiment, the output comprises a uniform alignment that is generated by mapping the combined data set onto one or more reference sequences. In another embodiment, the uniform alignment contains no redundant sequence information. In another embodiment, the output is generated from all of the combined data set. In another embodiment, the first nucleic acid sample and the second nucleic acid sample are the same sample. In another embodiment, the electronic display is part of a remote computer system of the user. In another embodiment, each of the first data input and the second data input comprises variant data, and the computer processor combines the variant data from the first data input and the second data input into the combined data set. In another embodiment, the first data input comprises copy number and/or structural variant data, and the second data input comprises single nucleotide variations (SNV) and/or insertion deletion polymorphism (indel) data.

In another aspect of the present disclosure, a system for genomic sequencing comprises: (a) at least one memory location comprising a first data input and second data input, wherein the first data input comprises untargeted sequencing data and the second data input comprises target-specific sequencing data of or related to a genome of a subject or a portion of the genome, wherein the first data input is obtained from a first nucleic acid sample of the subject and the second data input is obtained from a second nucleic acid sample of the subject; (b) a computer processor coupled to the at least one memory location, wherein the computer processor is programmed to (i) combine the first data input and the second data input to produce a combined data set, and (ii) generate an output from at least a portion of the combined data set, wherein the output is indicative of the presence or absence of one or more polymorphisms in the genome of the subject or a portion of the genome; and (c) an electronic data storage unit coupled to the computer processor, wherein the electronic data storage unit comprises the combined data set and/or the output. In another aspect, the electronic data storage unit described herein comprises the combined data set and the output. In one embodiment, the first data input does not contain target-specific sequencing data. In another embodiment, the second data input contains less than 5%, 10%, 15%, 20%, 25%, 30%, 35%, 40%, 45%, or 50% non-targeted sequence. In another embodiment, the computer processor is programmed to map the first data input onto a first reference sequence in memory to generate a first alignment. In another embodiment, the computer processor is programmed to map the second data input onto a second reference sequence in memory to generate a second alignment. In another embodiment, the computer processor is programmed to combine the first alignment and the second alignment to generate a uniform alignment in the output. In another embodiment, the computer processor is programed to remove redundant sequences upon combining the first alignment and the second alignment. In another embodiment, the computer processor is programmed to remove redundant sequences upon combining the first data input and the second data input. In another embodiment, the output comprises a uniform alignment that is generated by mapping the combined data set onto one or more reference sequences. In another embodiment, the uniform alignment contains no redundant sequence information. In another embodiment, the first nucleic acid sample and the second nucleic acid sample are the same sample. In another embodiment, the output is generated from all of the combined data set. In another embodiment, each of the first data input and the second data input comprises variant data, and the computer processor combines the variant data from the first data input and the second data input into the combined data set. In another embodiment, the first data input comprises copy number and/or structural variant data, and the second data input comprises single nucleotide variations (SNV) and/or insertion deletion polymorphism (indel) data.

In another aspect of the present disclosure, a computer-implemented method comprises: (a) receiving a data input comprising target-specific sequencing data generated from a nucleic acid sample of a subject; (b) annotating, with the aid of a computer processor, the data as targeted or untargeted; and (c) generating, using a computer processor, an output that includes an analysis of the untargeted data, wherein the output is indicative of the absence or presence of one or more polymorphisms in the nucleic acid sample. In an embodiment, the output further comprises analysis of the targeted data. In another embodiment, the target-specific sequencing data is directed to exons, selected genes, genomic regions, variants, or a combination thereof. In another embodiment, the genomic regions comprise one or more polymorphisms, sets of genes, sets of regulatory elements, micro-deletions, homopolymers, simple tandem repeats, regions of high GC content, regions of low GC content, paralogous regions, or a combination thereof. In another embodiment, the one or more polymorphisms comprise one or more insertions, deletions, structural variant junctions, variable length tandem repeats, single nucleotide variants, copy number variants, or a combination thereof. In another embodiment, the one or more polymorphisms are selected from copy number variations, single nucleotide variations, structural variants, micro-deletions, polymorphisms or a combination thereof. In another embodiment, the method further comprises receiving one or more additional data inputs comprising sequencing data generated from one or more additional nucleic acid samples. In another embodiment, the one or more additional data inputs are generated from untargeted sequencing, target-specific sequencing, or a combination thereof. In another embodiment, the one or more additional nucleic acid samples are of the subject. In another embodiment, the method further comprises generating one or more biomedical reports at least in part based on the output. In another embodiment, the method further comprises determining, administering, or modifying a therapeutic regimen for a subject based at least in part on the output. In another embodiment, the method further comprises diagnosing, predicting, or monitoring a disease or a condition in a subject based at least in part on the output.

In another aspect of the present disclosure, a system for analyzing nucleic acid sequencing data comprises: (a) one or more memory locations comprising a data input containing target-specific sequencing data generated from a nucleic acid sample of a subject; and (b) a computer processor coupled to the one or more memory locations and programmed to (i) annotate the data input as targeted or untargeted sequencing data, and (ii) perform an analysis on untargeted sequencing data in the data input to identify the presence or absence of one or more polymorphisms, and (iii) generate an output based on the analysis of the untargeted sequencing data, wherein the output is indicative of the presence or absence of one or more polymorphisms. In an embodiment, the computer processor is programmed to analyze the target-specific sequencing data. In another embodiment, the target-specific sequencing data is whole exome sequencing. In another embodiment, the target-specific sequencing data is from the use of one or more nonrandom primers. In another embodiment, at least about 10% of the data input is annotated as untargeted sequencing data. In another embodiment, the untargeted sequencing data comprises non-exonic sequencing data. In another embodiment, less than about 90% of the data input is annotated as target-specific sequencing data. In another embodiment, the target-specific sequencing data comprises sequencing data pertaining to exomes, genes, genomic regions, or a combination thereof. In another embodiment, the data input further comprises untargeted sequencing data. In another embodiment, the untargeted sequencing data is generated from the nucleic acid sample. In another embodiment, the untargeted sequencing data is whole genome sequencing data.

Another aspect of the present disclosure provides a computer readable medium that comprises machine executable code that, upon execution by one or more computer processors, implements any of the methods above or elsewhere herein.

Another aspect of the present disclosure provides a computer system comprising one or more computer processors and a memory location coupled thereto. The memory location comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "FIGS." herein), of which:

FIG. 2A-2C depict assay and analysis workflows using elements of a more complex workflow;

DETAILED DESCRIPTION

Figure 1:
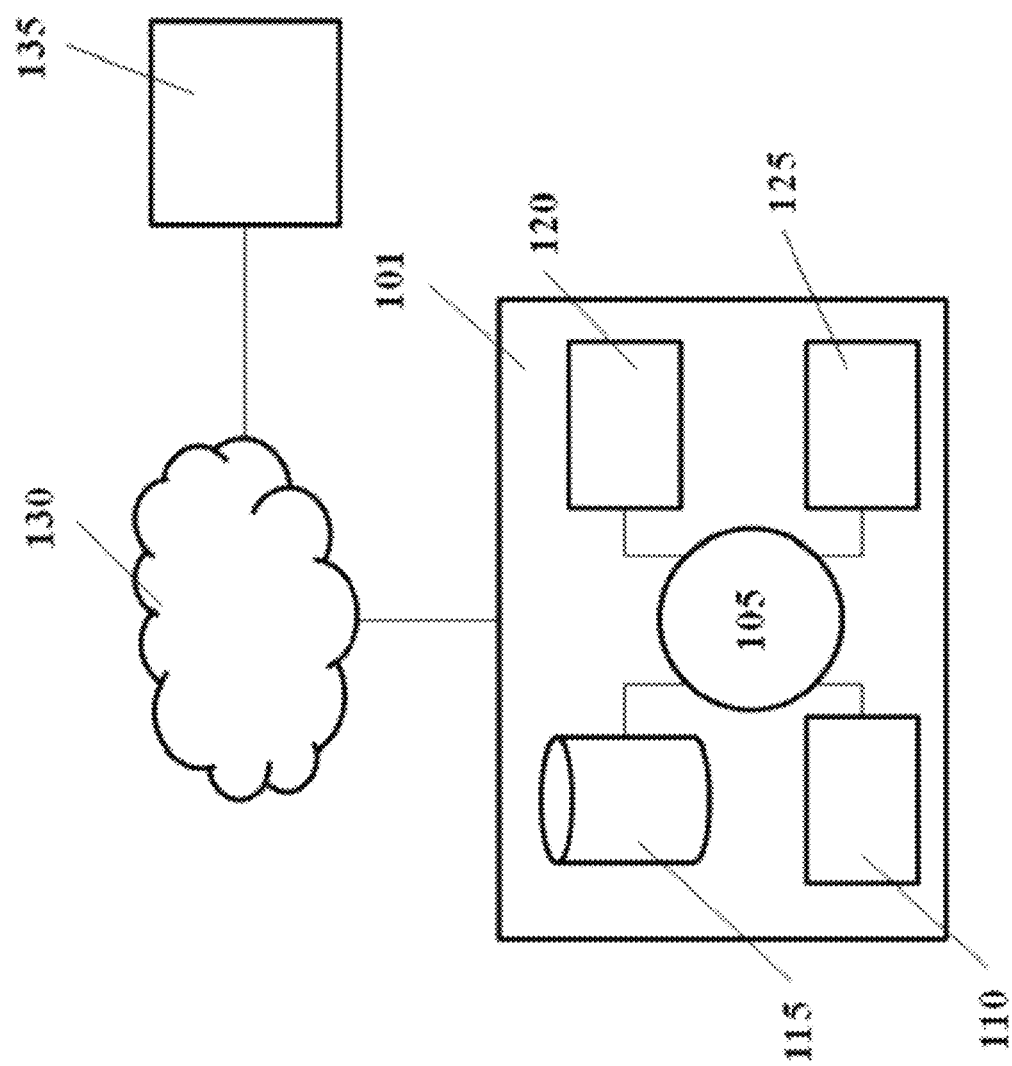
FIG. 1 shows a computer system for implementing the methods of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "subject," as used herein, generally refers to an individual having at least one biological sample that is undergoing analysis. The subject can be undergoing analysis to diagnose, predict or monitor a health, health condition, or well-being of the subject, such as, for example, identify or monitor a disease condition (e.g., cancer) in the subject. The subject can have a sample that is undergoing analysis by a researcher or a service provider, such as a healthcare professional or other individual or entity that employs methods and systems of the present disclosure to analyze the sample.

The term "nucleic acid" as used herein generally refers to a polymeric form of nucleotides of any length. Nucleic acids can include ribonucleotides, deoxyribonucleotides or peptide nucleic acids (PNAs), that comprise purine and pyrimidine bases, or other natural, chemically or biochemically modified, non-natural, or derivatized nucleotide bases. A nucleic acid can be single or double stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose, or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule. The nucleic acid molecule may be a synthetic molecule.

The terms "variant or derivative of a nucleic acid molecule" and "derivative or variant of a nucleic acid molecule," as used herein, generally refer to a nucleic acid molecule comprising a polymorphism. The terms "variant or derivative of a nucleic acid molecule" or "derivative or variant of a nucleic acid molecule" may also refer to nucleic acid product that is produced from one or more assays conducted on the nucleic acid molecule. For example, a fragmented nucleic acid molecule, hybridized nucleic acid molecule (e.g., capture probe hybridized nucleic acid molecule, bead bound nucleic acid molecule), amplified nucleic acid molecule, isolated nucleic acid molecule, eluted nucleic acid molecule, and enriched nucleic acid molecule are variants or derivatives of the nucleic acid molecule.

The terms "detectable label" or "label," as used herein, generally refer to any chemical moiety attached to a nucleotide, nucleotide polymer, or nucleic acid binding factor, wherein the attachment may be covalent or non-covalent. The label can be detectable and render the nucleotide or nucleotide polymer detectable to a user or a system operated by the user. The terms "detectable label" or "label" may be used interchangeably. Detectable labels that may be used in combination with the methods disclosed herein include, for example, a fluorescent label, a chemiluminescent label, a quencher, a radioactive label, biotin, quantum dot, gold, or a combination thereof. Detectable labels include luminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection.

The terms "bound", "hybridized", "conjugated", "attached", and "linked" can be used interchangeably and generally refer to the association of an object to another object. The association of the two objects to each other may be from a covalent or non-covalent interaction. For example, a capture probe hybridized nucleic acid molecule refers to a capture probe associated with a nucleic acid molecule. The capture probe and the nucleic acid molecule are in contact with each other. In another example, a bead bound nucleic acid molecule refers to a bead associated with a nucleic acid molecule.

The terms "target-specific", "targeted," and "specific" can be used interchangeably and generally refer to a subset of the genome that is a region of interest, or a subset of the genome that comprises specific genes or genomic regions. For example, the specific genomic regions can be a region that is guanine and cytosine (GC) rich. Targeted sequencing methods can allow one to selectively capture genomic regions of interest from a nucleic acid sample prior to sequencing. Targeted sequencing involves alternate methods of sample preparation that produce libraries that represent a desired subset of the genome or to enrich the desired subset of the genome. The terms "untargeted sequencing" or "non-targeted sequencing" can be used interchangeably and generally refer to a sequencing method that does not target or enrich a region of interest in a nucleic acid sample. The terms "untargeted sequence", "non-targeted sequence," or "non-specific sequence" generally refer to the nucleic acid sequences that are not in a region of interest or to sequence data that is generated by a sequencing method that does not target or enrich a region of interest in a nucleic acid sample. The terms "untargeted sequence", "non-targeted sequence" or "non-specific sequence" can also refer to sequence that is outside of a region of interest. In some cases, sequencing data that is generated by a targeted sequencing method can comprise not only targeted sequences but also untargeted sequences.

Where a range of values is provided, it is understood that each intervening value between the upper and lower limits of that range, to the tenth of the unit of the lower limit, unless the context clearly dictates otherwise, is also specifically disclosed. Each smaller range between any stated value or intervening value in a stated range, and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of operations recited or disclosed, or in any other logical order.

Sample Processing and Data Analysis

This disclosure provides computer-implemented methods and systems for sample processing and data analysis such as genome sequencing or other types of sequencing. The computer-implemented method, genome sequencing, or sequencing methods can comprise receiving a first data input comprising untargeted sequencing data (i.e., whole genome sequencing data), and a second data input comprising target-specific sequencing data, followed by combining or analyzing the first and second data inputs and generating an output derived from the combined data or analysis. The untargeted sequencing data (i.e., whole genome sequencing data) can comprise single reads or, for example, between about 1 to about 5 gigabases or less. The untargeted sequencing data (i.e., whole genome sequencing data) can comprise paired-end reads. The untargeted sequencing data (i.e., whole genome sequencing data) can comprise mate-pair reads. The paired-end reads and/or the mate-pair reads may have insert-sizes of larger than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 30.0, 40.0, 50.0, 60.0, 70.0, 80.0, 90.0, or 100.0 kilobasepairs. When paired-end reads and/or mate-pair reads are used, an insert-size can be the size of DNA inserted between the adaptors which enable amplification and sequencing of the DNA. The target-specific sequencing may be exome sequencing. The output can provide sequencing information that comprises sets of genes or regulatory elements, or one or more polymorphisms of genomic regions.

In some cases, sample processing includes nucleic acid sample processing and subsequent nucleic acid sample sequencing such as genome sequencing or other types of sequencing. Some or all of a nucleic acid sample may be sequenced to provide sequence information including untargeted sequencing or target-specific sequencing, which may be received, stored, analyzed or otherwise maintained in an electronic, magnetic, or optical storage location or by a computer. The sequence information may be analyzed or implemented with the aid of a computer processor, and the analyzed sequence information may be stored in an electronic storage location. The electronic storage location may include a pool or collection of sequence information and analyzed sequence information generated from the nucleic acid sample.

In some cases, the subjects of the present disclosure may be mammals or non-mammals. Preferably the subjects are a mammal, such as, a human, non-human primate (e.g., apes, monkeys, chimpanzees), cat, dog, rabbit, goat, horse, cow, pig, and sheep. Even more preferably, the subject is a human. For example, sequences of the present disclosure can include sequences that are from a human subject. In some cases, reference sequences of the present disclosure can include sequences that are from a human subject. The subject may be male or female; the subject may be a fetus, infant, child, adolescent, teenager or adult. Non-mammals include, but are not limited to, reptiles, amphibians, avians, and fish. A reptile may be a lizard, snake, alligator, turtle, crocodile, and tortoise. An amphibian may be a toad, frog, newt, and salamander. Examples of avians include, but are not limited to, ducks, geese, penguins, ostriches, and owls. Examples of fish include, but are not limited to, catfish, eels, sharks, and swordfish.

In some examples, a user, such as a healthcare provider, may request a first set of sequence information, a first data input, or analyzed sequence information from the pool. Concurrently or subsequently, the user may request a second set of sequence information, a second data input or analyzed sequence information from the pool. The first set may be different from the second set. The first set may be combined with the second set with the aid of a computer processor to generate an output comprising the combined data. The sequencing information can comprise sets of genes or regulatory elements, or one or more polymorphisms. The one or more polymorphisms can be of genomic regions. The whole genome sequencing data can comprise single reads or between about 1 to about 5 gigabases or less.

The target-specific sequencing can include data from a targeted sequencing assay, e.g., exome sequencing. The target-specific sequencing data may comprise a targeted portion and an untargeted portion of the sequencing data, i.e., an exonic data and a non-exonic data. The untargeted portion of the target-specific sequencing data, such as the non-exonic data, may provide sequence information of genomic regions spanning part or all of the whole genome regions outside of the targeted region or exons. The computer-implemented methods or methods of genome sequencing and/or sequencing may generate an output that is indicative of or comprising sequence information of the genomic regions comprising one or more polymorphisms, sets of genes, sets of regulatory elements, micro-deletions, homopolymers, simple tandem repeats, regions of high GC content, regions of low GC content, paralogous regions or a combination thereof based on the exonic and non-exonic data from exome sequencing data. The GC-content can be the percentage of nitrogenous bases on a DNA molecule that are either guanine or cytosine. In some cases, the methods further comprise whole genome sequencing of single reads or less, or for example, less than about 5 gigabases. In some cases, the methods further comprise whole genome sequencing of paired-end reads. In some cases, the methods further comprise whole genome sequencing of mate-pare reads.

Disclosed herein are computer-implemented methods or methods for analyzing a nucleic acid sample. The methods of the disclosure can comprise (a) receiving a first data input, the first data input comprising untargeted sequencing data generated from a first nucleic acid sample; (b) receiving a second data input, the second data input comprising target-specific sequencing data generated from a second nucleic acid sample; (c) combining and/or analyzing, with the aid of a computer processor, the first data input and the second data input to produce combined data and/or analysis; and (d) generating, with the aid of a computer processor, an output derived from the combined data and/or analysis. In some cases, the first nucleic acid sample and the second nucleic acid sample are obtained from the same source or the same subject. The output can be indicative of, or comprise a detection of, the presence or absence of one or more polymorphisms of the first nucleic acid sample, the second nucleic acid sample, and/or the genome of the subject.

In an aspect of the present disclosure, systems for genomic sequencing or the computer-implemented methods are provided. The system can comprise (a) one or more memory locations comprising a first data input and second data input, wherein the first data input comprises untargeted sequencing data and the second data input comprises target-specific sequencing data of or related to a genome of a subject or a portion thereof; (b) a computer processor operably coupled to the one or more memory locations, wherein the computer processor is programmed to combine and/or analyze the first data input and the second data input to produce a combined data set and/or analysis, and generates an output from the combined data set and/or analysis, which output is indicative of the presence or absence of one or more polymorphisms in the genome of the subject or the portion thereof. In some cases, the systems can further comprise (c) an electronic display, coupled to the computer processor, wherein the electronic display presents an output derived from at least a portion of the combined data set and/or analysis in numeric and/or graphical form. The output can comprise detection of or is indicative of presence or absence of one or more polymorphisms.

Also provided herein are computer-implemented methods comprising (a) receiving, by a computer, a data input, the data input comprising a data from a target-specific sequencing data from a targeted sequencing method, generated from a nucleic acid sample; (b) annotating, by the computer or with the aid of a computer processor, the data as targeted or untargeted (e.g., exonic or non-exonic); and (c) generating, by the computer, an output comprising analysis of the untargeted or non-exonic data. The output can comprise detection of or is indicative of one or more polymorphisms in the nucleic acid sample.

Also disclosed herein are systems for sequencing comprising (a) one or more memory locations comprising a data input, wherein the data input comprises sequencing data generated by a target-specific sequencing method; (b) a computer processor coupled to the one or more memory location, wherein the computer processor is programmed to annotate the data input as targeted or untargeted (i.e., exonic or non-exonic) sequencing data, analyze the untargeted sequencing data, and generate an output based on the annotation and/or the analysis of the untargeted input data. In some cases, the output comprises detection of one or more polymorphisms, or the output is indicative of one or more polymorphisms.

Types of Data

In some embodiments, the computer-implemented methods and systems for genome sequencing or sequencing may include data that is generated by untargeted sequencing or a target-specific sequencing assay or method. The target-specific sequencing can be a subset of the genome that is a region of interest (e.g., to a user). Non-limiting examples include exome, a particular chromosome, a set of genes, or genomic regions. Targeted sequencing methods can allow one to selectively capture genomic regions of interest from a nucleic acid sample prior to sequencing. Targeted sequencing involves alternate methods of sample preparation that produce libraries that represent a desired subset of the genome or to enrich the desired subset of the genome. In some cases, this subset is the exome, which can be functionally important and therefore can be a high candidate target for medical/gene-related research. By targeting the exome of an individual, it is possible to identify known genetic variants that could promote a disease phenotype. Additionally, by targeting the exomes of multiple patients, rare variants can be found, and further analysis on the functional consequences of the mutation can be completed. Exome sequencing can use either a 'solution-based capture' or 'microarray capture' method. The array-based method can be used when the target design may only be used across a small number of samples (up to 20 or so). Studies that focus on even smaller regions of the genome may also employ polymerase chain reaction (PCR) based approaches. Some methods for exome sequencing are described in Bainbridge, M. et al., (2010) Whole exome capture in solution with 3 Gbp of data. Genome Biology 11:R62, Kiialainen, A. et al. (2011) Performance of Microarray and Liquid Based Capture Methods for Target Enrichment for Massively Parallel Sequencing and SNP Discovery. PLoS ONE 6(2):e16486, or Tewhey, R. et al. (2009) Microdroplet-based PCR enrichment for large-scale targeted sequencing. Nature Biotechnology 27:1025-1031, hereby incorporated by reference in their entirety.

Untargeted sequencing can be a sequencing method that does not target or enrich a region of interest in a nucleic acid sample. The untargeted or comprehensive sequencing may be whole genome sequencing or whole transcriptome sequencing. The untargeted sequence can be the nucleic acid sequences that are not in a region of interest or sequence data that is generated by a sequencing method that does not target or enrich a region of interest in a nucleic acid sample. The untargeted sequence can be a sequence that is outside of a region of interest. In some cases, sequencing data that is generated by a targeted sequencing method can comprise not only targeted sequences but also untargeted sequences.

The types of target-specific sequencing may be whole exome sequencing, RNA sequencing, DNA sequencing, or targeted sequencing of one or more specific genes or genomic regions, or a combination thereof. The specific genes or genomic regions may be indicative of any specific pathways or specific disorders, such as a genetic disorder or single nucleotide polymorphism. The genomic regions may comprise one or more polymorphisms, sets of genes, sets of regulatory elements, micro-deletions, homopolymers, simple tandem repeats, regions of high GC content, regions of low GC content, paralogous regions or a combination thereof. Utilizing the above sequencing assays allows for untargeted sequencing of the sample or targeted sequencing of the sample. In untargeted sequencing, such as whole genome sequencing or whole transcriptome sequencing, the entire DNA or RNA structure is examined. In targeted sequencing assays, only targeted or specific portions of the DNA or RNA are intended to be sequenced. A variety of different sequencing methods and assays can be found in U.S. Patent Publication No. 2013/0178389 A1, hereby incorporated by reference in its entirety. In some embodiments, the sequencing data may comprise sequence information of at least about 1; 2; 3; 4; 5; 6; 7; 8; 9; 10; 15; 20; 25; 30; 35; 40; 45; 50; 60; 70; 80; 90; 100; 120; 140; 160; 180; 200; 240; 280; 300; 350; 400; 450; 500; 600; 700; 800; 1000; 1500; 2000; 2500; 3000; 3500; 4000; 5000; 7500; 10,000; 15,000; 20,000; 30,000; 45,000; 50,000; 60,000; 100,000; 200,000; 400,000; 600,000; 1 million; 1.5 million; 2 million or more genomic markers or genes.

Methods and systems as described herein can comprise combining and/or analyzing a first data input and a second data input to generate an output derived from the combined data and/or analysis. In some cases, the combining and/or analyzing can further comprise combining and/or analyzing one or more different data inputs. In some cases, the methods and systems can comprise combining and/or analyzing data inputs from one or more sequencing data. The one or more sequencing data can be the same type or different. The one or more sequencing data can be partial sequencing data or complete sequencing data of any kind. The one or more sequencing data can be target-specific sequencing data. In some cases, methods and systems as described herein can comprise combining and/or analyzing an untargeted sequencing data such as whole genome sequencing data with one or more target-specific sequencing data. The untargeted sequencing data can comprise entirely the non-specific or untargeted portion of the target-specific sequencing data. For example, the non-exonic portion of a whole exome sequencing data can be used as the untargeted sequencing data in methods and systems as described herein. In some cases, a portion of the untargeted sequencing data can comprise the non-specific or untargeted portion of the target-specific sequencing data. The one or more target-specific sequencing data can be the same type or different. For example without limitation, the methods and systems can comprise combining and/or analyzing whole genome sequencing data, whole exome sequencing data with specific gene sequencing data targeting a specific genetic disorder. Each of the one or more data inputs can be from the same or different nucleic acid samples.

Methods and systems described herein can comprise receiving a data input and analyzing and/or annotating the data input based on one or more parameters. The parameters can be related to the untargeted or targeted portion of the data input. For example without limitations, methods and systems as described herein can comprise receiving a data input comprising target-specific sequencing data (i.e., whole exome sequencing data) generated from a nucleic acid sample. For example without limitation, the methods and systems as described herein can comprise analyzing and/or annotating the data pertaining to the first nucleic acid sample as targeted or untargeted, such as exonic or non-exonic. The methods and systems as described herein may further comprise generating an output comprising a subset of the data input such as the untargeted portion of the data, or for example without limitation, the non-exonic data. The output can further comprise the targeted portion of the data such as exonic data along with the annotated untargeted portion of the data such as non-exonic data. In some cases, the methods and systems as described herein can further comprise receiving a data input comprising a target-specific sequencing data such as whole exome sequencing data and one or more additional data inputs comprising sequencing data generated from one or more nucleic acid samples. The one or more additional data inputs can be generated by any sequencing methods such as untargeted sequencing, target-specific sequencing, or a combination thereof. Similarly, the one or more additional data inputs can be annotated based on one or more parameters. Output comprising at least a portion or a subset of the one or more additional data can also be generated. The methods and systems as described herein can further comprise combining and/or analyzing one or more subsets of the one or more additional data inputs with a subset of the first data input. The methods and systems can further comprise generate an output comprising the combined data and/or analysis. The methods and systems as disclosed herein can further comprise generating one or more biomedical reports based on the output. The medical reports may be used for determining, administering, or modifying a therapeutic regimen for a subject.

In some cases, the combined data or analysis can be generated by a computer system, as described elsewhere herein. The combined data can be displayed electronically. At least a portion of the combined data can be presented in numeric and/or graphical form. In some cases, the methods and systems as described herein can comprise combining and/or analyzing data from at least 2, 3, 4, 5, 6, 7, 8, 9 or 10 different or same sources. In some cases, the display or the combined data is based on data from one or more databases or data sources. The sources of data or databases can be any types of databases that are suitable for the methods and systems as described herein. In some embodiments, the databases or data sources can comprise one or more medical records, clinical notes, genomic databases, variant database, biomedical database, clinical databases, scientific databases, disease databases, biomarker databases, and the like. The databases or data sources can be publicly-available or proprietary. In some embodiments, the databases or data sources can comprise proprietary databases. The proprietary databases can be a database that is specific to one or more diseases. For example, without limitation, the proprietary database can be a variant database or a pharmacogenomics database. The publicly-available databases can comprise Orphanet, Human Phenotype Ontology (HPO), *Online Mendelian Inheritance in Man* (OMIM), Model Organism Gene Knock-Out databases, Kegg Disease Database, dbSNP, and the like.

Untargeted Sequencing

Another aspect provides computer-implemented methods and systems for genomic sequencing or other sequencing. The methods can provide sequence information regarding one or more polymorphisms, sets of genes, sets of regulatory elements, micro-deletions, homopolymers, simple tandem repeats, regions of high GC content, regions of low GC content, paralogous regions, or a combination thereof. In some cases, the untargeted sequencing can be whole genome sequencing. In some cases, the untargeted sequencing data can be the untargeted portion of the data generated from a target-specific sequencing assay. The methods can generate an output comprising a combined data set comprising target-specific sequencing data and a low coverage untargeted sequencing data as supplement to target-specific sequencing data. Non-limiting examples of the low coverage untargeted sequencing data include low coverage whole genome sequencing data or the untargeted portion of the target-specific sequencing data. This low coverage genome data can be analyzed to assess copy number variation or other types of polymorphism of the sequence in the sample. The low coverage untargeted sequencing (i.e., single run whole genome sequencing data) can be fast and economical, and can deliver genome-wide polymorphism sensitivity in addition to the target-specific sequencing data. In addition, variants detected in the low coverage untargeted sequencing data can be used to identify known haplotype blocks and impute variants over the whole genome with or without targeted data.

Untargeted sequencing (i.e., whole genome sequencing) can determine the complete DNA sequence of the genome at one time. Untargeted sequencing (i.e., whole genome sequencing or the non-exonic portion of whole exome sequencing) can cover sequences of almost about 100 percent, or about 95%, of the sample's genome. In some cases, the untargeted sequencing (i.e., whole genome sequencing or non-exonic portion of the whole exome sequencing) can cover sequences of the whole genome of the nucleic acid sample of about or at least about 99.999%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50%.

In some cases, the output can have a coverage of about or at least about 99.999%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% of the whole genome of the nucleic acid sample from a subject.

In some cases, the computer-implemented methods and systems receives a first data input comprising untargeted sequencing data generated from a first nucleic acid sample. The untargeted sequencing data can be whole genome sequencing data or the untargeted portion of a target-specific sequencing data. The whole genome sequencing data can be a low coverage whole genome sequencing data. The untargeted sequencing data can comprise coverage of about or at least about 5, 4.5, 4, 3.5, 3, 2.5, 2, 1.5, or 1 gigabases; about or at least about 900, 850, 800, 750, 700, 650, 600, 550, 500, 450, 400, 350, 300, 250, 200, 150, 100, 90, 80, 70, 60, 55, 50, 45, 40, 35, 30, 25, 20, 15, 10, 5, 4, 3, 2, or 1 megabases. The untargeted sequencing data can comprise coverage of less than about 500, 450, 400, 350, 300, 250, 200, 190, 180, 170, 160, 150, 140, 130, 120, 110, 100, 95, 90, 85, 80, 75, 70, 65, 60, 55, 50, 45, 40, 35, 30, 25, 20, 15, 10, 9, 8, 7, 6, 5, 4, 3, 2, or 1 gigabases. The untargeted sequencing data can comprise between about 1-5, 0.5-10, 1-10, 0.5-5, 0.1-5, 2-5, 0.1-2, or 0.1-1 gigabases.

The untargeted sequencing data (i.e., whole genome sequencing data or the untargeted portion of a target-specific sequencing data) can be analyzed by assigning the data into a plurality of genomic bins and measuring the number of sequence reads in each of a plurality of genomic bins. The genomic bins can have different sizes comprising different numbers of basepairs to assess genomic regions such as the one or more polymorphisms or copy number variations (CNV) of the sequence of the sample. The genomic bin size should be selected to balance the tradeoff, for example without limitation, between sensitivity to small CNVs and reduction of false positive detections. In some embodiments, the size of genomic bins can be between about 100 to about 1,000,000 basepairs. In some embodiments, the size of genomic bins can be about, less than about, or at least about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, or 300 megabasepairs; 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 990 kilobasepairs; or 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 990 basepairs. In some embodiments, the size of the genomic bins can be higher than 300 megabasepairs. In some embodiments, the size of the genomic bins can be the size of a chromosome or the average size of chromosomes in a subject. In some embodiments, the size of genomic bins can be about 100 basepairs. In some embodiments, the size of genomic bins can be about 1 kilobasepairs. In some embodiments, the size of genomic bins can be between about 1 kilobasepairs to 20 kilobasepairs. In some embodiments, size of genomic bins can be between about 100-0.5 million, 100-1.5 million, 300-0.5 million, 300-1 million, 300-1.5 million, 500-0.5 million, 500-1 million, or 500-1.5 million basepairs.

In some cases, the untargeted sequencing (i.e., whole genome sequencing of one single read) covering about 3 gigabasepairs can deliver a genome-wide structural variation (SV) sensitivity from 50 kilobasepairs upwards. In some embodiments, the untargeted sequencing (i.e., whole genome sequencing) can result in a genome-wide structural variation sensitivity from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or, 100 kilobasepairs upwards. In some embodiments, the untargeted sequencing (i.e., whole genome sequencing) can result in a genome-wide structural variation sensitivity from less than about 10, 20, 30, 40, 50, 60, 70, 80, 90 or 100 kilobasepairs upwards. In addition, variants detected in the untargeted sequencing data can be used to identify known haplotype blocks and impute variants over the whole genome with or without targeted sequencing data such as whole exome sequencing data.

In some embodiments, the whole genome sequencing data can comprise single reads. Costs and time for whole genome sequencing can be lowered by eliminating the second or third reads. In some embodiments, the whole genome sequencing data can comprise less than single reads. For example, the whole genome sequencing data can comprise 0.1 to 1 reads, or 0.5 to 1 reads. In some embodiments, the whole genome sequencing data can comprise about, less than about, or at least about 0.1, 0.2, 0.25, 0.3, 0.4, 0.5, 0.6, 0.7, 0.75, 0.8, 0.9, 0.95, or 0.99 reads. In some embodiments, the whole genome sequencing data can further comprise second reads. In some embodiments, the whole genome sequencing data can further comprise third reads. In some embodiments, the whole genome sequencing data can further comprise $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, or $43^{rd}$ reads. In some embodiments, the whole genome sequencing data can further comprise less than 1, 2, 3, 4, 5, 10, 15, 20, 25, 30, 35, 40, 45, or 50 reads. Multiple reads may provide additional structural variation detection modes, e.g., anomalous read separation. However, the whole genome sequencing data comprising single reads can assess large copy number variations using the algorithms described herein in the instant invention.

Target-Specific Sequencing

Target-specific sequencing is selective sequencing of specific genomic regions, specific genes, or whole exome sequencing. Non-limiting examples of the genomic regions include one or more polymorphisms, sets of genes, sets of regulatory elements, micro-deletions, homopolymers, simple tandem repeats, regions of high GC content, regions of low GC content, paralogous regions, degenerate-mapping regions, or a combination thereof. The sets of genes or regulatory elements can be related to one or more specific genetic disorders of interest. The one or more polymorphisms can comprise one or more single nucleotide variations (SNVs), copy number variations (CNVs), insertions, deletions, structural variant junctions, variable length tandem repeats, or a combination thereof.

In some cases, the target-specific sequencing data can comprise sequencing data of some untargeted regions. One example of the target-specific sequencing is the whole exome sequencing. Whole exome sequencing is target-specific or selective sequencing of coding regions of the DNA genome. The targeted exome is usually the portion of the DNA that translates into proteins, or namely exonic sequence. However, regions of the exome that do not translate into proteins may also be included within the sequence, namely non-exonic sequences. Non-exonic sequences are usually not included in exome studies. In the human genome there can be about 180,000 exons: these can constitute about 1% of the human genome, which can translate to about 30 megabases (Mb) in length. It can be estimated that the protein coding regions of the human genome can constitute about 85% of the disease-causing mutations. The robust approach to sequencing the complete coding region (exome) can be clinically relevant in genetic diagnosis due to the current understanding of functional consequences in sequence variation, by identifying the functional variation that is responsible for both mendelian and common diseases without the high costs associated with a high coverage whole-genome sequencing while maintaining high coverage in sequence depth. Other aspect of the exome sequencing can be found in Ng S B et al., "Targeted capture and massively parallel sequencing of 12 human exomes," Nature 461 (7261): 272-276 and Choi M et al., "Genetic diagnosis by whole exome capture and massively parallel DNA sequencing," Proc Natl Acad Sci USA 106 (45): 19096-19101.

In some embodiments, the methods and systems as described herein comprise receiving, combining and/or analyzing target-specific sequencing (i.e., whole exome sequencing) data and untargeted sequencing data (i.e., low-coverage whole genome sequencing data). The methods and systems as described herein can assess copy number variation or other types of polymorphisms of the genome, and deep coverage of the functional consequences in sequence variation. In some embodiments, the target-specific sequencing (i.e., whole exome sequencing) data constitute about 1% of the human genome. In some embodiments, the target-specific sequencing (i.e., whole exome sequencing) data constitute about, at least about, or less than about 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008%, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% of the human genome.

In some cases, the target-specific sequencing data can comprise sequence data of about 180,000 exons. In some embodiments, the target-specific sequencing data can comprise sequence data of about, less than about, at least about 1000, 5000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, 150,000, 155,000, 160,000, 165,000, 170,000, 175,000, or 180,000 exons. In some embodiments, the target-specific sequencing data can comprise sequence data of about, at least about, less than about 10%, 20%, 30%, 40%, 50%, 60%, 70%, 80%, 90%, 95%, 99%, 99.5%, 99.9%, or 100% exons of the total exons in the whole genome.

In some embodiments, the target-specific sequencing data can comprise about 30 megabasepairs of sequences. In some embodiments, the target-specific sequencing data can comprise about, at least about, less than about 1, 2, 3, 4, 5, 6, 7, 8, 9, 10, 15, 20, 25, 30, 35, 40, 45, 50, 55, 60, 65, 70, 75, 80, 85, 90, 95, or 100 megabasepairs; or 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 990 kilobasepairs.

The target-specific sequencing techniques used in the methods of the invention may generate at least 10 reads per run, at least 50 reads per run, at least 100 reads per run, at least 200 reads per run, at least 300 reads per run, at least 400 reads per run, at least 500 reads per run, at least 600 reads per run, at least 700 reads per run, at least 800 reads per run, at least 900 reads per run, at least 1000 reads per run, at least 5,000 reads per run, at least 10,000 reads per run, at least 50,000 reads per run, at least 100,000 reads per run, at least 500,000 reads per run, or at least 1,000,000 reads per run. Alternatively, the target-specific sequencing technique used in the methods of the invention generates at least 1,500,000 reads per run, at least 2,000,000 reads per run, at least 2,500,000 reads per run, at least 3,000,000 reads per run, at least 3,500,000 reads per run, at least 4,000,000 reads per run, at least 4,500,000 reads per run, or at least 5,000,000 reads per run.

In some embodiments, the target-specific sequencing data may comprise sequence information of 1; 2; 3; 4; 5; 6; 7; 8; 9; 10; 15; 20; 25; 30; 35; 40; 45; 50; 60; 70; 80; 90; 100; 120; 140; 160; 180; 200; 240; 280; 300; 350; 400; 450; 500; 600; 700; 800; 1000; 1500; 2000; 2500; 3000; 3500; 4000; 5000; 7500; 10,000; 15,000; 20,000; 30,000; 45,000; 50,000; 60,000; 100,000; 200,000; 400,000; 600,000; 1 million; 1.5 million; 2 million or more genomic DNA markers or genes.

In some embodiments, the target-specific sequencing data (i.e., whole exome sequencing data or the protein coding regions of the human genome or disease-targeted specific sets of genes) can constitute about 85% of the disease-causing mutations. In some embodiments, the target-specific sequencing data can comprise sequence information that can constitute about, at least about, less than about 10%, 15%, 20%, 25%, 30%, 35%, 40%, 45%, 50%, 55%, 60%, 65%, 70%, 75%, 80%, 85%, 90%, 95%, 99%, or 100% of the disease-causing mutations. The disease-causing mutations can correspond to at least 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 different diseases or conditions.

In some cases, the non-exonic data from the exome sequencing data can cover a large portion of the whole genome and can detect copy number variations and other polymorphisms in the genome. In some cases, the methods and systems as described herein can comprise annotating, by a computer or other means, the target-specific sequencing data (i.e., exome sequencing data) pertaining to a nucleic acid sample as targeted or untargeted (i.e., exonic or non-exonic). In some cases, the methods and systems as described herein can further comprise generating, by a computer or other means, an output comprising analysis of the untargeted data (i.e., non-exomic data). The untargeted data (i.e., non-exomic data) can be used in some embodiments of the instant invention, to provide access to or detect copy number variations or other types of polymorphisms or genomic regions of the whole genome. The methods and systems as described herein can further comprise combining and/or analyzing the untargeted data annotated from the target-specific sequencing data (i.e., non-exonic data) and targeted data such as exonic data or other target-specific sequencing data to generate an output. The non-exonic data can have coverage of the genome similar to that of a low coverage whole genome sequencing, and as a result, it can be performed to detect copy number variations or other types of polymorphisms or genomic regions of the genome. The untargeted data such as non-exonic data can be annotated from the target-specific sequencing data such as whole exome sequencing data using any methods well known in the art, for example without limitation, the methods described in Guo Y et al., "Exome sequencing generates high quality data in non-target regions," BMC Genomics. 2012 May 20; 13:194 and Asan et al., "Comprehensive comparison of three commercial human whole-exome capture platforms," Genome Biol. 2011 Sep. 28; 12(9).

In some cases, the untargeted data from the target-specific sequencing (i.e., non-exonic sequencing data) can comprise coverage of about or at least about 5, 4.5, 4, 3.5, 3, 2.5, 2, 1.5, or 1 gigabases; about or at least about 900, 850, 800, 750, 700, 650, 600, 550, 500, 450, 400, 350, 300, 250, 200, 150, 100, 90, 80, 70, 60, 55, 50, 45, 40, 35, 30, 25, 20, 15, 10, 5, 4, 3, 2, or 1 megabases. The untargeted data from the target-specific sequencing (i.e., non-exonic sequencing data) can comprise coverage of less than about 900, 850, 800, 750, 700, 650, 600, 550, 500, 450, 400, 350, 300, 250, 200, 150, 100, 90, 80, 70, 60, 55, 50, 45, 40, 35, 30, 25, 20, 15, or 10 megabases. The untargeted data from the target-specific sequencing (i.e., non-exonic sequencing data) can comprise between about 1-5, 0.5-10, 1-10, 0.5-5, 0.1-5, 0.1-2, or 0.1-1 gigabases.

In some cases, the untargeted data from the target-specific sequencing (i.e., non-exonic sequencing data) can comprise about 50% or more of the target-specific sequencing data such as whole exome sequencing data. In some cases, the untargeted data from the target-specific sequencing (i.e., non-exonic sequencing data) can comprise about 10% or more of the target-specific sequencing data such as whole exome sequencing data. In some embodiments, the untargeted data from the target-specific sequencing (i.e., non-exonic sequencing data) can comprise about 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, or more of the target-specific sequencing data such as whole exome sequencing data.

Output Data

Methods and systems as disclosed herein can comprise generating an output data. The output data can comprise any sequencing information data that is generated by methods as described elsewhere in this specification. For example without limitation, the output can comprise whole genome sequencing data, whole exome sequencing data, other target-specific sequencing data, a subset of a sequencing data, non-exonic data, exonic data or a combination thereof. The one or more outputs, sets of outputs, combined outputs, and/or combined sets of outputs may comprise one or more biomedical reports, biomedical outputs, rare variant outputs, pharmacogenetic outputs, population study outputs, case-control outputs, biomedical databases, genomic databases, disease databases, or net content.

The methods and systems as described herein can comprise generating an output comprising detections of one or more genomic regions selected from copy number variations, single nucleotide variations, structural variants, one or more polymorphisms, sets of genes, sets of regulatory elements, micro-deletions, homopolymers, simple tandem repeats, regions of high GC content, regions of low GC content, paralogous regions, degenerate-mapping regions, or a combination thereof.

The target-specific sequencing data may be based on genomic regions that comprise one or more polymorphisms, sets of genes, sets of regulatory elements, micro-deletions, homopolymers, simple tandem repeats, regions of high GC content, regions of low GC content, paralogous regions, degenerate-mapping regions, or a combination thereof. This sequencing may take the form of mutational analysis for one or more polymorphisms such as single nucleotide polymorphism (SNP) analysis or single nucleotide variations (SNV), insertion deletion polymorphism (InDel) analysis, variable number of tandem repeat (VNTR) analysis, copy number variation (CNV) analysis (alternatively referred to as copy number polymorphism), partial or whole genome sequencing, or combination thereof. The types of polymorphisms that can be analyzed can be any polymorphism that is known in the art. The types of polymorphism may be insertions, deletions, structural variant junctions, variable length tandem repeats, single nucleotide mutations, single nucleotide variations, copy number variations, or a combination thereof. In preferred embodiments, the polymorphism is copy number variation or single nucleotide variant. Methods for performing genomic analyses are known to the art and may include high throughput sequencing such as but not limited to those methods described in U.S. Pat. Nos. 7,335,762; 7,323,305; 7,264,929; 7,244,559; 7,211,390; 7,361,488; 7,300,788; and 7,280,922, each of which is entirely incorporated herein by reference. Methods for performing genomic analyses may also include microarray methods as described hereinafter.

Algorithms and Models

In some cases, the methods and systems as described herein are used to generate an output comprising detection and/or quantitation of genomic DNA regions such as a region containing a DNA polymorphism. In some cases, the detection of the one or more genomic regions is based on one or more algorithms, depending on the source of data inputs or databases that are described elsewhere in the instant specification. Each of the one or more algorithms can be used to receive, combine and generate data comprising detection of genomic regions (i.e., polymorphisms). In some embodiments, the instant method and system can comprise detection of the genomic regions that is based on one or more, two or more, three or more, four or more, five or more, six or more, seven or more, eight or more, nine or more or ten or more algorithms. The algorithms can be machine-learning algorithms, computer-implemented algorithms, machine-executed algorithms, automatic algorithms and the like.

The resulting data for each nucleic acid sample can be analyzed using feature selection techniques including filter techniques which assess the relevance of features by examining the intrinsic properties of the data, wrapper methods which embed the model hypothesis within a feature subset search, and embedded techniques in which the search for an optimal set of features is built into an algorithm or model.

In some situations, an assay is used to generate a first set of data containing at least some or all variants (e.g., single nucleotide variations or insertion deletion polymorphism) from the exome of a nucleic sample of a subject, and another assay is used to generate a second set of data that contains at least some or all variants (e.g., structural variants or copy number variations) from the whole genome of the nucleic sample of the subject. The first set of data and second set of data can be combined into a combined output. In some cases, variants from the first set of data and variants from the second set of data are combined into the combined output. The assays can be nucleic acid sequencing or nucleic acid amplification (e.g., PCR) with two different sample preparation methods that can be directed to identifying variants in the exome and variants in the genome. For example, variants in the exome can be identified using target-specific sequencing (e.g., using target specific primers), and variants in the whole genome can be identified using untargeted sequencing.

In some cases, the detection of the one or more genomic regions is based on one or more statistical models. Statistical models or filtering techniques useful in the methods of the present invention include (1) parametric methods such as the use of two sample t-tests, ANOVA analyses, Bayesian frameworks, and Gamma distribution models (2) model free methods such as the use of Wilcoxon rank sum tests, between-within class sum of squares tests, rank products methods, random permutation methods, or TNoM which involves setting a threshold point for fold-change differences in expression between two datasets and then detecting the threshold point in each gene that minimizes the number of missclassifications (3) and multivariate methods such as bivariate methods, correlation based feature selection methods (CFS), minimum redundancy maximum relevance methods (MRMR), Markov blanket filter methods, Markov models, Hidden Markov Model (HMM), and uncorrelated shrunken centroid methods. In some cases, the Hidden Markov Model (HMM) is given an internal state, wherein the internal state is set according to an overall copy number of a chromosome in the first or second nucleic acid sample. In an instance, for a diploid chromosome, the HMM's internal states can be homozygous deletion (locally zero copies), heterozygous deletion (locally one copy), normal (locally two copies), duplication (more than two copies), and reference Gap (present as a state to distinguish gaps from Homozygous deletions). In another instance, for a Haploid chromosome (e.g., X or Y in a male), the HMM's internal states can be homozygous deletion (locally zero copies), normal (locally two copies), duplication (more than two copies), and reference Gap (present as a state to distinguish gaps from Homozygous deletions). For example, for a Haploid chromosome, there may be no heterozygous deletion state available. In another instance, for trisomic and/or tetrasomic, additional intermediate the HMM states may have an additional intermediate state, wherein the intermediate state can account for the various CNV possibilities. In another embodiment, the Hidden Markov Model is used to filter the output by examination of measured insert-sizes of reads near a detected feature's breakpoint(s). Other models or algorithms useful in the methods of the present invention include sequential search methods, genetic algorithms, estimation of distribution algorithms, random forest algorithms, weight vector of support vector machine algorithms, weights of logistic regression algorithms, and the like. Bioinformatics. 2007 Oct. 1; 23(19):2507-17 provides an overview of the relative merits of the algorithms or models provided above for the analysis of data. Illustrative algorithms include but are not limited to methods that reduce the number of variables such as principal component analysis algorithms, partial least squares methods, independent component analysis algorithms, methods that handle large numbers of variables directly such as statistical methods, and methods based on machine learning techniques. Statistical methods include penalized logistic regression, prediction analysis of microarrays (PAM), methods based on shrunken centroids, support vector machine analysis, and regularized linear discriminant analysis. Machine learning techniques include bagging procedures, boosting procedures, random forest algorithms, and combinations thereof. Cancer Inform. 2008; 6: 77-97 provides an overview of the techniques provided above for the analysis of data.

In some embodiments, an HMM-based detection algorithm can "segmentally" detect a large or substantially large CNV. In some cases, due to fluctuations in the coverage signal, there may be small detection gaps along the length of the true CNV. In an example, a 1 megabasepairs (Mbp) deletion may be detected as a small number of separate nominal detections, with small gaps between them. To mitigate this, a merge operation can be employed that identifies pairs of adjacent detections which are separated by a gap that is smaller than either of the two bracketing detections. The merge operation then measures the median coverage level in the gap. If the median coverage passes a predefined threshold, then the two detections are merged into a single large detection that spans the two original detections (including the enclosed detection gap). In an example, the true feature spans both detections, and the gap is a statistical artifact. Using real sequencing data of samples that are known to have large CNVs, this merge operation can permit a substantially better fidelity with respect to the true properties of the CNVs.

In some embodiments, the untargeted sequencing data (e.g., whole genome sequencing data) comprises paired-end reads. In some embodiments, the untargeted sequencing data (e.g., whole genome sequencing data) comprises mate-pair reads. The paired-end reads and/or the mate-pair reads may comprise insert-sizes greater than or equal to about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 30.0, 40.0, 50.0, 60.0, 70.0, 80.0, 90.0, or 100.0 kilobasepairs. In some embodiments, when paired-end reads and/or mate-pair reads are used, DNA or RNA molecules are digested into small inserts. The inserts may be ligated with adaptors on both ends. An insert-size may be the size of the DNA or RNA inserted between the adaptors. The adaptors may enable amplification and sequencing of the DNA or RNA. In an example, the paired-end reads may have an insert-size of larger than about 1 kilobasepairs. In another example, the mate-pair reads may have an insert-size of larger than about 2 kilobasepairs.

The paired-end reads and/or mate-pair reads may sequence 100 basepairs (bp) reads on both ends of the insert.

For example, when an untargeted sequencing data (e.g. whole genome sequencing data) is comprised of either paired-end reads with an insert size of larger than 1 kilobasepairs (kbp) or mate pairs with a separation of larger than 2 kbp, then even with low (~1×) read depth, there may be at least about 10 molecules spanning any particular position on the genome, which may be sufficient to provide corroborating evidence of large CNVs detected by methods and systems presented herein. In another example, methods and systems of the present disclosure, such as the HMM method, can be used to detect a 50 kbp heterozygous deletion. When paired-end reads are used, about half of the paired-end molecules that span the detection breakpoints may have insert-sizes that are 50 kbp larger than normal. The insert-sizes may appear larger because they may be mapped to a reference with the sequence segment that is deleted in the sample. In some examples, when 1 kbp insert sizes are used, then 10 reads span the breakpoint, 5 of which can have anomalous insert size. Five reads may provide sufficient statistical power and information to generate accurate and/or reliable results. In some cases, if an insert-size of only about 300 basepairs is used, then there may be only about 3 reads that span the breakpoint on average, and half of that may be about 1 read, which may not provide sufficient statistical power and information to generate accurate and/or reliable results.

Methods and systems provided herein may further include the use of a feature selection algorithm as provided herein. In some embodiments of the present invention, feature selection is provided by use of the LIMMA software package (Smyth, G. K. (2005). Limma: linear models for microarray data. In: *Bioinformatics and Computational Biology Solutions using R and Bioconductor*, R. Gentleman, V. Carey, S. Dudoit, R. Irizarry, W. Huber (eds.), Springer, New York, pages 397-420).

In some embodiments of the present invention, a diagonal linear discriminant analysis, k-nearest neighbor algorithm, support vector machine (SVM) algorithm, linear support vector machine, random forest algorithm, or a probabilistic model-based method or a combination thereof is provided for the detection of one or more genomic regions. In some embodiments, identified markers that distinguish samples (e.g., diseased versus normal) or distinguish genomic regions (e.g., copy number variation versus. normal) are selected based on statistical significance of the difference in expression levels between classes of interest. In some cases, the statistical significance is adjusted by applying a Benjamini Hochberg or another correction for false discovery rate (FDR).

In some cases, the algorithm may be supplemented with a meta-analysis approach such as that described by Fishel and Kaufman et al. 2007 *Bioinformatics* 23(13): 1599-606. In some cases, the algorithm may be supplemented with a meta-analysis approach such as a repeatability analysis. In some cases, the repeatability analysis selects markers that appear in at least one predictive expression product marker set.

A statistical evaluation of the detection of the genomic regions may provide a quantitative value or values indicative of one or more of the following: the likelihood of diagnostic accuracy; the likelihood of disorder, disease, condition and the like; the likelihood of a particular disorder, disease or condition; and the likelihood of the success of a particular therapeutic intervention. Thus, a physician, who is not likely to be trained in genetics or molecular biology, need not understand the raw data. Rather, the data is presented directly to the physician in the form of the quantitative values to guide patient care. The results can be statistically evaluated using a number of methods known to the art including, but not limited to: the student's T test, the two-sided T test, Pearson rank sum analysis, Hidden Markov Model Analysis, analysis of q-q plots, principal component analysis, one way ANOVA, two way ANOVA, LIMMA, and the like.

Polymorphisms

A polymorphism can include the occurrence of two or more genetically determined alternative sequences or alleles in a population. A polymorphic marker or site is the locus at which divergence occurs. Preferred markers have at least two alleles, each occurring at a frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include single nucleotide polymorphisms (SNP's) or single nucleotide variations, copy number variations (CNV's), restriction fragment length polymorphisms (RFLP's), short tandem repeats (STRs), variable number of tandem repeats (VNTR's), hypervariable regions, minisatellites, dinucleotide repeats, trinucleotide repeats, tetranucleotide repeats, simple sequence repeats, and insertion elements such as Alu. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

In some embodiments, polymorphisms are determined for one or more genes involved in one or more of different metabolic or signaling pathways. In some cases, the methods of the present invention provide for analysis of polymorphisms of at least one gene of 1, 2, 3, 4, 5, 6, 7, 9, 10, 11, 12, 13, 14, 15, 16, 17, 18, 19, 20, 25, 30, 35, 40, 45, 50, 55, 60, 65, 70, 75, 80, 85, 90, 95, 100 or more different metabolic or signaling pathways.

Methods and systems described herein can be used to discriminate and quantitate a genomic region containing a polymorphism. The methods described herein can discriminate and quantitate at least 1, 2, 3, 4, 5, 10, 20, 50, 100, 200, 500, 1,000, 2,000, 5,000, 10,000, 20,000, 50,000, 100,000, 200,000, 300,000, 400,000, 500,000, 600,000, 700,000, 800, 000, 900,000, 1,000,000, 2,000,000, 3,000,000 or more polymorphisms originating from one or more samples. In some embodiments, the methods described herein can discriminate and quantitate at least 1, 2, 3, 4, 5, 10, 20, 50, 100, 200, 500, 1,000, 2,000, 5,000, 10,000, 20,000, 50,000, 100,000, 200,000, 300,000, 400,000, 500,000, 600,000, 700, 000, 800,000, 900,000, 1,000,000, 2,000,000, 3,000,000, or more different polymorphic markers originating from one or more samples. In some embodiments, the methods described herein can discriminate and quantitate at least 1, 2, 3, 4, 5, 10, 20, 50, 100, 200, 500, 1,000, 2,000, 5,000, 10,000, 20,000, 50,000, 100,000, 200,000, 300,000, 400,000, 500, 000, 600,000, 700,000, 800,000, 900,000, 1,000,000, 2,000, 000, 3,000,000, or more different SNPs originating from one or more samples.

In some embodiments, the methods described herein are used to detect and/or quantify genomic regions by mapping the region to the genome of a species. In some embodiments, the methods described herein can discriminate and quantitate a genomic region from a species. The methods described herein can discriminate and quantitate of at least 1, 2, 3, 4, 5, 10, 20, 50, 100, 200, 500, 1,000, 2,000, 5,000, 10,000, 20,000, 50,000, 100,000, 200,000, 300,000, 400,000, 500, 000, 600,000, 700,000, 800,000, 900,000, 1,000,000, 2,000,000, 3,000,000, or more genomic regions from a species.

Methods and systems described herein may comprise the detection of genetic variants. In some instances, at least about 2, at least about 3, at least about 4, at least about 5, at least about 10, at least about 15, at least about 20, at least about 30, at least about 40, at least about 50, at least about 100, at least about 200, at least about 300, at least about 400, at least about 500, at least about 600, at least about 700, at least about 800, at least about 900, or at least about 1000 genetic variants are detected in a single reaction. In another example, at least about 2000, at least about 5000, at least about 10000, at least about 15000, at least about 20000, at least about 30000, at least about 40000, at least about 50000, at least about 100000, at least about 200000, at least about 300000, at least about 400000, at least about 500000, at least about 600000, at least about 700000, at least about 800000, at least about 900000, or at least about 1000000 genetic variants are detected in a single reaction. De novo assembly comprising an N50 value or median of 50, 75, 100, 200, 300, 400, 500, 600, 700, 800, 900, 1000 kilobasepairs or more can be achieved using the methods and systems described herein. Genetic variants within these assembled sequences can be identified according to the methods of the invention.

In some cases, genomic analysis such as sequencing may be performed in combination with any of the other methods described herein. For example, a sample may be obtained, tested for adequacy, and divided into aliquots or subsets of nucleic acid sample. One or more subsets of nucleic acid sample may then be used for target-specific sequencing of the present invention, and one or more may be used for low coverage whole genome sequencing methods of the present invention. It is further understood that the present invention anticipates that one skilled in the art may wish to perform other analyses on the biological sample that are not explicitly provided herein.

Methods of Sequencing

The methods and systems as disclosed herein may comprise, or comprise the use of, data from one or more sequencing reactions on one or more nucleic acid molecules in a sample. The methods and systems disclosed herein may comprise data from 1 or more, 2 or more, 3 or more, 4 or more, 5 or more, 6 or more, 7 or more, 8 or more, 9 or more, 10 or more, 15 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, or 1000 or more sequencing reactions on one or more nucleic acid molecules in a sample. The sequencing reactions may be run simultaneously, sequentially, or a combination thereof. The sequencing reactions may comprise whole genome sequencing or whole exome sequencing or one or more additional sequencing methods. The sequencing reactions may comprise Maxim-Gilbert, chain-termination or high-throughput systems.

The methods and systems disclosed herein may comprise data from at least one long read sequencing reaction and at least one short read sequencing reaction. The long read sequencing reaction and/or short read sequencing reaction data may comprise at least a portion of a subset of nucleic acid molecules. The long read sequencing reaction and/or short read sequencing reaction data may comprise at least a portion of two or more subsets of nucleic acid molecules. Both a long read sequencing reaction and a short read sequencing reaction data may comprise at least a portion of one or more subsets of nucleic acid molecules.

Sequencing of the one or more nucleic acid molecules or subsets thereof may comprise at least about 1; 2; 3; 4; 5; 6; 7; 8; 9; 10; 15; 20; 25; 30; 35; 40; 45; 50; 60; 70; 80; 90; 100; 200; 300; 400; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 25,000; 50,000; 75,000; 100,000; 250,000; 500,000; 750,000; 10,000,000; 25,000,000; 50,000,000; 100,000,000; 250,000,000; 500,000,000; 750,000,000; 1,000,000,000 or more sequencing reads.

Sequencing data may comprise at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more bases or basepairs of one or more nucleic acid molecules. Sequencing data may comprise at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more consecutive bases or basepairs of one or more nucleic acid molecules.

Preferably, the sequencing data in the methods and systems of the invention can comprise at least about 30 basepairs, at least about 40 basepairs, at least about 50 basepairs, at least about 60 basepairs, at least about 70 basepairs, at least about 80 basepairs, at least about 90 basepairs, at least about 100 basepairs, at least about 110, at least about 120 basepairs per read, at least about 150 basepairs, at least about 200 basepairs, at least about 250 basepairs, at least about 300 basepairs, at least about 350 basepairs, at least about 400 basepairs, at least about 450 basepairs, at least about 500 basepairs, at least about 550 basepairs, at least about 600 basepairs, at least about 700 basepairs, at least about 800 basepairs, at least about 900 basepairs, or at least about 1,000 basepairs per read. Alternatively, the sequencing data in the methods and systems of the invention can comprise long sequencing reads. In some instances, the sequencing data used in the methods systems of the invention can comprise at least about 1,200 basepairs per read, at least about 1,500 basepairs per read, at least about 1,800 basepairs per read, at least about 2,000 basepairs per read, at least about 2,500 basepairs per read, at least about 3,000 basepairs per read, at least about 3,500 basepairs per read, at least about 4,000 basepairs per read, at least about 4,500 basepairs per read, at least about 5,000 basepairs per read, at least about 6,000 basepairs per read, at least about 7,000 basepairs per read, at least about 8,000 basepairs per read, at least about 9,000 basepairs per read, at least about 10,000 basepairs per read, 20,000 basepairs per read, 30,000 basepairs per read, 40,000 basepairs per read, 50,000 basepairs per read, 60,000 basepairs per read, 70,000 basepairs per read, 80,000 basepairs per read, 90,000 basepairs per read, or 100,000 basepairs per read.

High-throughput sequencing systems may allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120, at least 150, at least 200, at least 250, at least 300, at least 350, at least 400, at least 450, or at least 500 bases per read. Sequencing can be performed using the nucleic acids described herein, such as genomic DNA, cDNA derived from RNA transcripts or RNA as a template.

The methods and systems as described in the current invention may also comprise comprehensive and targeted RNA expression detection data. For example, the invention provides for data via whole transcriptome sequencing or amplification. Whole transcriptome sequencing or amplification allows one to determine the expression of all RNA molecules comprising messenger RNA (mRNA), ribosomal RNA (rRNA), transfer RNA (tRNA), and non-coding RNA. Targeted RNA sequencing or amplification captures sequences of RNA from a relevant subset of a transcriptome in order to view high interest genes.

Sequencing may be conducted by any method known in the art. Targeted sequencing methods can include enrichment or amplification of a region of interest in the nucleic acid such as one or more polymorphisms, sets of genes, or genomic regions prior to sequencing. The enrichment or the targeted sequencing can comprise the use of one or more non-random or specific primers to amplify, enrich, or detect the region of interest. The non-random primers can be any non-random primers that are known in the art. For example, without limitation, primers can target one or more genes, exons, untranslated regions, specific genomic regions or a combination thereof.

Untargeted sequencing methods can include the use of one or more random or non-specific primers to enrich or amplify sequences non-specifically. Random primers can be any random primers that are known in the art. A universal primer is an example of a random primer. Non-target specific primers can be an example of a random primer. Non-limiting examples of random primers include random hexamers or hexamers and anchored-dT primer. Enrichment or amplification using random primers prior to sequencing allow amplification of non-specific sequences evenly covering the entire sequence coverage in a nucleic acid sample.

DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used with methods of the present disclosure includes, for example, Helicos True Single Molecule Sequencing (tSMS) (Harris T. D. et al. (2008) Science 320:106-109). In the tSMS technique, a DNA sample is cleaved into template fragments of approximately 100 to 200 nucleotides in length, and a poly(A) sequence is subsequently added to the 3' end of each DNA template fragment. Each template fragment is labeled by the addition of a fluorescently labeled adenosine nucleotide. The DNA strands are then immobilized onto the surface of a flow cell, through hybridization with oligo-dT capture probes that are immobilized at specific sites on the surface of the flow cell. The sites can be at a density of about 100 million sites/cm.sup.2. The flow cell is then loaded into an instrument, e.g., HeliScope™ sequencer, and a laser illuminates the surface of the flow cell, revealing the position of each DNA template fragment. A CCD camera can map the position of the template fragments on the flow cell surface. The fluorescent label of each DNA template fragment is then cleaved and washed away.

The sequencing reaction begins by introducing a DNA polymerase and a fluorescently labeled nucleotide. The oligo-dT nucleic acid serves as a primer, and the polymerase incorporates the labeled nucleotides to the primer in a template directed manner. The polymerase and unincorporated nucleotides are then removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., and PNAS (USA), 100: 3960-3964 (2003). The contents of each of these references are incorporated by reference herein in its entirety.

An RNA sequence can also be detected by single molecule sequencing such as with the Helicos Direct RNA sequencing method, described in Fatih Ozsolak, et al., Direct RNA sequencing. Nature 461, 814-818. Total RNA or RNA fragments with natural poly(A) tails are introduced to poly (dT) coated flow cells in order to enable capture and sequencing of poly(A) RNA species. In situations where the RNA does not have a poly(A) tail, for example small sample species, a poly(A) polymerase is introduced to the RNA in order to generate a poly(A) tail so that the sample RNA may attach to the flow cells to enable capture and sequencing.

Another example of a DNA and RNA sequencing technique that can be used with methods of the present disclosure is 454 sequencing (Roche) (Margulies, M et al. 2005, Nature, 437, 376-380). 454 sequencing is a sequencing-by-synthesis technology that utilizes pyrosequencing. 454 sequencing of DNA involves two steps. In the first step, DNA is sheared into fragments of approximately 300-800 basepairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains a 5'-biotin tag. The fragments attached to the beads are PCR amplified within droplets of an oil-water emulsion, resulting in multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed. In another embodiment, pyrosequencing is used to measure gene expression. Pyrosequecing of RNA applies may be conducted similarly to pyrosequencing of DNA, and is accomplished by attaching partial rRNA gene sequences to microscopic beads and then placing the attachments into individual wells. The attached partial rRNA sequences are then amplified in order to determine the gene expression profile, as described in Sharon Marsh, Pyrosequencing® Protocols in Methods in Molecular Biology, Vol. 373, 15-23 (2007).

Another example of DNA and RNA detection techniques that may be used with methods of the present disclosure is SOLiD technology (Applied Biosystems). SOLiD technology systems is a ligation based sequencing technology that may be utilized to run massively parallel next generation sequencing of both DNA and RNA. In DNA SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In other embodiments, SOLiD Serial Analysis of Gene Expression (SAGE) is used to measure gene expression. Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the sequence of the multiple transcripts simultaneously. The expression pattern of any population of transcripts can be quantitatively evaluated by determining the abundance of individual tags, and identifying the gene corresponding to each tag. For more details see, for example, Velculescu et al., Science 270:484 487 (1995); and Velculescu et al., Cell 88:243 51 (1997), the contents of each of which are incorporated by reference herein in their entirety).

Other examples of nucleic acid (e.g., DNA or RNA) sequencing techniques that may be used with the methods of the present disclosure are provided in U.S. Patent Publication Nos. 2009/0026082, 2009/0127589, 2010/0035252, 2010/0137143, 2010/0188073, 2010/0197507, 2010/0282617, 2010/0300559), 2010/0300895, 2010/0301398, and 2010/0304982, the contents of each of which is incorporated by reference herein in its entirety. In an example, DNA is sheared into fragments of approximately 300-800 basepairs, and the fragments are blunt ended. Oligonucleotide adaptors are then ligated to the ends of the fragments.

The adaptors serve as primers for amplification and sequencing of the fragments. The fragments can be attached to a surface and are attached at a resolution such that the fragments are individually resolvable. Addition of one or more nucleotides releases a proton (H.sup.+), and the signal is detected and recorded by a sequencing instrument. The signal strength is proportional to the number of nucleotides incorporated.

Another example of a sequencing technology that can be used with methods of the present disclosure is Illumina sequencing, which is a polymerase-based sequence-by-synthesis that may be utilized to amplify DNA or RNA. Illumina sequencing for DNA is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 single-stranded DNA copies of of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed, and the incorporation, detection, and identification steps are repeated. When using Illumina sequencing to detect RNA, the same method applies except that RNA fragments are being isolated and amplified in order to determine the RNA expression profile of the sample. In some embodiments, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000. These machines use reversible terminator-based sequencing by synthesis chemistry. These machines can perform 200 billion or more DNA reads in eight days. Smaller systems may be utilized for performing runs within 3, 2, 1 days or less time. Short synthesis cycles may be used to minimize the time it takes to obtain sequencing results.

Another example of a sequencing technology that may be used with methods of the present disclosure includes the single molecule, real-time (SMRT) technology of Pacific Biosciences to sequence both DNA and RNA. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated. In order to sequence RNA, the DNA polymerase is replaced with a reverse transcriptase in the ZMW, and the process is followed accordingly.

Another example of a sequencing technique that can be used with methods of the present disclosure is nanopore sequencing (Soni G V and Meller, A Clin Chem 53: 1996-2001) (2007). A nanopore is a small hole, of the order of 1 nanometer in diameter. Immersion of a nanopore in a conducting fluid, and application of a potential across it, results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore may be used to determine the DNA sequence.

The next generation sequencing can comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 basepairs. Adaptors (Ad1) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adaptors (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that the adaptors bind each other and form the completed circular DNA template.

Another example of a sequencing technique that can be used with methods of the present disclosure involves using a chemical-sensitive field effect transistor (chemFET) or ion sensitive field effect transistor (ISFET) array to sequence a nucleic acid (for example, as described in US Patent Application Publication No. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the single nucleic acids can be amplified on the bead. The individual beads can then be transferred to individual reaction chambers on a chemFET array, with each chamber having a chemFET sensor, and the nucleic acids can be sequenced.

Another example of a sequencing technique that can be used with methods of the present disclosure involves using an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to determine sequence identities.

Exemplary methods for calling variations in a polynucleotide sequence compared to a reference polynucleotide sequence and for polynucleotide sequence assembly (or reassembly), for example, are provided in U.S. patent publication No. 2011-0004413, (application Ser. No. 12/770, 089) which is incorporated herein by reference in its entirety for all purposes. See also Drmanac et al., Science 327, 78-81, 2010. Also incorporated by reference in their entirety and for all purposes are copending related application No. 61/623,876, entitled "Identification Of DNA Fragments And Structural Variations" and Ser. No. 13/447,087, entitled "Processing and Analysis of Complex Nucleic Acid Sequence Data." Other methods of sequencing or sample processing are described in PCT application No. WO2012142611 A2, hereby incorporated by reference in its entirety.

Assays

In some embodiments, the nucleic acid sample described herein can be subjected to varieties of assays. Assays may include, but are not limited to, sequencing, amplification, hybridization, enrichment, isolation, elution, fragmentation, detection, and quantification of one or more nucleic acid molecules. Assays may include methods for preparing one or more nucleic acid molecules.

In some embodiments, the nucleic acids in the nucleic acid sample described herein can be amplified. Amplification can be performed at any point during a multi reaction procedure using the methods and systems of the invention, e.g., before or after pooling of sequencing libraries from independent reaction volumes and may be used to amplify any suitable target molecule described herein.

Amplification can be performed by any methods or systems known in the art. The nucleic acids may be amplified by polymerase chain reaction (PCR), as described in, for example, U.S. Pat. Nos. 5,928,907 and 6,015,674, hereby incorporated by reference for any purpose. Other methods of nucleic acid amplification may include, for example, ligase chain reaction, oligonucleotide ligations assay, and hybridization assay, as described in greater detail in U.S. Pat. Nos. 5,928,907 and 6,015,674, incorporated by reference in their entirety. Real-time optical detection systems are also known in the art, as also described in greater detail in, for example, U.S. Pat. Nos. 5,928,907 and 6,015,674, incorporated herein above. Other amplification methods that can be used herein include those described in U.S. Pat. Nos. 5,242,794; 5,494, 810; 4,988,617; and 6,582,938, all of which are incorporated herein in their entirety. Other amplification techniques that can be used with methods of the present disclosure can include, e.g., AFLP (amplified fragment length polymorphism) PCR (see e.g.: Vos et al. 1995. AFLP: a new technique for DNA fingerprinting. Nucleic Acids Research 23: 4407-14), allele-specific PCR (see e.g., Saiki R K, Bugawan T L, Horn G T, Mullis K B, Erlich H A (1986). Analysis of enzymatically amplified beta-globin and HLA-DQ alpha DNA with allele-specific oligonucleotide probes Nature 324: 163-166), Alu PCR, assembly PCR (see e.g., Stemmer W P, Crameri A, Ha K D, Brennan T M, Heyneker H L (1995). Single-step assembly of a gene and entire plasmid from large numbers of oligodeoxyribonucleotides Gene 164: 49-53), assymetric PCR (see e.g., Saiki R K supra), colony PCR, helicase dependent PCR (see e.g., Myriam Vincent, Yan Xu and Huimin Kong (2004). Helicase-dependent isothermal DNA amplification EMBO reports 5 (8): 795-800), hot start PCR, inverse PCR (see e.g., Ochman H, Gerber A S, Hartl D L. Genetics. 1988 November; 120(3):621-3), in situ PCR, intersequence-specific PCR or IS SR PCR, digital PCR, linear-after-the-exponential-PCR or Late PCR (see e.g., Pierce K E and Wangh L T (2007). Linear-after-the-exponential polymerase chain reaction and allied technologies Real-time detection strategies for rapid, reliable diagnosis from single cells (Methods Mol. Med. 132: 65-85), long PCR, nested PCR, real-time PCR, duplex PCR, multiplex PCR, quantitative PCR, quantitative fluorescent PCR (QF-PCR), multiplex fluorescent PCR (MF-PCR), restriction fragment length polymorphism PCR (PCR-RFLP), PCK-RFLPIRT-PCR-IRFLP, polony PCR, in situ rolling circle amplification (RCA), bridge PCR, picotiter PCR, and emulsion PCR, or single cell PCR. Other suitable amplification methods can include transcription amplification, self-sustained sequence replication, selective amplification of target polynucleotide sequences, consensus sequence primed polymerase chain reaction (CP-PCR), arbitrarily primed polymerase chain reaction (AP-PCR), and degenerate oligonucleotide-primed PCR (DOP-PCR). Another method for achieving the result of an amplification of nucleic acids is known as the ligase chain reaction (LCR), nucleic acid sequence based amplification (NASBA), Q-beta-replicase method, 3SR (see for example Fahy et al. PCR Methods Appl. 1:25-33 (1991)), or Transcription Mediated Amplification (TMA) used by Gen-Probe. TMA is similar to NASBA in utilizing two enzymes in a self-sustained sequence replication. See U.S. Pat. No. 5,299,491 herein incorporated by reference. Other methods for amplification of nucleic acids can include Strand Displacement Amplification (SDA) (Westin et al 2000, Nature Biotechnology, 18, 199-202; Walker et al 1992, Nucleic Acids Research, 20, 7, 1691-1696), or Rolling Circle Amplification (RCA) (Lizardi et al. 1998, Nature Genetics, 19:225-232).

In some embodiments, amplification methods can be solid-phase amplification, polony amplification, colony amplification, emulsion PCR, bead RCA, surface RCA, surface SDA, etc., as may be recognized by one of ordinary skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20): E87) can be used. In some cases the methods of the invention can create a "polymerase colony technology," or "polony." referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). The methods of the invention provide new methods for generating and using polonies.

Amplification may be achieved through any process by which the copy number of a target sequence is increased, e.g., PCR. Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g., adaptor fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 50, or more cycles.

The methods disclosed herein may further comprise conducting one or more hybridization reactions on one or more nucleic acid molecules in a sample. The hybridization reactions may comprise the hybridization of one or more capture probes to one or more nucleic acid molecules in a sample or subset of nucleic acid molecules. The hybridization reactions may comprise hybridizing one or more capture probe sets to one or more nucleic acid molecules in a sample or subset of nucleic acid molecules. The hybridization reactions may comprise one or more hybridization arrays, multiplex hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof. The hybridization reaction may comprise one or more capture probes, one or more beads, one or more labels, one or more subsets of nucleic acid molecules, one or more nucleic acid samples, one or more reagents, one or more wash buffers, one or more elution buffers, one or more hybridization buffers, one or more hybridization chambers, one or more incubators, one or more separators, or a combination thereof.

The methods disclosed herein may further comprise conducting one or more enrichment reactions on one or more nucleic acid molecules in a sample. The enrichment reactions may comprise contacting a sample with one or more beads or bead sets. The enrichment reaction may comprise differential amplification of two or more subsets of nucleic acid molecules based on one or more genomic region features. For example, the enrichment reaction comprises differential amplification of two or more subsets of nucleic acid molecules based on GC content. Alternatively, or additionally, the enrichment reaction comprises differential amplification of two or more subsets of nucleic acid molecules based on methylation state. The enrichment reactions may comprise one or more hybridization reactions. The enrichment reactions may further comprise isolation and/or purification of one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. Alternatively, or additionally, the enrichment reaction may comprise enriching for one or more cell types in the sample. The one or more cell types may be enriched by flow cytometry.

Figure 2:
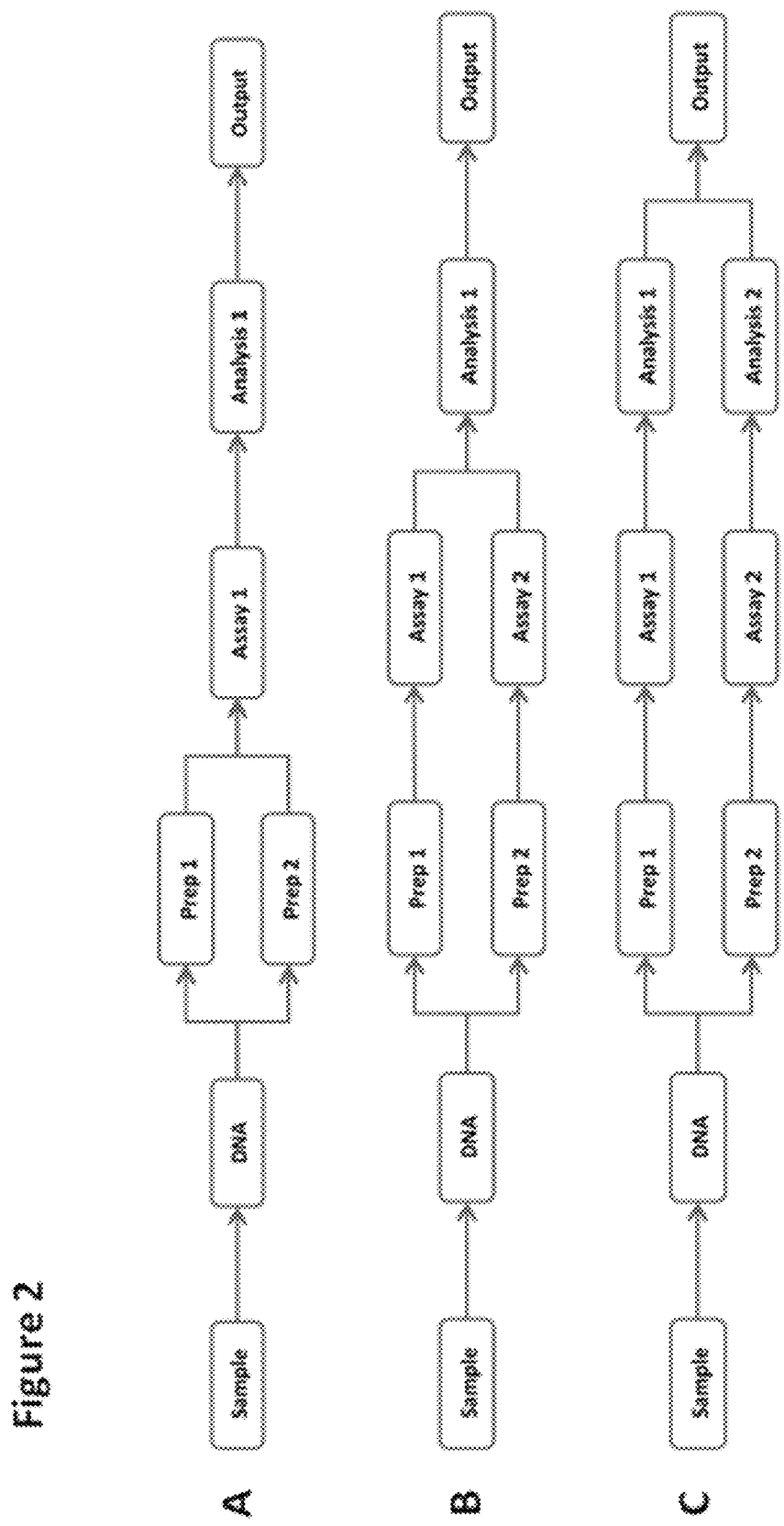
FIG. 2 depicts a schematic of four workflows of the present disclosure. "Prep 1" and "Prep 2" refer to subsets of nucleic acid molecules; "Assay 1" and "Assay 2" refer to assays.

As shown in FIG. 2, these protocols for work flow may involve enrichment for different genomic or non-genomic regions and comprise one or more different amplification steps to prepare libraries of nucleic acid molecules for assay. Some of these libraries may combine (2) for assay. Results of some assays may be combined (3) for subsequent analysis. Variant calls or other assessments of sequence or genetic state may be further combined (4) to produce a combined assessment at each locus addressed by the assay.

The one or more enrichment reactions may produce one or more enriched nucleic acid molecules. The enriched nucleic acid molecules may comprise a nucleic acid molecule or variant or derivative thereof. For example, the enriched nucleic acid molecules comprise one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. The enriched nucleic acid molecules may be differentiated from non-enriched nucleic acid molecules by GC content, molecular size, genomic regions, genomic region features, or a combination thereof. The enriched nucleic acid molecules may be derived from one or more assays, supernatants, eluents, or a combination thereof. The enriched nucleic acid molecules may differ from the non-enriched nucleic acid molecules by mean size, mean GC content, genomic regions, or a combination thereof.

The methods disclosed herein may further comprise conducting one or more isolation or purification reactions on one or more nucleic acid molecules in a sample. The isolation or purification reactions may comprise contacting a sample with one or more beads or bead sets. The isolation or purification reaction may comprise one or more hybridization reactions, enrichment reactions, amplification reactions, sequencing reactions, or a combination thereof. The isolation or purification reaction may comprise the use of one or more separators. The one or more separators may comprise a magnetic separator. The isolation or purification reaction may comprise separating bead bound nucleic acid molecules from bead free nucleic acid molecules. The isolation or purification reaction may comprise separating capture probe hybridized nucleic acid molecules from capture probe free nucleic acid molecules. The isolation or purification reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

The methods disclosed herein may further comprise conducting one or more elution reactions on one or more nucleic acid molecules in a sample. The elution reactions may comprise contacting a sample with one or more beads or bead sets. The elution reaction may comprise separating bead bound nucleic acid molecules from bead free nucleic acid molecules. The elution reaction may comprise separating capture probe hybridized nucleic acid molecules from capture probe free nucleic acid molecules. The elution reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

The methods disclosed herein may further comprise one or more fragmentation reactions. The fragmentation reactions may comprise fragmenting one or more nucleic acid molecules in a sample or subset of nucleic acid molecules to produce one or more fragmented nucleic acid molecules. The one or more nucleic acid molecules may be fragmented by sonication, needle shear, nebulization, shearing (e.g., acoustic shearing, mechanical shearing, point-sink shearing), passage through a French pressure cell, or enzymatic digestion. Enzymatic digestion may occur by nuclease digestion (e.g., micrococcal nuclease digestion, endonucleases, exonucleases, RNAse H or DNase I). Fragmentation of the one or more nucleic acid molecules may result in fragment sized of about 100 basepairs to about 2000 basepairs, about 200 basepairs to about 1500 basepairs, about 200 basepairs to about 1000 basepairs, about 200 basepairs to about 500 basepairs, about 500 basepairs to about 1500 basepairs, and about 500 basepairs to about 1000 basepairs. The one or more fragmentation reactions may result in fragment sized of about 50 basepairs to about 1000 basepairs. The one or more fragmentation reactions may result in fragment sized of about 100 basepairs, 150 basepairs, 200 basepairs, 250 basepairs, 300 basepairs, 350 basepairs, 400 basepairs, 450 basepairs, 500 basepairs, 550 basepairs, 600 basepairs, 650 basepairs, 700 basepairs, 750 basepairs, 800 basepairs, 850 basepairs, 900 basepairs, 950 basepairs, 1000 basepairs or more.

Fragmenting the one or more nucleic acid molecules may comprise mechanical shearing of the one or more nucleic acid molecules in the sample for a period of time. The fragmentation reaction may occur for at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more seconds.

Fragmenting the one or more nucleic acid molecules may comprise contacting a nucleic acid sample with one or more beads. Fragmenting the one or more nucleic acid molecules may comprise contacting the nucleic acid sample with a plurality of beads, wherein the ratio of the volume of the plurality of beads to the volume of nucleic acid sample is about 0.10, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00 or more. Fragmenting the one or more nucleic acid molecules may comprise contacting the nucleic acid sample with a plurality of beads, wherein the ratio of the volume of the plurality of beads to the volume of nucleic acid is about 2.00, 1.90, 1.80, 1.70, 1.60, 1.50, 1.40, 1.30, 1.20, 1.10, 1.00, 0.90, 0.80, 0.70, 0.60, 0.50, 0.40, 0.30, 0.20, 0.10, 0.05, 0.04, 0.03, 0.02, 0.01 or less.

The methods disclosed herein may further comprise conducting one or more detection reactions on one or more nucleic acid molecules in a sample. Detection reactions may comprise one or more sequencing reactions. Alternatively, conducting a detection reaction comprises optical sensing, electrical sensing, or a combination thereof. Optical sensing may comprise optical sensing of a photoilluminscence photon emission, fluorescence photon emission, pyrophosphate photon emission, chemiluminescence photon emission, or a combination thereof. Electrical sensing may comprise electrical sensing of an ion concentration, ion current modulation, nucleotide electrical field, nucleotide tunneling current, or a combination thereof.

The methods disclosed herein may further comprise conducting one or more quantification reactions on one or more nucleic acid molecules in a sample. Quantification reactions may comprise sequencing, PCR, qPCR, digital PCR, or a combination thereof.

The methods disclosed herein may further comprise conducting 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, or 50 or more assays on a sample comprising one or more nucleic acid molecules. The two or more assays may be different, similar, identical, or a combination thereof. For example, The methods disclosed herein comprise conducting two or more sequencing reactions. In another example, The methods disclosed herein comprise conducting two or more assays, wherein at least one of the two or more assays comprises a sequencing reaction. In yet another example, The methods disclosed herein comprise conducting two or more assays, wherein at least two of the two or more assays comprises a sequencing reaction and a hybridization reaction. The two or more assays may be performed sequentially, simultaneously, or a combination thereof. For example, the two or more sequencing reactions may be performed simultaneously. In another example, the methods disclosed herein comprise conducting a hybridization reaction, followed by a sequencing reaction. In yet another example, the methods disclosed herein comprise conducting two or more hybridization reactions simultaneously, followed by conducting two or more sequencing reactions simultaneously. The two or more assays may be performed by one or more devices. For example, two or more amplification reactions may be performed by a PCR machine. In another example, two or more sequencing reactions may be performed by two or more sequencers.

Devices

The methods and systems disclosed herein may comprise one or more devices. The methods and systems disclosed herein may comprise the use of one or more devices to perform one or more steps or assays comprised therein. The methods and systems disclosed herein may comprise one or more devices and the use thereof in one or more steps or assays. For example, conducting a sequencing reaction may comprise one or more sequencers. In another example, combining a plurality of data inputs and generating a combined data may comprise the use of one or more computer processors. In yet another example, one or more processors may be used in the generating and displaying electronically at least a portion of the data output. Exemplary devices include, but are not limited to, sequencers, computer processors, computer display, monitors, hard drives, thermocyclers, real-time PCR instruments, magnetic separators, transmission devices, hybridization chambers, electrophoresis apparatus, centrifuges, microscopes, imagers, fluorometers, luminometers, plate readers, computers, processors, and bioanalyzers.

The methods disclosed herein may comprise one or more sequencers. The one or more sequencers may comprise one or more HiSeq, MiSeq, HiScan, Genome Analyzer IIx, SOLiD Sequencer, Ion Torrent PGM, 454 GS Junior, Pac Bio RS, or a combination thereof. The one or more sequencers may comprise one or more sequencing platforms. The one or more sequencing platforms may comprise GS FLX by 454 Life Technologies/Roche, Genome Analyzer by Solexa/Illumina, SOLiD by Applied Biosystems, CGA Platform by Complete Genomics, PacBio RS by Pacific Biosciences, or a combination thereof.

The methods disclosed herein may comprise one or more thermocyclers. The one or more thermocyclers may be used to amplify one or more nucleic acid molecules. The methods disclosed herein may comprise one or more real-time PCR instruments. The one or more real-time PCR instruments may comprise a thermal cycler and a fluorometer. The one or more thermocyclers may be used to amplify and detect one or more nucleic acid molecules.

The methods disclosed herein may comprise one or more magnetic separators. The one or more magnetic separators may be used for separation of paramagnetic and ferromagnetic particles from a suspension. The one or more magnetic separators may comprise one or more LifeStep™ biomagnetic separators, SPHERO™ FlexiMag separator, SPHERO™ MicroMag separator, SPHERO™ HandiMag separator, SPHERO™ MiniTube Mag separator, SPHERO™ UltraMag separator, DynaMag™ magnet, DynaMag™-2 Magnet, or a combination thereof.

The methods disclosed herein may comprise one or more bioanalyzers. Generaly, a bioanalyzer is a chip-based capillary electrophoresis machine that can analyse RNA, DNA, and proteins. The one or more bioanalyzers may comprise Agilent's 2100 Bioanalyzer.

Computer Systems

FIG. 1 shows a computer system (also "system" herein) 101 programmed or otherwise configured to implement the methods of the disclosure, such as receiving and/or combining sequencing data and/or annotating sequencing data. The system 101 includes a central processing unit (CPU, also "processor" and "computer processor" herein) 105, which can be a single core or multi core processor, or a plurality of processors for parallel processing. The system 101 also includes memory 110 (e.g., random-access memory, read-only memory, flash memory), electronic storage unit 115 (e.g., hard disk), communications interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communications bus (solid lines), such as a motherboard. The storage unit 115 can be a data storage unit (or data repository) for storing data. The system 101 is operatively coupled to a computer network ("network") 130 with the aid of the communications interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130 in some cases, with the aid of the system 101, can implement a peer-to-peer network, which may enable devices coupled to the system 101 to behave as a client or a server.

The system 101 is in communication with a processing system 135. The processing system 135 can be configured to implement the methods disclosed herein, such as sequencing a nucleic acid sample or portion thereof. In some examples, the processing system 135 is a nucleic acid sequencing system, such as, for example, a next generation sequencing system (e.g., Illumina sequencer, Ion Torrent sequencer, Pacific Biosciences sequencer, Oxford Nanopore Technologies). The processing system 135 can be in communication with the system 101 through the network 130, or by direct (e.g., wired, wireless) connection. The processing system 135 can be configured for analysis, such as nucleic acid sequence analysis.

Methods and systems as described herein can be implemented by way of machine (or computer processor) executable code (or software) stored on an electronic storage location of the system 101, such as, for example, on the memory 110 or electronic storage unit 115. During use, the code can be executed by the processor 105. In some examples, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display that comprises a user interface (UI) for providing, for example, operational parameters of a charging station, and/or electric vehicle. Examples of UI's include, without limitation, a graphical user interface (GUI) and web-based user interface.

In some embodiments, the system 101 includes a display to provide visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the system 101 includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

The system 101 can include or be operably coupled to one or more databases. The databases may comprise genomic, proteomic, pharmacogenomic, biomedical, and scientific databases. The databases may be publicly available databases. Alternatively, or additionally, the databases may comprise proprietary databases. The databases may be commercially available databases. The databases include, but are not limited to, MendelDB, PharmGKB, Varimed, Regulome, curated BreakSeq junctions, Online Mendelian Inheritance in Man (OMIM), Human Genome Mutation Database (HGMD), NCBI dbSNP, NCBI RefSeq, GENCODE, GO (gene ontology), and Kyoto Encyclopedia of Genes and Genomes (KEGG).

The methods disclosed herein may comprise analyzing one or more databases. The methods disclosed herein may comprise analyzing at least about 1, 2, 3, 4, 5, 6, 7, 8, 9, 10, 11, 12, 13, 14, 15, 16, 17, 18, 19, 20, 30 or more databases. Analyzing the one or more databases may comprise one or more algorithms, computers, processors, memory locations, devices, or a combination thereof.

The methods disclosed herein may comprise producing one or more probes based on data and/or information from one or more databases. The methods disclosed herein may comprise producing one or more probe sets based on data and/or information from one or more databases. The methods disclosed herein may comprise producing one or more probes and/or probe sets based on data and/or information from at least about 2 or more databases. The methods disclosed herein may comprise producing one or more probes and/or probe sets based on data and/or information from at least about 3 or more databases. The methods disclosed herein may comprise producing one or more probes and/or probe sets based on data and/or information from at least about 4, 5, 6, 7, 8, 9, 10, 11, 12, 13, 14, 15, 16, 17, 18, 19, 20, 30 or more databases.

The methods disclosed herein may comprise identifying one or more nucleic acid regions based on data and/or information from one or more databases. The methods disclosed herein may comprise identifying one or more sets of nucleic acid regions based on data and/or information from one or more databases. The methods disclosed herein may comprise identifying one or more nucleic acid regions and/or sets of nucleic acid regions based on data and/or information from at least about 2 or more databases. The methods disclosed herein may comprise identifying one or more nucleic acid regions and/or sets of nucleic acid regions based on data and/or information from at least about 3 or more databases. The methods disclosed herein may comprise identifying one or more nucleic acid regions and/or sets of nucleic acid regions based on data and/or information from at least about 4, 5, 6, 7, 8, 9, 10, 11, 12, 13, 14, 15, 16, 17, 18, 19, 20, 30 or more databases. The methods disclosed herein may further comprise producing one or more probes and/or probe sets based on the identification of the one or more nucleic acid regions and/or sets of nucleic acid regions.

The methods disclosed herein may comprise analyzing one or more results based on data and/or information from one or more databases. The methods disclosed herein may comprise analyzing one or more sets of results based on data and/or information from one or more databases. The methods disclosed herein may comprise analyzing one or more combined results based on data and/or information from one or more databases. The methods disclosed herein may comprise analyzing one or more results, sets of results, and/or combined results based on data and/or information from at least about 2 or more databases. The methods disclosed herein may comprise analyzing one or more results, sets of results, and/or combined results based on data and/or information from at least about 3 or more databases. The methods disclosed herein may comprise analyzing one or more results, sets of results, and/or combined results based on data and/or information from at least about 4, 5, 6, 7, 8, 9, 10, 11, 12, 13, 14, 15, 16, 17, 18, 19, 20, 30 or more databases.

The methods disclosed herein may comprise comparing one or more results based on data and/or information from one or more databases. The methods disclosed herein may comprise comparing one or more sets of results based on data and/or information from one or more databases. The methods disclosed herein may comprise comparing one or more combined results based on data and/or information from one or more databases. The methods disclosed herein may comprise comparing one or more results, sets of results, and/or combined results based on data and/or information from at least about 2 or more databases. The methods disclosed herein may comprise comparing one or more results, sets of results, and/or combined results based on data and/or information from at least about 3 or more databases. The methods disclosed herein may comprise comparing one or more results, sets of results, and/or combined results based on data and/or information from at least about 4, 5, 6, 7, 8, 9, 10, 11, 12, 13, 14, 15, 16, 17, 18, 19, 20, 30 or more databases.

The methods disclosed herein may comprise biomedical databases, genomic databases, biomedical reports, disease reports, case-control analysis, and rare variant discovery analysis based on data and/or information from one or more databases, one or more assays, one or more data or results, one or more outputs based on or derived from one or more assays, one or more outputs based on or derived from one or more data or results, or a combination thereof.

Analysis

The systems and methods as disclosed herein may comprise, or comprise the use of, one or more data, one or more data sets, one or more combined data, one or more combined data sets, one or more results, one or more sets of results, one or more combined results, or a combination thereof. The data and/or results may be based on or derived from one or more assays, one or more databases, or a combination thereof. The methods and systems as disclosed herein may comprise, or comprise the use of, analysis of the one or more data, one or more data sets, one or more combined data, one or more combined data sets, one or more results, one or more sets of results, one or more combined results, or a combination thereof. The methods and systems as disclosed herein may comprise, or comprise the use of, processing of the one or more data, one or more data sets, one or more combined data, one or more combined data sets, one or more results, one or more sets of results, one or more combined results, or a combination thereof.

The systems and methods as disclosed herein may comprise, or comprise the use of, at least one analysis and at least one processing of the one or more data, one or more data sets, one or more combined data, one or more combined data sets, one or more results, one or more sets of results, one or more combined results, or a combination thereof. The methods and systems as disclosed herein may comprise, or comprise the use of, one or more analyses and one or more processing of the one or more data, one or more data sets, one or more combined data, one or more combined data sets, one or more results, one or more sets of results, one or more combined results, or a combination thereof. The methods and systems as disclosed herein may comprise, or comprise the use of, at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct analyses of the one or more data, one or more data sets, one or more combined data, one or more combined data sets, one or more results, one or more sets of results, one or more combined results, or a combination thereof. The methods and systems as disclosed herein may comprise, or comprise the use of, at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct processing of the one or more data, one or more data sets, one or more combined data, one or more combined data sets, one or more results, one or more sets of results, one or more combined results, or a combination thereof. The one or more analyses and/or one or more processing may occur simultaneously, sequentially, or a combination thereof.

The one or more analyses and/or one or more processing may occur over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more year period.

The methods and systems as disclosed herein may comprise, or comprise the use of, one or more data. The one or more data may comprise one or more raw data based on or derived from one or more assays. The one or more data may comprise one or more raw data based on or derived from one or more databases. The one or more data may comprise at least partially analyzed data based on or derived from one or more raw data. The one or more data may comprise at least partially processed data based on or derived from one or more raw data. The one or more data may comprise fully analyzed data based on or derived from one or more raw data. The one or more data may comprise fully processed data based on or derived from one or more raw data. The data may comprise sequencing read data or expression data. The data may comprise biomedical, scientific, pharmacological, and/or genetic information.

The methods and systems as disclosed herein may comprise, or comprise the use of, one or more combined data. The one or more combined data may comprise two or more data. The one or more combined data may comprise two or more data sets. The one or more combined data may comprise one or more raw data based on or derived from one or more assays. The one or more combined data may comprise one or more raw data based on or derived from one or more databases. The one or more combined data may comprise at least partially analyzed data based on or derived from one or more raw data. The one or more combined data may comprise at least partially processed data based on or derived from one or more raw data. The one or more combined data may comprise fully analyzed data based on or derived from one or more raw data. The one or more combined data may comprise fully processed data based on or derived from one or more raw data. One or more combined data may comprise sequencing read data or expression data. One or more combined data may comprise biomedical, scientific, pharmacological, and/or genetic information.

The methods and systems as disclosed herein may comprise, or comprise the use of, one or more data sets. The one or more data sets may comprise one or more data. The one or more data sets may comprise one or more combined data. The one or more data sets may comprise one or more raw data based on or derived from one or more assays. The one or more data sets may comprise one or more raw data based on or derived from one or more databases. The one or more data sets may comprise at least partially analyzed data based on or derived from one or more raw data. The one or more data sets may comprise at least partially processed data based on or derived from one or more raw data. The one or more data sets may comprise fully analyzed data based on or derived from one or more raw data. The one or more data sets may comprise fully processed data based on or derived from one or more raw data. The data sets may comprise sequencing read data or expression data. The data sets may comprise biomedical, scientific, pharmacological, and/or genetic information.

The methods and systems as disclosed herein may comprise, or comprise the use of, one or more combined data sets. The one or more combined data sets may comprise two or more data. The one or more combined data sets may comprise two or more combined data. The one or more combined data sets may comprise two or more data sets. The one or more combined data sets may comprise one or more raw data based on or derived from one or more assays. The one or more combined data sets may comprise one or more raw data based on or derived from one or more databases. The one or more combined data sets may comprise at least partially analyzed data based on or derived from one or more raw data. The one or more combined data sets may comprise at least partially processed data based on or derived from one or more raw data. The one or more combined data sets may comprise fully analyzed data based on or derived from one or more raw data. The one or more combined data sets may comprise fully processed data based on or derived from one or more raw data. The methods and systems as disclosed herein may further comprise further processing and/or analysis of the combined data sets. One or more combined data sets may comprise sequencing read data or expression data. One or more combined data sets may comprise biomedical, scientific, pharmacological, and/or genetic information.

The methods and systems as disclosed herein may comprise, or comprise the use of, one or more results. The one or more results may comprise one or more data, data sets, combined data, and/or combined data sets. The one or more results may be based on or derived from one or more data, data sets, combined data, and/or combined data sets. The one or more results may be produced from one or more assays. The one or more results may be based on or derived from one or more assays. The one or more results may be based on or derived from one or more databases. The one or more results may comprise at least partially analyzed results based on or derived from one or more data, data sets, combined data, and/or combined data sets. The one or more results may comprise at least partially processed results based on or derived from one or more data, data sets, combined data, and/or combined data sets. The one or more results may comprise fully analyzed results based on or derived from one or more data, data sets, combined data, and/or combined data sets. The one or more results may comprise fully processed results based on or derived from one or more data, data sets, combined data, and/or combined data sets. The results may comprise sequencing read data or expression data. The results may comprise biomedical, scientific, pharmacological, and/or genetic information.

The methods and systems as disclosed herein may comprise, or comprise the use of, one or more sets of results. The one or more sets of results may comprise one or more data, data sets, combined data, and/or combined data sets. The one or more sets of results may be based on or derived from one or more data, data sets, combined data, and/or combined data sets. The one or more sets of results may be produced from one or more assays. The one or more sets of results may be based on or derived from one or more assays. The one or more sets of results may be based on or derived from one or more databases. The one or more sets of results may comprise at least partially analyzed sets of results based on or derived from one or more data, data sets, combined data, and/or combined data sets. The one or more sets of results may comprise at least partially processed sets of results based on or derived from one or more data, data sets, combined data, and/or combined data sets. The one or more sets of results may comprise at fully analyzed sets of results based on or derived from one or more data, data sets, combined data, and/or combined data sets. The one or more sets of results may comprise fully processed sets of results based on or derived from one or more data, data sets, combined data, and/or combined data sets. The sets of results may comprise sequencing read data or expression data. The sets of results may comprise biomedical, scientific, pharmacological, and/or genetic information.

The methods and systems as disclosed herein may comprise, or comprise the use of, one or more combined results. The combined results may comprise one or more results, sets of results, and/or combined sets of results. The combined results may be based on or derived from one or more results, sets of results, and/or combined sets of results. The one or more combined results may comprise one or more data, data sets, combined data, and/or combined data sets. The one or more combined results may be based on or derived from one or more data, data sets, combined data, and/or combined data sets. The one or more combined results may be produced from one or more assays. The one or more combined results may be based on or derived from one or more assays. The one or more combined results may be based on or derived from one or more databases. The one or more combined results may comprise at least partially analyzed combined results based on or derived from one or more data, data sets, combined data, and/or combined data sets. The one or more combined results may comprise at least partially processed combined results based on or derived from one or more data, data sets, combined data, and/or combined data sets. The one or more combined results may comprise fully analyzed combined results based on or derived from one or more data, data sets, combined data, and/or combined data sets. The one or more combined results may comprise fully processed combined results based on or derived from one or more data, data sets, combined data, and/or combined data sets. The combined results may comprise sequencing read data or expression data. The combined results may comprise biomedical, scientific, pharmacological, and/or genetic information.

The methods and systems as disclosed herein may comprise, or comprise the use of, one or more combined sets of results. The combined sets of results may comprise one or more results, sets of results, and/or combined results. The combined sets of results may be based on or derived from one or more results, sets of results, and/or combined results. The one or more combined sets of results may comprise one or more data, data sets, combined data, and/or combined data sets. The one or more combined sets of results may be based on or derived from one or more data, data sets, combined data, and/or combined data sets. The one or more combined sets of results may be produced from one or more assays. The one or more combined sets of results may be based on or derived from one or more assays. The one or more combined sets of results may be based on or derived from one or more databases. The one or more combined sets of results may comprise at least partially analyzed combined sets of results based on or derived from one or more data, data sets, combined data, and/or combined data sets. The one or more combined sets of results may comprise at least partially processed combined sets of results based on or derived from one or more data, data sets, combined data, and/or combined data sets. The one or more combined sets of results may comprise fully analyzed combined sets of results based on or derived from one or more data, data sets, combined data, and/or combined data sets. The one or more combined sets of results may comprise fully processed combined sets of results based on or derived from one or more data, data sets, combined data, and/or combined data sets. The combined sets of results may comprise sequencing read data or expression data. The combined sets of results may comprise biomedical, scientific, pharmacological, and/or genetic information.

The methods and systems as disclosed herein may comprise, or comprise the use of, one or more outputs, sets of outputs, combined outputs, and/or combined sets of outputs. The methods, libraries, kits, and systems herein may comprise producing one or more outputs, sets of outputs, combined outputs, and/or combined sets of outputs. The sets of outputs may comprise one or more outputs, one or more combined outputs, or a combination thereof. The combined outputs may comprise one or more outputs, one or more sets of outputs, one or more combined sets of outputs, or a combination thereof. The combined sets of outputs may comprise one or more outputs, one or more sets of outputs, one or more combined outputs, or a combination thereof. The one or more outputs, sets of outputs, combined outputs, and/or combined sets of outputs may be based on or derived from one or more data, one or more data sets, one or more combined data, one or more combined data sets, one or more results, one or more sets of results, one or more combined results, or a combination thereof. The one or more outputs, sets of outputs, combined outputs, and/or combined sets of outputs may be based on or derived from one or more databases. The one or more outputs, sets of outputs, combined outputs, and/or combined sets of outputs may comprise one or more biomedical reports, biomedical outputs, rare variant outputs, pharmacogenetic outputs, population study outputs, case-control outputs, biomedical databases, genomic databases, disease databases, net content.

The methods and systems as disclosed herein may comprise, or comprise the use of, one or more biomedical outputs, one or more sets of biomedical outputs, one or more combined biomedical outputs, one or more combined sets of biomedical outputs. The methods, libraries, kits and systems herein may comprise producing one or more biomedical outputs, one or more sets of biomedical outputs, one or more combined biomedical outputs, one or more combined sets of biomedical outputs. The sets of biomedical outputs may comprise one or more biomedical outputs, one or more combined biomedical outputs, or a combination thereof. The combined biomedical outputs may comprise one or more biomedical outputs, one or more sets of biomedical outputs, one or more combined sets of biomedical outputs, or a combination thereof. The combined sets of biomedical outputs may comprise one or more biomedical outputs, one or more sets of biomedical outputs, one or more combined biomedical outputs, or a combination thereof. The one or more biomedical outputs, one or more sets of biomedical outputs, one or more combined biomedical outputs, one or more combined sets of biomedical outputs may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, or a combination thereof. The one or more biomedical outputs may comprise biomedical information of a subject. The biomedical information of the subject may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

The methods and systems as disclosed herein may comprise, or comprise the use of, one or more biomedical reports. The methods, libraries, kits, and systems herein may comprise producing one or more biomedical reports. The one or more biomedical reports may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, one or more biomedical outputs, one or more sets of biomedical outputs, combined biomedical outputs, one or more sets of biomedical outputs, or a combination thereof. The biomedical report may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

The methods and systems as disclosed herein may also comprise, or comprise the use of, the transmission of one or more data, information, results, outputs, reports or a combination thereof. For example, data/information based on or derived from the one or more assays are transmitted to another device and/or instrument. In another example, the data, results, outputs, biomedical outputs, biomedical reports, or a combination thereof are transmitted to another device and/or instrument. The information obtained from an algorithm may also be transmitted to another device and/or instrument. Information based on the analysis of one or more databases may be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc). The data, results, outputs, biomedical outputs, biomedical reports can be transmitted to a patient and/or a healthcare provider.

Transmission may be based on the analysis of one or more data, results, information, databases, outputs, reports, or a combination thereof. For example, transmission of a second report is based on the analysis of a first report. Alternatively, transmission of a report is based on the analysis of one or more data or results. Transmission may be based on receiving one or more requests. For example, transmission of a report may be based on receiving a request from a user (e.g., patient, healthcare provider, individual).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibers, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

The methods and systems as disclosed herein may comprise, or comprise the use of, one or more sample identifiers. The sample identifiers may comprise labels, barcodes, and other indicators which can be linked to one or more samples and/or subsets of nucleic acid molecules. The methods disclosed herein may comprise one or more processors, one or more memory locations, one or more computers, one or more monitors, one or more computer software, one or more algorithms for linking data, results, outputs, biomedical outputs, and/or biomedical reports to a sample.

The methods and systems as disclosed herein may comprise, or comprise the use of, a processor for correlating the expression levels of one or more nucleic acid molecules with a prognosis of disease outcome. The methods disclosed herein may comprise one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can optionally further designate a treatment modality for a patient or class of patients.

In some cases at least a portion of the results or the outputs, are entered into a database for access by representatives or agents of a sequencing business, the individual, a medical provider, or insurance provider. In some cases outputs include polymorphism classification, identification, or diagnosis by a representative, agent or consultant of the business, such as a medical professional. In other cases, a computer or algorithmic analysis of the data is provided automatically. In some cases the sequencing business may bill the individual, insurance provider, medical provider, researcher, or government entity for one or more of the following: sequencing assays performed, consulting services, data analysis, reporting of results, or database access.

In some embodiments of the present invention, at least a portion of the output, or the combined data, is presented or displayed as a report on a computer screen or as a paper record. In some embodiments, the output is an electronic report. In some cases, the output is displayed in numeric and/or graphical form. For example without limitation, at least a portion of the output of the combined data is displayed on a graphical user interface of an electronic display coupled to the computer processor. In some cases, the output, display or report may include, but is not limited to, such information as one or more of the following: the number of copy number variation identified, the suitability of the original sample, the number of genes showing different polymorphisms, one or more haplotypes, a diagnosis, a statistical confidence for the diagnosis, the likelihood of a specific condition or disorder, and indicated therapies.

Performance

The methods and systems disclosed herein can detect one or more genomic regions (i.e., copy number variation, or one or more polymorphisms) with a specificity or sensitivity of about or greater than about 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, or 99.5%, or a positive predictive value or negative predictive value of about or at least about 80%, 85%, 90%, 95%, 95.5%, 96%, 96.5%, 97%, 97.5%, 98%, 98.5%, 99%, 99.5% or more. The methods and systems disclosed herein can detect one or more genomic regions (i.e., copy number variation, or one or more polymorphisms) with a specificity or sensitivity of about or greater than about 50%. The methods and systems disclosed herein can diagnose a specific condition based on the detected genomic regions such as copy number variation. The methods and systems can diagnose a specific condition with a specificity or sensitivity of greater than 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 80%, 85%, 90%, 95%, 95.5%, 96%, 96.5%, 97%, 97.5%, 98%, 98.5%, 99%, 99.5% or more.

The methods and systems disclosed herein may increase the sensitivity or specificity when compared to the sensitivity or specificity of current sequencing methods. For example without limitation, in some embodiments, the combined whole exome sequencing and a whole genome sequencing reactions may increase the sensitivity or specificity in detecting one or more copy number variations or diagnosing a specific condition when compared to the sensitivity or specificity of whole exome sequencing alone. The sensitivity or specificity of the methods and systems as described herein may increase by at least about 1%, 2%, 3%, 4%, 5%, 5.5%, 6%, 6.5%, 7%, 7.5%, 8%, 8.5%, 9%, 9.5%, 10%, 10.5%, 11%, 12%, 13%, 14%, 15%, 16%, 17%, 18%, 19%, 20%, 25%, 30%, 35%, 40%, 45%, 50%, 55%, 60%, 70%, 80%, 90%, 95%, 97% or more. The sensitivity or specificity of the methods and systems as described herein may increase by at least about 4.5-20%, about 5-15%, about 7%-12%, or about 8%-10%. In some embodiments, the methods and systems disclosed herein may have a similar sensitivity or specificity when compared to the sensitivity or specificity of a high coverage whole genome sequencing alone.

In some embodiments, the methods and systems as described herein comprise combining an untargeted sequencing data (e.g., low coverage whole genome sequencing data) and one or more target-specific sequencing data. The methods and system disclosed herein may have a sensitivity, specificity, positive predictive value or negative predictive value that is similar to a high coverage whole genome sequencing data alone. The sensitivity specificity, positive predictive value or negative predictive value may be for the detection of one or more haplotypes, SNV, CNV or one or more polymorphisms. In some embodiments, the methods and systems as disclosed herein comprising untargeted sequencing data (e.g., a low coverage whole genome sequencing data) that may have a sensitivity, specificity, positive predictive value or negative predictive value that is less than 5%, 10%, 15%, 20%, 25%, 30%, 35%, 40%, 45%, 50%, 55%, 60%, 65%, 70%, 75%, 80%, 85% or 90% for one or more SNV. In some embodiments, the methods and systems as disclosed herein may have a sensitivity, specificity, positive predictive value or negative predictive value that is less than 5%, 10%, 15%, 20%, 25%, 30%, 35%, 40%, 45%, 50%, 55%, 60%, 65%, 70%, 75%, 80%, 85% or 90% for one or more polymorphisms, specific genes or genomic regions. In some embodiments, the untargeted sequencing (e.g., whole genome sequencing) in the methods and systems as disclosed herein may have a sensitivity, specificity, positive predictive value or negative predictive value that is less than 5%, 10%, 15%, 20%, 25%, 30%, 35%, 40%, 45%, 50%, 55%, 60%, 65%, 70%, 75%, 80%, 85% or 90% for one or more SNV, one or more polymorphisms or one or more specific genes or genomic regions. In some embodiments, the target-specific sequencing data may have a sensitivity, specificity, positive predictive value or negative predictive value that is about, at least about or less than about 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, 99.5% or 100%. In some cases, the untargeted sequencing can have a sensitivity, specificity, positive predictive value or negative predictive value that is between about 50% to 80%.

The methods and systems disclosed herein can detect one or more genomic regions (i.e., copy number variation, or one or more polymorphisms) with an error rate of less than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10% or less. The methods and systems disclosed herein can diagnose a specific condition based on the detected genomic regions such as copy number variation. The methods and systems can diagnose a specific condition with a a error rate of less than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10% or less.

The percent error of the methods and systems as described herein may be similar to current sequencing methods. For example without limitation, in some embodiments, the combined whole exome sequencing and a whole genome sequencing reactions may have a percent error rate in detecting one or more copy number variations or diagnosing a specific condition when compared to the sensitivity of whole exome sequencing alone. The current sequencing methods may be a high coverage whole genome sequencing alone. The percent error rate of the methods and systems as described herein may be within about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%, 1.2%, 1.3%, 1.4%, 1.5%, 1.6%, 1.7%, 1.8%, 1.9%, or 2% of the current sequencing methods. The percent error rate of the methods and systems as described herein may be less than the percent error rate of current sequencing methods. The percent error rate of the methods and systems as described herein may be at least about 10%, 9,%, 8%, 7%, 6%, 5%, 4%, 3%, 2%, 1.75%, 1.5%, 1.25%, 1%, 0.9%, 0.8%, 0.7%, 0.6%, 0.5%, 0.4%, 0.3%, 0.2%, 0.1% less than the percent error rate of current sequencing methods. The percent error rate of the methods and systems as described herein may be less than about 2%, 1.75%, 1.5%, 1.25%, 1%, 0.75%, 0.50%, 0.25%, 0.10%, 0.075%, 0.050%, 0.025%, or 0.001%. In some embodiments, the methods and systems disclosed herein may have a similar percent error rate when compared to the sensitivity or specificity of a high coverage whole genome sequencing alone.

The error of the methods and systems as described herein can be determined as a Phred quality score. The Phred quality score may be assigned to each base call in automated sequencer traces and may be used to compare the efficacy of different sequencing methods. The Phred quality score (Q) may be defined as a property which is logarithmically related to the base-calling error probabilities (P). The Phred quality score (Q) may be calculated as Q=−10 log 10P. The Phred quality score of the methods and systems as described herein may be similar to the Phred quality score of current sequencing methods. For example without limitation, in some embodiments, the combined whole exome sequencing and a low coverage whole genome sequencing reactions may have a similar Phred quality score in detecting one or more copy number variations or diagnosing a specific condition when compared to the Phred quality score of whole exome sequencing alone or a high coverage whole genome sequencing alone. The Phred quality score of the methods and systems as described herein may be within 1, 2, 3, 4, 5, 6, 7, 8, 9, 10 of the Phred quality score of the methods and systems as described herein. The Phred quality score of the methods and systems as described herein may be less than the Phred quality score of the methods and systems as described herein. The Phred quality score of the methods and systems as described herein may be at least about 10, 9, 8, 7, 6, 5, 4, 3, 2, 1 less than the Phred quality score of the methods and systems as described herein. The Phred quality score of the methods and systems as described herein may be greater than 5, 6, 7, 8, 9, 10, 11, 12, 13, 14, 15, 16, 17, 18, 19, 20, 25, or 30. The Phred quality score of the methods and systems as described herein may be greater than 35, 40, 41, 42, 43, 44, 45, 46, 47, 48, 49, 50, 51, 52, 53, 54, 55, 56, 57, 58, 59, or 60. The Phred quality score of the methods and systems as described herein may be at least 35, 36, 37, 38, 39, 40, 41, 42, 43, 44, 45, 46, 47, 48, 49, 50, 51, 52, 53, 54, 55, 56, 57, 58, 59, 60 or more.

The accuracy of the one or more sequencing reactions may be similar to current sequencing methods in detecting and identifying one or more specific genomic regions. The current sequencing methods can be a whole exome sequencing alone or a high coverage whole genome sequencing alone. The accuracy of the methods and systems as described herein may be within about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%, 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, or 4% of the current sequencing methods. The accuracy of the the methods and systems as described herein may be greater than the accuracy of current sequencing methods. The accuracy of the methods and systems as described herein may be at least about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%, 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, 4%, 4.5%, 5%, 6%, 7%, 8%, 9%, 10%, 11%, 12%, 15%, 17%, 20%, 25%, 30%, 35%, 40%, 50%, or 60% greater than the accuracy of current sequencing methods. The accuracy of the methods and systems as described herein may be greater than about 70%, 75%, 80%, 85%, 90%, 91%, 92%, 93%, 94%, 95%, 96%, 97%, 98.25%, 98.5%, 98.75%, 99%, 99.25%, 99.5%, or 99.75%. The accuracy of the methods and systems as described herein may be greater than about 99.1%, 99.2%, 99.3%, 99.4%, 99.5%, 99.6%, 99.7%, 99.8%, 99.9%, 99.99%, or 90.999%.

The methods and systems disclosed herein can generate an output data identifying one or more specific genomic regions (i.e., copy number variation, or one or more polymorphisms) in a shorter time than a high coverage whole genome sequencing alone. In some embodiments, the methods and systems as described herein can identify specific genomic regions in less than 1 month, 3.5 weeks, 3 weeks, 2.5 weeks, 2 weeks, 1.5 weeks or 1 week. In some embodiments, the methods and systems as described herein can identify specific genomic regions in less than 6, 5, 4, 3, 2 or 1 days. In some embodiments, the methods and systems as described herein can identify specific genomic regions in less than 24, 23, 22, 21, 20, 19, 18, 17, 16, 15, 14, 13, 12, 11, 10, 9, 8, 7, 6, 5, 4, 3, 2 or 1 hours. In some embodiments, the methods and systems as described herein can identify specific genomic regions in less than 60, 59, 55, 50, 45, 40, 35, 30, 25, 20, 15, 10, 9, 8, 7, 6, 5, 4, 3, 2 or 1 minutes. In some embodiments, the methods and systems as described herein can identify specific genomic regions in less than 10 minutes. In some embodiments, the methods and systems as described herein can identify specific genomic regions in less than 5 minutes.

The methods and systems disclosed herein can generate an output data identifying one or more specific genomic regions (i.e., copy number variation, or one or more polymorphisms) more economically or using less reagents than a high coverage whole genome sequencing alone. In some embodiments, the methods and systems as described herein can identify specific genomic regions with 5%, 10%, 15%, 20%, 25%, 30%, 35%, 40%, 45%, 50%, 55%, 60%, 65%, 70%, 75%, 80%, 85%, 90% less financial charges to the customers or less reagents for sequencing reactions used. In some embodiments, a low coverage whole genome sequencing data costs about, or less than about 500, 450, 400, 350, 300, 250, 200, 150, 100 U.S. dollars.

Samples

The methods and systems as disclosed herein may comprise, or comprise the use of, one or more samples. The samples may be nucleic acid samples comprising one or more nucleic acid molecules. The methods and systems as disclosed herein may comprise, or comprise the use of, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more samples. The methods and systems as described herein may comprise receiving and combining one or more data inputs from one or more samples. The one or more samples can be the same or different, or a combination thereof. A nucleic acid sample can be partitioned into a plurality of partitions in order to generate different sequencing data. In some embodiments, the first nucleic acid sample and the second nucleic acid sample are the same sample. The sample may be derived from a subject. The two or more samples may be derived from a single subject. The two or more samples may be derived from 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more different subjects. The subject may be a mammal, reptile, amphibian, avian, or fish. The mammal may be a human, ape, orangutan, monkey, chimpanzee, cow, pig, horse, rodent, bird, reptile, dog, cat, or other animal. A reptile may be a lizard, snake, alligator, turtle, crocodile, and tortoise. An amphibian may be a toad, frog, newt, and salamander. Examples of avians include, but are not limited to, ducks, geese, penguins, ostriches, and owls. Examples of fish include, but are not limited to, catfish, eels, sharks, and swordfish. Preferably, the subject is a human. The subject may suffer from a disease or condition.

The two or more samples may be collected over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period.

The sample may be from a body fluid, cell, skin, tissue, organ, or combination thereof. The sample may be a blood, plasma, a blood fraction, saliva, sputum, urine, semen, transvaginal fluid, cerebrospinal fluid, stool, a cell or a tissue biopsy. The sample may be from an adrenal gland, appendix, bladder, brain, ear, esophagus, eye, gall bladder, heart, kidney, large intestine, liver, lung, mouth, muscle, nose, pancreas, parathyroid gland, pineal gland, pituitary gland, skin, small intestine, spleen, stomach, thymus, thyroid gland, trachea, uterus, vermiform appendix, cornea, skin, heart valve, artery, or vein.

The samples may comprise one or more nucleic acid molecules. The nucleic acid molecule may be a DNA molecule, RNA molecule (e.g., mRNA, cRNA or miRNA), or DNA/RNA hybrid. Examples of DNA molecules include, but are not limited to, double-stranded DNA, single-stranded DNA, single-stranded DNA hairpins, cDNA, genomic DNA. The nucleic acid may be an RNA molecule, such as a double-stranded RNA, single-stranded RNA, ncRNA, RNA hairpin, and mRNA. Examples of ncRNA include, but are not limited to, siRNA, miRNA, snoRNA, piRNA, tiRNA, PASR, TASR, aTASR, TSSa-RNA, snRNA, RE-RNA, uaRNA, x-ncRNA, hY RNA, usRNA, snaR, and vtRNA.

Nucleic Acid Samples

Methods and systems of the present disclosure can be easily applied to any type of nucleic acid sample. In some embodiments, the nucleic acid samples can be fragmented double stranded DNA including but not limited to, for example, free DNA isolated from plasma, serum, and/or urine; DNA from apoptotic cells and/or tissues; DNA fragmented enzymatically in vitro (for example, by DNase I and/or restriction endonuclease); and/or DNA fragmented by mechanical forces (hydro-shear, sonication, nebulization, etc.). Additional suitable methods and compositions of producing nucleic acid molecules comprising stem-loop oligonucleotides are further described in detail in U.S. Pat. No. 7,803,550, which is herein incorporated by reference in its entirety.

In other embodiments, methods and systems provided herein can be easily applied to any high molecular weight double stranded DNA including, for example, DNA isolated from tissues, cell culture, bodily fluids, animal tissue, plant, bacteria, fungi, viruses, etc.

Nucleic acid obtained from biological samples typically is fragmented to produce suitable fragments for analysis. Template nucleic acids may be fragmented or sheared to desired length, using a variety of mechanical, chemical and/or enzymatic methods. DNA may be randomly sheared via sonication, e.g., Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid template molecules can be from about 2 kb to about 40 kb. In a particular embodiment, nucleic acids are about 6 kb-10 kb fragments. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-C6H4-(OCH2-CH2)xOH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present disclosure, such as Chaps, zwitterion 3-14, and 3[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cysteamine, tricarboxyethyl phosphine (TCEP), or salts of sulfurous acid.

The methods and systems as disclosed herein may comprise, or comprise the use of, one or more subsets of nucleic acid molecules. The subsets of nucleic acid molecules may be derived from a nucleic acid sample. The subsets of nucleic acid molecules may be derived from the same nucleic acid sample. Alternatively, or additionally, the subsets of nucleic acid molecules are derived from two or more different nucleic acid samples. Two or more subsets of nucleic acid molecules may be differentiated by their nucleic acid content. The one or more subsets of nucleic acid molecules may comprise one or more nucleic acid molecules or a variant or derivative thereof. For example, the two or more subsets of nucleic acid molecules may comprise nucleic acids comprising different GC content, nucleic acid size, genomic regions, genomic region features, eluted nucleic acid molecules, hybridized nucleic acid molecules, non-hybridized nucleic acid molecules, amplified nucleic acid molecules, non-amplified nucleic acid molecules, supernatant-derived nucleic acid molecules, eluant-derived nucleic acid molecules, labeled nucleic acid molecules, non-labeled nucleic acid molecules, capture probe hybridized nucleic acid molecules, capture probe free nucleic acid molecules, bead bound nucleic acid molecules, bead free nucleic acid molecules, or a combination thereof. The two or more subsets of nucleic acid molecules may be differentiated by GC content, nucleic acid size, genomic regions, capture probes, beads, labels, or a combination thereof.

The methods and systems as disclosed herein may comprise, or comprise the use of, combining two or more subsets of nucleic acid molecules to produce a combined subset of nucleic acid molecules. The combined subsets of nucleic acid molecules may be derived from a nucleic acid sample. The combined subsets of nucleic acid molecules may be derived from the same nucleic acid sample. Alternatively, or additionally, the combined subsets of nucleic acid molecules are derived from two or more different nucleic acid samples. Two or more combined subsets of nucleic acid molecules may be differentiated by their nucleic acid content. The one or more combined subsets of nucleic acid molecules may comprise one or more nucleic acid molecules or a variant or derivative thereof. For example, the two or more combined subsets of nucleic acid molecules may comprise nucleic acids comprising different GC content, nucleic acid size, genomic regions, genomic region features, eluted nucleic acid molecules, hybridized nucleic acid molecules, non-hybridized nucleic acid molecules, amplified nucleic acid molecules, non-amplified nucleic acid molecules, supernatant-derived nucleic acid molecules, eluant-derived nucleic acid molecules, labeled nucleic acid molecules, non-labeled nucleic acid molecules, capture probe hybridized nucleic acid molecules, capture probe free nucleic acid molecules, bead bound nucleic acid molecules, bead free nucleic acid molecules, or a combination thereof. The two or more combined subsets of nucleic acid molecules may be differentiated by GC content, nucleic acid size, genomic regions, capture probes, beads, labels, or a combination thereof.

Subsets of nucleic acid molecules may comprise one or more genomic regions as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic regions. The one or more genomic regions may be identical, similar, different, or a combination thereof.

Subsets of nucleic acid molecules may comprise one or more genomic region features as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic region features. The one or more genomic region features may be identical, similar, different, or a combination thereof.

Subsets of nucleic acid molecules may comprise nucleic acid molecules of different sizes. The length of a nucleic acid molecule in a subset of nucleic acid molecules may be referred to as the size of the nucleic acid molecule. The average length of the nucleic acid molecules in a subset of nucleic acid molecules may be referred to as the mean size of nucleic acid molecules. As used herein, the terms "size of a nucleic acid molecule", "mean size of nucleic acid molecules", "molecular size" and "mean molecular size" may be used interchangeably. The size of a nucleic acid molecule may be used to differentiate two or more subsets of nucleic acid molecules. The difference in the mean size of nucleic acid molecules in a subset of nucleic acid molecules and the mean size of nucleic acid molecules in another subset of nucleic acid molecules may be used to differentiate the two subsets of nucleic acid molecules. The mean size of nucleic acid molecules in one subset of nucleic acid molecules may be greater than the mean size of nucleic acid molecules in at least one other subset of nucleic acid molecules. The mean size of nucleic acid molecules in one subset of nucleic acid molecules may be less than the mean size of nucleic acid molecules in at least one other subset of nucleic acid molecules. The difference in mean molecular size between two or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or basepairs. In some aspects of the disclosure, the difference in mean molecular size between two or more subsets of nucleic acid molecules is at least about 200 bases or bases pairs. Alternatively, the difference in mean molecular size between two or more subsets of nucleic acid molecules is at least about 300 bases or bases pairs.

Subsets of nucleic acid molecules may comprise nucleic acid molecules of different sequencing sizes. The length of a nucleic acid molecule in a subset of nucleic acid molecules to be sequenced may be referred to as the sequencing size of the nucleic acid molecule. The average length of the nucleic acid molecules in a subset of nucleic acid molecules may be referred to as the mean sequencing size of nucleic acid molecules. As used herein, the terms "sequencing size of a nucleic acid molecule", "mean sequencing size of nucleic acid molecules", "molecular sequencing size" and "mean molecular sequencing size" may be used interchangeably. The mean molecular sequencing size of one or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or basepairs. The sequencing size of a nucleic acid molecule may be used to differentiate two or more subsets of nucleic acid molecules. The difference in the mean sequencing size of nucleic acid molecules in a subset of nucleic acid molecules and the mean sequencing size of nucleic acid molecules in another subset of nucleic acid molecules may be used to differentiate the two subsets of nucleic acid molecules. The mean sequencing size of nucleic acid molecules in one subset of nucleic acid molecules may be greater than the mean sequencing size of nucleic acid molecules in at least one other subset of nucleic acid molecules. The mean sequencing size of nucleic acid molecules in one subset of nucleic acid molecules may be less than the mean sequencing size of nucleic acid molecules in at least one other subset of nucleic acid molecules. The difference in mean molecular sequencing size between two or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or basepairs. In some aspects of the disclosure, the difference in mean molecular sequencing size between two or more subsets of nucleic acid molecules is at least about 200 bases or bases pairs. Alternatively, the difference in mean molecular sequencing size between two or more subsets of nucleic acid molecules is at least about 300 bases or bases pairs.

Two or more subsets of nucleic acid molecules may be at least partially complementary. For example, a first subset of nucleic acid molecules may comprise nucleic acid molecules comprising at least a first portion of the genome and a second subset of nucleic acid molecules may comprise nucleic acid molecules comprising at least a second portion of the genome, wherein the first and second portion of the genome differ by one or more nucleic acid molecules. Thus, the first subset and the second subset are at least partially complementary. The complementarity of two or more subsets of nucleic acid molecules may be at least about 10%, 15%, 20%, 25%, 30%, 35%, 40%, 45%, 50%, 55%, 60%, 65%, 70%, 75%, 80%, 85%, 90%, 95%, 97%, or more. As used herein, the term "complementarity of two or more subsets of nucleic acid molecules" generally refers to genomic content of the two or more subsets and the extent to which the two or more subsets encompass the content of one or more genomic regions. For example, a first subset of nucleic acid molecules comprises 50% of total high GC exomes and a second subset of nucleic acid molecules comprises 50% of the total low GC exomes, then the complementarity of the two subsets of nucleic acid molecules in reference to an entire exome is 50%. In another example, a first subset of nucleic acid molecules comprises 100% of the total bead bound nucleic acid molecules and the second subset of nucleic acid molecules comprises 100% of the total bead free nucleic acid molecules, the complementarity of the two subsets in reference to the total nucleic acid molecules is 100%.

Subsets of nucleic acid molecules may comprise bead bound nucleic acid molecules. Two or more subsets of nucleic acid molecules may be differentiated into bead bound nucleic acid molecules and bead free nucleic acid molecules. For example, a first subset of nucleic acid molecules may comprise one or more bead bound nucleic acid molecules and a second subset of nucleic acid molecules may comprise bead free nucleic acid molecules. Bead free nucleic acid molecules may refer to nucleic acid molecules that are not bound to one or more beads. Bead free nucleic acid molecules may refer to nucleic acid molecules that have been eluted from one or more beads. For example, the nucleic acid molecule from a bead bound nucleic acid molecule may be eluted to produce a bead free nucleic acid molecule.

Subsets of nucleic acid molecules may comprise capture probe hybridized nucleic acid molecules. Two or more subsets of nucleic acid molecules may be differentiated into capture probe hybridized nucleic acid molecules and capture probe free nucleic acid molecules. For example, a first subset of nucleic acid molecules may comprise one or more capture probe hybridized nucleic acid molecules and a second subset of nucleic acid molecules may comprise capture probe free nucleic acid molecules. Capture probe free nucleic acid molecules may refer to nucleic acid molecules that are not hybridized to one or more capture probes. Capture probe free nucleic acid molecules may refer to nucleic acid molecules that are dehybridized from one or more capture probes. For example, the capture probe from a capture probe hybridized nucleic acid molecule may be removed to produce a capture probe free nucleic acid molecule.

Capture probes may hybridize to one or more nucleic acid molecules in a sample or in a subset of nucleic acid molecules. Capture probes may hybridize to one or more genomic regions. Capture probes may hybridize to one or more genomic regions within, around, near, or spanning one or more genes, exons, introns, UTRs, or a combination thereof. Capture probes may hybridize to one or more genomic regions spanning one or more genes, exons, introns, UTRs, or a combination thereof. Capture probes may hybridize to one or more known inDels. Capture probes may hybridize to one or more known structural variants.

Subsets of nucleic acid molecules may comprise labeled nucleic acid molecules. Two or more subsets of nucleic acid molecules may be differentiated into labeled nucleic acid molecules and non-labeled nucleic acid molecules. For example, a first subset of nucleic acid molecules may comprise one or more labeled nucleic acid molecules and a second subset of nucleic acid molecules may comprise non-labeled nucleic acid molecules. Non-labeled nucleic acid molecules may refer to nucleic acid molecules that are not attached to one or more labels. Non-labeled nucleic acid molecules may refer to nucleic acid molecules that have been detached from one or more labels. For example, the label from a labeled nucleic acid molecule may be removed to produce a non-labeled nucleic acid molecule.

The methods and systems as disclosed herein may comprise, or comprise the use of, one or more labels. The one or more labels may be attached to one or more capture probes, nucleic acid molecules, beads, primers, or a combination thereof. Examples of labels include, but are not limited to, detectable labels, such as radioisotopes, fluorophores, chemiluminophores, chromophore, lumiphore, enzymes, colloidal particles, and fluorescent microparticles, quantum dots, as well as antigens, antibodies, haptens, avidin/streptavidin, biotin, haptens, enzymes cofactors/substrates, one or more members of a quenching system, a chromogens, haptens, a magnetic particles, materials exhibiting nonlinear optics, semiconductor nanocrystals, metal nanoparticles, enzymes, aptamers, and one or more members of a binding pair.

The one or more subsets of nucleic acid molecules may be subjected to one or more assays. The one or more subsets of nucleic acid molecules may be subjected to one or more assays based on their biochemical features. The one or more subsets of nucleic acid molecules may be subjected to one or more assays based on their genomic region features. The one or more subsets of nucleic acid molecules may be subjected to 1, 2, 3, 4, 5, 6, 7, 8, 9, 10 or more assays. The one or more subsets of nucleic acid molecules may be subjected to 1, 2, 3, 4, 5, 6, 7, 8, 9, 10 or more assays based on their biochemical features. The one or more subsets of nucleic acid molecules may be subjected to 1, 2, 3, 4, 5, 6, 7, 8, 9, 10 or more assays based on their genomic region features. The one or more subsets of nucleic acid molecules may be subjected to 1, 2, 3, 4, 5, 6, 7, 8, 9, 10 or more identical assays. The one or more subsets of nucleic acid molecules may be subjected to 1, 2, 3, 4, 5, 6, 7, 8, 9, 10 or more identical assays based on their biochemical features. The one or more subsets of nucleic acid molecules may be subjected to 1, 2, 3, 4, 5, 6, 7, 8, 9, 10 or more identical assays based on their genomic region features. The one or more subsets of nucleic acid molecules may be subjected to 1, 2, 3, 4, 5, 6, 7, 8, 9, 10 or more similar assays. The one or more subsets of nucleic acid molecules may be subjected to 1, 2, 3, 4, 5, 6, 7, 8, 9, 10 or more similar assays based on their biochemical features. The one or more subsets of nucleic acid molecules may be subjected to 1, 2, 3, 4, 5, 6, 7, 8, 9, 10 or more similar assays based on their genomic region features. The one or more subsets of nucleic acid molecules may be subjected to 1, 2, 3, 4, 5, 6, 7, 8, 9, 10 or more different assays. The one or more subsets of nucleic acid molecules may be subjected to 1, 2, 3, 4, 5, 6, 7, 8, 9, 10 or more different assays based on their biochemical features. The one or more subsets of nucleic acid molecules may be subjected to 1, 2, 3, 4, 5, 6, 7, 8, 9, 10 or more different assays based on their genomic region features. The two or more subsets of nucleic acid molecules may be subjected to one or more identical processing steps based on their biochemical features. The two or more subsets of nucleic acid molecules may be subjected to one or more identical processing steps based on their genomic region features. The two or more subsets of nucleic acid molecules may be subjected to one or more similar processing steps based on their biochemical features. The two or more subsets of nucleic acid molecules may be subjected to one or more similar processing steps based on their genomic region features. The two or more subsets of nucleic acid molecules may be subjected to one or more different processing steps based on their biochemical features. The two or more subsets of nucleic acid molecules may be subjected to one or more different processing steps based on their genomic region features.

The methods and systems as disclosed herein may comprise, or comprise the use of, producing two or more subsets of nucleic acid molecules. The two or more subsets of nucleic acid molecules may be separated fluidically, separated into two or more containers, separated into two or more locations, or a combination thereof. For example, a first subset of nucleic acid molecules and a second subset of nucleic acid molecules are fluidically separated. In another example, a first subset of nucleic acid molecules is in a first container and a second subset of nucleic acid molecules is in a second container. In yet another example, a first subset of nucleic acid molecules and a second subset of nucleic acid molecules are assigned to two or more locations on a first container, and a third subset of nucleic acid molecules is in a second container.

Genomic Regions

The methods and systems as disclosed herein may comprise, or comprise the use of, nucleic acid samples or subsets of nucleic acid molecules comprising one or more genomic regions. The methods and systems as disclosed herein may comprise, or comprise the use of, nucleic acid samples or subsets of nucleic acid molecules comprising one or more sets of genomic regions. The one or more genomic regions may comprise one or more genomic region features. The genomic region features may comprise an entire genome or a portion thereof. The genomic region features may comprise an entire exome or a portion thereof. The genomic region features may comprise one or more sets of genes. The genomic region features may comprise one or more genes. The genomic region features may comprise one or more sets of regulatory elements. The genomic region features may comprise one or more regulatory elements. The genomic region features may comprise a set of polymorphisms. The genomic region features may comprise one or more polymorphisms. The genomic region feature may relate to the GC content, complexity, and/or mappability of one or more nucleic acid molecules. The genomic region features may comprise one or more simple tandem repeats (STRs), unstable expanding repeats, segmental duplications, single and paired read degenerative mapping scores, GRCh37 patches, or a combination thereof. The genomic region features may comprise one or more low mean coverage regions from whole genome sequencing (WGS), zero mean coverage regions from WGS, validated compressions, or a combination thereof. The genomic region features may comprise one or more alternate or non-reference sequences. The genomic region features may comprise one or more gene phasing and reassembly genes. In some aspects of the disclosure, the one or more genomic region features are not mutually exclusive. For example, a genomic region feature comprising an entire genome or a portion thereof can overlap with an additional genomic region feature such as an entire exome or a portion thereof, one or more genes, one or more regulatory elements, etc. Alternatively, the one or more genomic region futures are mutually exclusive. For example, a genomic region comprising the noncoding portion of an entire genome would not overlap with a genomic region feature such as an exome or portion thereof or the coding portion of a gene. Alternatively, or additionally, the one or more genomic region features are partially exclusive or partially inclusive. For example, a genomic region comprising an entire exome or a portion thereof can partially overlap with a genomic region comprising an exon portion of a gene. However, the genomic region comprising the entire exome or portion thereof would not overlap with the genomic region comprising the intron portion of the gene. Thus, a genomic region feature comprising a gene or portion thereof may partially exclude and/or partially include a genomic region feature comprising an entire exome or portion thereof.

The methods and systems as disclosed herein may comprise, or comprise the use of, nucleic acid samples or subsets of nucleic acid molecules comprising one or more genomic regions, wherein at least one of the one or more genomic regions comprises a genomic region feature comprising an entire genome or portion thereof. The entire genome or portion thereof may comprise one or more coding portions of the genome, one or more noncoding portions of the genome, or a combination thereof. The coding portion of the genome may comprise one or more coding portions of a gene encoding for one or more proteins. The one or more coding portions of the genome may comprise an entire exome or a portion thereof. Alternatively, or additionally, the one or more coding portions of the genome may comprise one or more exons. The one or more noncoding portions of the genome may comprise one or more noncoding molecules or a portion thereof. The noncoding molecules may comprise one or more noncoding RNA, one or more regulatory elements, one or more introns, one or more pseudogenes, one or more repeat sequences, one or more transposons, one or more viral elements, one or more telomeres, a portion thereof, or a combination thereof. The noncoding RNAs may be functional RNA molecules that are not translated into protein. Examples of noncoding RNAs include, but are not limited to, ribosomal RNA, transfer RNA, piwi-interacting RNA, microRNA, siRNA, shRNA, snoRNA, sncRNA, and lncRNA. Pseudogenes may be related to known genes and are typically no longer expressed. Repeat sequences may comprise one or more tandem repeats, one or more interspersed repeats, or a combination thereof. Tandem repeats may comprise one or more satellite DNA, one or more minisatellites, one or more microsatellites, or a combination thereof. Interspersed repeats may comprise one or more transposons. Transposons may be mobile genetic elements. Mobile genetic elements are often able to change their position within the genome. Transposons may be classified as class I transposable elements (class I TEs) or class II transposable elements (class II TEs). Class I TEs (e.g., retrotransposons) may often copy themselves in two stages, first from DNA to RNA by transcription, then from RNA back to DNA by reverse transcription. The DNA copy may then be inserted into the genome in a new position. Class I TEs may comprise one or more long terminal repeats (LTRs), one or more long interspersed nuclear elements (LINEs), one or more short interspersed nuclear elements (SINEs), or a combination thereof. Examples of LTRs include, but are not limited to, human endogeneous retroviruses (HERVs), medium reiterated repeats 4 (MER4), and retrotransposon. Examples of LINEs include, but are not limited to, LINE1 and LINE2. SINES may comprise one or more Alu sequences, one or more mammalian-wide interspersed repeat (MIR), or a combination thereof. Class II TEs (e.g., DNA transposons) often do not involve an RNA intermediate. The DNA transposon is often cut from one site and inserted into another site in the genome. Alternatively, the DNA transposon is replicated and inserted into the genome in a new position. Examples of DNA transposons include, but are not limited to, MER1, MER2, and mariners. Viral elements may comprise one or more endogenous retrovirus sequences. Telomeres are often regions of repetitive DNA at the end of a chromosome.

The methods and systems as disclosed herein may comprise, or comprise the use of, nucleic acid samples or subsets of nucleic acid molecules comprising one or more genomic regions, wherein at least one of the one or more genomic regions comprises a genomic region feature comprising an entire exome or portion thereof. The exome is often the part of the genome formed by exons. The exome may be formed by untranslated regions (UTRs), splice sites and/or intronic regions. The entire exome or portion thereof may comprise one or more exons of a protein coding gene. The entire exome or portion thereof may comprise one or more untranslated regions (UTRs), splice sites, and introns.

The methods and systems as disclosed herein may comprise, or comprise the use of, nucleic acid samples or subsets of nucleic acid molecules comprising one or more genomic regions, wherein at least one of the one or more genomic regions comprises a genomic region feature comprising a gene or portion thereof. Typically, a gene comprises stretches of nucleic acids that code for a polypeptide or a functional RNA. A gene may comprise one or more exons, one or more introns, one or more untranslated regions (UTRs), or a combination thereof. Exons are often coding sections of a gene, transcribed into a precursor mRNA sequence, and within the final mature RNA product of the gene. Introns are often noncoding sections of a gene, transcribed into a precursor mRNA sequence, and removed by RNA splicing. UTRs may refer to sections on each side of a coding sequence on a strand of mRNA. A UTR located on the 5' side of a coding sequence may be called the 5' UTR (or leader sequence). A UTR located on the 3' side of a coding sequence may be called the 3' UTR (or trailer sequence). The UTR may contain one or more elements for controlling gene expression. Elements, such as regulatory elements, may be located in the 5' UTR. Regulatory sequences, such as a polyadenylation signal, binding sites for proteins, and binding sites for miRNAs, may be located in the 3' UTR. Binding sites for proteins located in the 3' UTR may include, but are not limited to, selenocysteine insertion sequence (SECIS) elements and AU-rich elements (AREs). SECIS elements may direct a ribosome to translate the codon UGA as selenocysteine rather than as a stop codon. AREs are often stretches consisting primarily of adenine and uracil nucleotides, which may affect the stability of a mRNA.

The methods and systems as disclosed herein may comprise, or comprise the use of, nucleic acid samples or subsets of nucleic acid molecules comprising one or more genomic regions, wherein at least one of the one or more genomic regions comprises a genomic region feature comprising a set of genes. The sets of genes may include, but are not limited to, Mendel DB Genes, Human Gene Mutation Database (HGMD) Genes, Cancer Gene Census Genes, Online Mendelian Inheritance in Man (OMIM) Mendelian Genes, HGMD Mendelian Genes, and human leukocyte antigen (HLA) Genes. The set of genes may have one or more known Mendelian traits, one or more known disease traits, one or more known drug traits, one or more known biomedically interpretable variants, or a combination thereof. A Mendelian trait may be controlled by a single locus and may show a Mendelian inheritance pattern. A set of genes with known Mendelian traits may comprise one or more genes encoding Mendelian traits including, but are not limited to, ability to taste phenylthiocarbamide (dominant), ability to smell (bitter almond-like) hydrogen cyanide (recessive), albinism (recessive), brachydactyly (shortness of fingers and toes), and wet (dominant) or dry (recessive) earwax. A disease trait cause or increase risk of disease may be inherited in a Mendelian or complex pattern. A set of genes with known disease traits may comprise one or more genes encoding disease traits including, but are not limited to, Cystic Fibrosis, Hemophilia, and Lynch Syndrome. A drug trait may alter metabolism, optimal dose, adverse reactions and side effects of one or more drugs or family of drugs. A set of genes with known drug traits may comprise one or more genes encoding drug traits including, but are not limited to, CYP2D6, UGT1A1 and ADRB1. A biomedically interpretable variant may be a polymorphism in a gene that is associated with a disease or indication. A set of genes with known biomedically interpretable variants may comprise one or more genes encoding biomedically interpretable variants including, but are not limited to, cystic fibrosis (CF) mutations, muscular dystrophy mutations, p53 mutations, Rb mutations, cell cycle regulators, receptors, and kinases. Alternatively, or additionally, a set of genes with known biomedically interpretable variants may comprise one or more genes associated with Huntington's disease, cancer, cystic fibrosis, muscular dystrophy (e.g., Duchenne muscular dystrophy).

The methods and systems as disclosed herein may comprise, or comprise the use of, nucleic acid samples or subsets of nucleic acid molecules comprising one or more genomic regions, wherein at least one of the one or more genomic regions comprises a genomic region feature comprising a regulatory element or a portion thereof. Regulatory elements may be cis-regulatory elements or trans-regulatory elements. Cis-regulatory elements may be sequences that control transcription of a nearby gene. Cis-regulatory elements may be located in the 5' or 3' untranslated regions (UTRs) or within introns. Trans-regulatory elements may control transcription of a distant gene. Regulatory elements may comprise one or more promoters, one or more enhancers, or a combination thereof. Promoters may facilitate transcription of a particular gene and may be found upstream of a coding region. Enhancers may exert distant effects on the transcription level of a gene.

The methods and systems as disclosed herein may comprise, or comprise the use of, nucleic acid samples or subsets of nucleic acid molecules comprising one or more genomic regions, wherein at least one of the one or more genomic regions comprises a genomic region feature comprising a polymorphism or a portion thereof. Generally, a polymorphism refers to a mutation in a genotype. A polymorphism may comprise one or more base changes, an insertion, a repeat, or a deletion of one or more bases. Copy number variants (CNVs), transversions, and other rearrangements are also forms of genetic variation. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are a form of polymorphisms. In some aspects of the disclosure, one or more polymorphisms comprise one or more single nucleotide variations, inDels, small insertions, small deletions, structural variant junctions, variable length tandem repeats, flanking sequences, or a combination thereof. The one or more polymorphisms may be located within a coding and/or non-coding region. The one or more polymorphisms may be located within, around, or near a gene, exon, intron, splice site, untranslated region, or a combination thereof. The one or more polymorphisms may span at least a portion of a gene, exon, intron, untranslated region.

The methods and systems as disclosed herein may comprise, or comprise the use of, nucleic acid samples or subsets of nucleic acid molecules comprising one or more genomic regions, wherein at least one of the one or more genomic regions comprises a genomic region feature comprising one or more simple tandem repeats (STRs), unstable expanding repeats, segmental duplications, single and paired read degenerative mapping scores, GRCh37 patches, or a combination thereof. The one or more STRs may comprise one or more homopolymers, one or more dinucleotide repeats, one or more trinucleotide repeats, or a combination thereof. The one or more homopolymers may be about 7, 8, 9, 10, 11, 12, 13, 14, 15, 16, 17, 18, 19, 20 or more bases or basepairs. The dinucleotide repeats and/or trinucleotide repeats may be about 15, 16, 17, 18, 19, 20, 21, 22, 23, 24, 25, 26, 27, 28, 29, 30, 35, 40, 45, 50 or more bases or basepairs. The single and paired read degenerative mapping scores may be based on or derived from alignability of 100 mers by GEM from ENCODE/CRG (Guigo), alignability of 75 mers by GEM from ENCODE/CRG (Guigo), 100 base pair box car average for signal mappability, max of locus and possible pairs for paired read score, or a combination thereof. The genomic region features may comprise one or more low mean coverage regions from whole genome sequencing (WGS), zero mean coverage regions from WGS, validated compressions, or a combination thereof. The low mean coverage regions from WGS may comprise regions generated from Illumina v3 chemistry, regions below the first percentile of Poission distribution based on mean coverage, or a combination thereof. The Zero mean coverage regions from WGS may comprise regions generated from Illumina v3 chemistry. The validated compressions may comprise regions of high mapped depth, regions with two or more observed haplotypes, regions expected to be missing repeats in a reference, or a combination thereof. The genomic region features may comprise one or more alternate or non-reference sequences. The one or more alternate or non-reference sequences may comprise known structural variant junctions, known insertions, known deletions, alternate haplotypes, or a combination thereof. The genomic region features may comprise one or more gene phasing and reassembly genes. Examples of phasing and reassembly genes include, but are not limited to, one or more major histocompatibility complexes, blood typing, and amylase gene family. The one or more major histocompatibility complexes may comprise one or more HLA Class I, HLA Class II, or a combination thereof. The one or more HLA class I may comprise HLA-A, HLA-B, HLA-C, or a combination thereof. The one or more HLA class II may comprise HLA-DP, HLA-DM, HLA-DOA, HLA-DOB, HLA-DQ, HLA-DR, or a combination thereof. The blood typing genes may comprise ABO, RHD, RHCE, or a combination thereof.

The methods and systems as disclosed herein may comprise, or comprise the use of, nucleic acid samples or subsets of nucleic acid molecules comprising one or more genomic regions, wherein at least one of the one or more genomic regions comprises a genomic region feature related to the GC content of one or more nucleic acid molecules. The GC content may refer to the GC content of a nucleic acid molecule. Alternatively, the GC content may refer to the GC content of one or more nucleic acid molecules and may be referred to as the mean GC content. As used herein, the terms "GC content" and "mean GC content" may be used interchangeably. The GC content of a genomic region may be a high GC content. Typically, a high GC content refers to a GC content of greater than or equal to about 65%, 70%, 75%, 80%, 85%, 90%, 95%, 97%, or more. In some aspects of the disclosure, a high GC content may refer to a GC content of greater than or equal to about 70%. The GC content of a genomic region may be a low GC content. Typically, a low GC content refers to a GC content of less than or equal to about 65%, 60%, 55%, 50%, 45%, 40%, 35%, 30%, 25%, 20%, 15%, 10%, 5%, 2%, or less.

The difference in GC content may be used to differentiate two or more genomic regions or two or more subsets of nucleic acid molecules. The difference in GC content may refer to the difference in GC content of one nucleic acid molecule and another nucleic acid molecule. Alternatively, the difference in GC content may refer to the difference in mean GC content of two or more nucleic acid molecules in a genomic region from the mean GC content of two or more nucleic acid molecules in another genomic region. In some aspects of the disclosure, the difference in GC content refers to the difference in mean GC content of two or more nucleic acid molecules in a subset of nucleic acid molecules from the mean GC content of two or more nucleic acid molecules in another subset of nucleic acid molecules. The difference in GC content may be about 5%, 6%, 7%, 8%, 9%, 10%, 15%, 20%, 25%, 30%, 35%, 40%, or more. In some aspects of the disclosure, the difference in GC content is at least about 5%. The difference in GC content may be at least about 10%.

The methods and systems as disclosed herein may comprise, or comprise the use of, nucleic acid samples or subsets of nucleic acid molecules comprising one or more genomic regions, wherein at least one of the one or more genomic regions comprises a genomic region feature related to the complexity of one or more nucleic acid molecules. The complexity of a nucleic acid molecule may refer to the randomness of a nucleotide sequence. Low complexity may refer to patterns, repeats and/or depletion of one or more species of nucleotide in the sequence.

The methods and systems as disclosed herein may comprise, or comprise the use of, nucleic acid samples or subsets of nucleic acid molecules comprising one or more genomic regions, wherein at least one of the one or more genomic regions comprises a genomic region feature related to the mappability of one or more nucleic acid molecules. The mappability of a nucleic acid molecule may refer to uniqueness of its alignment to a reference sequence. A nucleic acid molecule with low mappability may have poor alignment to a reference sequence.

The methods and systems as disclosed herein may comprise, or comprise the use of, nucleic acid samples or subsets of nucleic acid molecules comprising one or more genomic regions comprising one or more genomic region features. In some aspects of the disclosure, a single genomic region comprises 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The two or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic region features. In some aspects of the disclosure, two or more genomic regions comprise 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more identical or similar genomic region features. Alternatively, or additionally, two or more genomic regions comprise 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more different genomic region features.

The methods and systems as disclosed herein may comprise, or comprise the use of, nucleic acid samples or subsets of nucleic acid molecules comprising two or more genomic regions, wherein the two or more genomic regions are differentiateable by one or more genomic region features. The methods and systems as disclosed herein may comprise, or comprise the use of, nucleic acid samples or subsets of nucleic acid molecules comprising two or more subsets of nucleic acid molecules, wherein the two or more subsets of nucleic acid molecules are differentiateable by one or more genomic region features. The two or more genomic regions and/or the two or more subsets of nucleic acid molecules may be differentiateable by 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, or 30 or more genomic region features.

The methods and systems as disclosed herein may comprise, or comprise the use of, nucleic acid samples or subsets of nucleic acid molecules comprising one or more sets of genomic regions. For example, The methods and systems as disclosed herein may, or comprise the use of, comprise nucleic acid samples or subsets of nucleic acid molecules comprising, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more sets of genomic regions. The one or more sets of genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more different genomic regions. The one or more sets of genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more identical or similar genomic regions. The one or more sets of genomic regions may comprise a combination of one or more different genomic regions and one or more identical or similar genomic regions.

Capture Probes

The methods and systems disclosed herein may comprise, or comprise the use of, one or more capture probes, a plurality of capture probes, or one or more capture probe sets. Typically, the capture probe comprises a nucleic acid binding site. The capture probe may further comprise one or more linkers. The capture probes may further comprise one or more labels. The one or more linkers may attach the one or more labels to the nucleic acid binding site.

The methods and systems disclosed herein may comprise, or comprise the use of, 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more capture probes or capture probe sets. The one or more capture probes or capture probe sets may be different, similar, identical, or a combination thereof.

The one or more capture probe may comprise a nucleic acid binding site that hybridizes to at least a portion of the one or more nucleic acid molecules or variant or derivative thereof in the sample or subset of nucleic acid molecules. The capture probes may comprise a nucleic acid binding site that hybridizes to one or more genomic regions. The capture probes may hybridize to different, similar, and/or identical genomic regions. The one or more capture probes may be at least about 50%, 55%, 60%, 65%, 70%, 75%, 80%, 85%, 90%, 95%, 97%, 99% or more complementary to the one or more nucleic acid molecules or variants or derivatives thereof.

The capture probes may comprise one or more nucleotides. The capture probes may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The capture probes may comprise about 100 nucleotides. The capture probes may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the capture probes comprise between about 80 nucleotides to about 100 nucleotides.

The plurality of capture probes or the capture probe sets may comprise two or more capture probes with identical, similar, and/or different nucleic acid binding site sequences, linkers, and/or labels. For example, two or more capture probes comprise identical nucleic acid binding sites. In another example, two or more capture probes comprise similar nucleic acid binding sites. In yet another example, two or more capture probes comprise different nucleic acid binding sites. The two or more capture probes may further comprise one or more linkers. The two or more capture probes may further comprise different linkers. The two or more capture probes may further comprise similar linkers. The two or more capture probes may further comprise identical linkers. The two or more capture probes may further comprise one or more labels. The two or more capture probes may further comprise different labels. The two or more capture probes may further comprise similar labels. The two or more capture probes may further comprise identical labels.

Diseases or Conditions

The methods and systems as disclosed herein may comprise, or comprise the use of, predicting, diagnosing, and/or prognosing a status or outcome of a disease or condition in a subject based on one or more biomedical outputs. Predicting, diagnosing, and/or prognosing a status or outcome of a disease in a subject may comprise diagnosing a disease or condition, identifying a disease or condition, determining the stage of a disease or condition, assessing the risk of a disease or condition, assessing the risk of disease recurrence, assessing reproductive risk, assessing genetic risk to a fetus, assessing the efficacy of a drug, assessing risk of an adverse drug reaction, predicting optimal drug dosage, predicting drug resistance, or a combination thereof.

The samples disclosed herein may be from a subject suffering from a cancer. The sample may comprise malignant tissue, benign tissue, or a mixture thereof. The cancer may be a recurrent and/or refractory cancer. Examples of cancers include, but are not limited to, sarcomas, carcinomas, lymphomas or leukemias.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. The cancer may be a skin cancer, such as a basal cell carcinoma, squamous, melanoma, nonmelanoma, or actinic (solar) keratosis.

The cancer may be a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. The cancer may be a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Additional diseases and/or conditions include, but are not limited to, atherosclerosis, inflammatory diseases, autoimmune diseases, rheumatic heart disease. Examples of inflammatory diseases include, but are not limited to, acne vulgaris, Alzheimer's, ankylosing spondylitis, arthritis (osteoarthritis, rheumatoid arthritis (RA), psoriatic arthritis), asthma, atherosclerosis, celiac disease, chronic prostatitis, Crohn's disease, colitis, dermatitis, diverticulitis, fibromyalgia, glomerulonephritis, hepatitis, irritable bowel syndrome (IBS), systemic lupus erythematous (SLE), nephritis, Parkinson's disease, pelvic inflammatory disease, sarcoidosis, ulcerative colitis, and vasculitis.

Examples of autoimmune diseases include, but are not limited to, acute disseminated encephalomyelitis (ADEM), Addison's disease, agammaglobulinemia, alopecia areata, amyotrophic Lateral Sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's diseasevDercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritisvepidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditisvHenoch-Schonlein purpuravherpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathyvinterstitial cystitis, juvenile idiopathic arthritis aka juvenile rheumatoid arthritis, Kawasaki's disease, Lambert-Eaton myasthenic syndrome, leukocytoclastic vasculitis, Lichen planus, Lichen sclerosus, linear IgA disease (LAD), Lou Gehrig's disease (Also Amyotrophic lateral sclerosis), lupoid hepatitis aka autoimmune hepatitis, lupus erythematosus, Majeed syndrome, Ménière's disease, microscopic polyangiitis, mixed connective tissue disease, morphea, Mucha-Habermann disease, multiple sclerosis, myasthenia gravis, myositis, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, Schmidt syndrome another form of APS, Schnitzler syndrome, scleritis, scleroderma, serum sickness, Sjögren's syndrome, spondyloarthropathy, Stiff person syndrome, subacute bacterial endocarditis (SBE), Susac's syndrome, Sweet's syndrome, sympathetic ophthalmia, Takayasu's arteritis, temporal arteritis (also known as "giant cell arteritis"), thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, vitiligo, and Wegener's granulomatosis.

The methods and systems as provided herein may also be useful for detecting, monitoring, diagnosing and/or predicting a subject's response to an implanted device. Exemplary medical devices include but are not limited to stents, replacement heart valves, implanted cerebella stimulators, hip replacement joints, breast implants, and knee implants.

The methods and systems as disclosed herein may be used for monitoring the health of a fetus using whole or partial genome analysis of nucleic acids derived from a fetus, as compared to the maternal genome. For example, nucleic acids can be useful in pregnant subjects for fetal diagnostics, with fetal nucleic acids serving as a marker for gender, rhesus D status, fetal aneuploidy, and sex-linked disorders. The methods and systems as disclosed herein may identify fetal mutations or genetic abnormalities. The methods and systems as disclosed herein can enable detection of extra or missing chromosomes, particularly those typically associated with birth defects or miscarriage. The methods and systems as disclosed herein may comprise, or comprise the use of, the diagnosis, prediction or monitoring of autosomal trisomies (e.g., Trisomy 13, 15, 16, 18, 21, or 22) and may be based on the detection of foreign molecules. The trisomy may be associated with an increased chance of miscarriage (e.g., Trisomy 15, 16, or 22). Alternatively, the trisomy that is detected is a liveborn trisomy that may indicate that an infant may be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The methods disclosed herein may comprise one or more genomic regions on the following chromosomes: 13, 18, 21, X, or Y. For example, the foreign molecule may be on chromosome 21 and/or on chromosome 18, and/or on chromosome 13. The one or more genomic regions may comprise multiple sites on multiple chromosomes.

Further fetal conditions that can be determined based on the methods and systems herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g., XXXX, XXYY, XXXY, XYYY, XXXXX, XXXXY, XXXYY, XYYYY and XXYYY), monoploidy, triploidy (three of every chromosome, e.g., 69 chromosomes in humans), tetraploidy (four of every chromosome, e.g., 92 chromosomes in humans), pentaploidy and multiploidy.

The methods and systems as disclosed may comprise detecting, monitoring, quantitating, or evaluating one or more pathogen-derived nucleic acid molecules or one or more diseases or conditions caused by one or more pathogens. Exemplary pathogens include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*. Additional pathogens include, but are not limited to, *Mycobacterium tuberculosis, Streptococcus, Pseudomonas, Shigella, Campylobacter*, and *Salmonella*.

The disease or conditions caused by one or more pathogens may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a streptococcus bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis*, and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

Therapeutics

The methods and systems as disclosed herein may comprise, or comprise the use of, treating and/or preventing a disease or condition in a subject based on one or more biomedical outputs. The one or more biomedical outputs may recommend one or more therapies. The one or more biomedical outputs may suggest, select, designate, recommend or otherwise determine a course of treatment and/or prevention of a disease or condition. The one or more biomedical outputs may recommend modifying or continuing one or more therapies. Modifying one or more therapies may comprise administering, initiating, reducing, increasing, and/or terminating one or more therapies. The one or more therapies comprise an anti-cancer, antiviral, antibacterial, antifungal, immunosuppressive therapy, or a combination thereof. The one or more therapies may treat, alleviate, or prevent one or more diseases or indications.

Examples of anti-cancer therapies include, but are not limited to, surgery, chemotherapy, radiation therapy, immunotherapy/biological therapy, photodynamic therapy. Anti-cancer therapies may comprise chemotherapeutics, monoclonal antibodies (e.g., rituximab, trastuzumab), cancer vaccines (e.g., therapeutic vaccines, prophylactic vaccines), gene therapy, or combination thereof.

The one or more therapies may comprise an antimicrobial. Generally, an antimicrobial refers to a substance that kills or inhibits the growth of microorganisms such as bacteria, fungi, virus, or protozoans. Antimicrobial drugs either kill microbes (microbicidal) or prevent the growth of microbes (microbiostatic). There are mainly two classes of antimicrobial drugs, those obtained from natural sources (e.g., antibiotics, protein synthesis inhibitors (such as aminoglycosides, macrolides, tetracyclines, chloramphenicol, polypeptides)) and synthetic agents (e.g., sulphonamides, cotrimoxazole, quinolones). In some instances, the antimicrobial drug is an antibiotic, anti-viral, anti-fungal, antimalarial, anti-tuberculosis drug, anti-leprotic, or anti-protozoal.

Antibiotics are generally used to treat bacterial infections. Antibiotics may be divided into two categories: bactericidal antibiotics and bacteriostatic antibiotics. Generally, bactericidals may kill bacteria directly where bacteriostatics may prevent them from dividing. Antibiotics may be derived from living organisms or may include synthetic antimicrobials, such as the sulfonamides. Antibiotics may include aminoglycosides, such as amikacin, gentamicin, kanamycin, neomycin, netilmicin, tobramycin, and paromomycin. Alternatively, antibiotics may be ansamycins (e.g., geldanamycin, herbimycin), cabacephems (e.g., loracarbef), carbapenems (e.g., ertapenem, doripenem, imipenem, cilastatin, meropenem), glycopeptides (e.g., teicoplanin, vancomycin, telavancin), lincosamides (e.g., clindamycin, lincomycin, daptomycin), macrolides (e.g., azithromycin, clarithromycin, dirithromycin, erythromycin, roxithromycin, troleandomycin, telithromycin, spectinomycin, spiramycin), nitrofurans (e.g., furazolidone, nitrofurantoin), and polypeptides (e.g., bacitracin, colistin, polymyxin B).

In some instances, the antibiotic therapy includes cephalosporins such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole.

The antibiotic therapy may also include penicillins. Examples of penicillins include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, and ticarcillin.

Alternatively, quinolines may be used to treat a bacterial infection. Examples of quinilones include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin.

In some instances, the antibiotic therapy comprises a combination of two or more therapies. For example, amoxicillin and clavulanate, ampicillin and sulbactam, piperacillin and tazobactam, or ticarcillin and clavulanate may be used to treat a bacterial infection.

Sulfonamides may also be used to treat bacterial infections. Examples of sulfonamides include, but are not limited to, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole (co-trimoxazole) (tmp-smx).

Tetracyclines are another example of antibiotics. Tetracyclines may inhibit the binding of aminoacyl-tRNA to the mRNA-ribosome complex by binding to the 30S ribosomal subunit in the mRNA translation complex. Tetracyclines include demeclocycline, doxycycline, minocycline, oxytetracycline, and tetracycline. Additional antibiotics that may be used to treat bacterial infections include arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, clofazimine, dapsone, capreomycin, cycloserine, ethambutol, ethionamide, isoniazid, pyrazinamide, rifampicin, rifamycin, rifabutin, rifapentine, and streptomycin.

Antiviral therapies are a class of medication used specifically for treating viral infections. Like antibiotics, specific antivirals are used for specific viruses. They are relatively harmless to the host, and therefore can be used to treat infections. Antiviral therapies may inhibit various stages of the viral life cycle. For example, an antiviral therapy may inhibit attachment of the virus to a cellular receptor. Some antiviral therapies may include agents that mimic the virus associated protein (VAP and bind to the cellular receptors. Other antiviral therapies may inhibit viral entry, viral uncoating (e.g., amantadine, rimantadine, pleconaril), viral synthesis, viral integration, viral transcription, or viral translation (e.g., fomivirsen). In some instances, the antiviral therapy is a morpholino antisense. Antiviral therapies should be distinguished from viricides, which actively deactivate virus particles outside the body.

Many of the antiviral drugs available are designed to treat infections by retroviruses, mostly HIV. Antiretroviral drugs may include the class of protease inhibitors, reverse transcriptase inhibitors, and integrase inhibitors. Drugs to treat HIV may include a protease inhibitor (e.g., invirase, saquinavir, kaletra, lopinavir, lexiva, fosamprenavir, norvir, ritonavir, prezista, duranavir, reyataz, viracept), integrase inhibitor (e.g., raltegravir), transcriptase inhibitor (e.g., abacavir, ziagen, agenerase, amprenavir, aptivus, tipranavir, crixivan, indinavir, fortovase, saquinavir, Intelence™, etravirine, isentress, viread), reverse transcriptase inhibitor (e.g., delavirdine, efavirenz, epivir, hivid, nevirapine, retrovir, AZT, stuvadine, truvada, videx), fusion inhibitor (e.g., fuzeon, enfuvirtide), chemokine coreceptor antagonist (e.g., selzentry, emtriva, emtricitabine, epzicom, or trizivir). Alternatively, antiretroviral therarapies may be combination therapies, such as atripla (e.g., efavirenz, emtricitabine, and tenofovira disoproxil fumarate) and completer (embricitabine, rilpivirine, and tenofovir disoproxil fumarate). Herpes viruses, best known for causing cold sores and genital herpes, are usually treated with the nucleoside analogue acyclovir. Viral hepatitis (A-E) are caused by five unrelated hepatotropic viruses and are also commonly treated with antiviral drugs depending on the type of infection. Influenza A and B viruses are important targets for the development of new influenza treatments to overcome the resistance to existing neuraminidase inhibitors such as oseltamivir.

In some instances, the antiviral therapy may comprise a reverse transcriptase inhibitor. Reverse transcriptase inhibitors may be nucleoside reverse transcriptase inhibitors or non-nucleoside reverse transcriptase inhibitors. Nucleoside reverse transcriptase inhibitors may include, but are not limited to, combivir, emtriva, epivir, epzicom, hivid, retrovir, trizivir, truvada, videx ec, videx, viread, zerit, and ziagen. Non-nucleoside reverse transcriptase inhibitors may comprise edurant, intelence, rescriptor, sustiva, and viramune (immediate release or extended release).

Protease inhibitors are another example of antiviral drugs and may include, but are not limited to, agenerase, aptivus, crixivan, fortovase, invirase, kaletra, lexiva, norvir, prezista, reyataz, and viracept. Alternatively, the antiviral therapy may comprise a fusion inhibitor (e.g., enfuviride) or an entry inhibitor (e.g., maraviroc).

Additional examples of antiviral drugs include abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors, ganciclovir, ibacitabine, imunovir, idoxuridine, imiquimod, indinavir, inosine, integrase inhibitor, interferons (e.g., interferon type I, II, III), lamivudine, lopinavir, loviride, maraviroc, moroxydine, methisazone, nelfinavir, nevirapine, nexavir, nucleoside analogues, oseltamivir, peginterferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

An antifungal drug is medication that may be used to treat fungal infections such as athlete's foot, ringworm, candidiasis (thrush), serious systemic infections such as cryptococcal meningitis, and others. Antifungals work by exploiting differences between mammalian and fungal cells to kill off the fungal organism. Unlike bacteria, both fungi and humans are eukaryotes. Thus, fungal and human cells are similar at the molecular level, making it more difficult to find a target for an antifungal drug to attack that does not also exist in the infected organism.

Antiparasitics are a class of medications which are indicated for the treatment of infection by parasites, such as nematodes, cestodes, trematodes, infectious protozoa, and amoebae. Like antifungals, they must kill the infecting pest without serious damage to the host.

EXAMPLES

Methods and systems of the present disclosure may be applied to various types of samples, such as nucleic acid samples, protein samples, or other biological samples.

Example 1

Three Independent Workflows for the Production of ESP, HGCP and LRP Libraries This example provides three independent workflows for the preparation of Exome Supplement Plus (ESP), high GC content (HGCP), and specific enrichment pulldown (LRP) libraries from a single nucleic acid sample.

Illumina's RSB (or 50 mM Sodium Ascorbic) is added to three different Covaris microtubes containing 1 μg of genomic DNA (DNA) from a single sample to produce 52.5 μL of total volume in each microtube. The microtubes are designated as ESP, HGCP, and LRP. The gDNA in each microtube is sheared using the Covaris settings in Table 1.

TABLE 1

| Covaris settings | | | |
|---|---|---|---|
|  | ESP | HGCP | LRP |
| Duty factor: | 20% | 20% | 20% |
| Cyc/burst: | 200 | 200 | 200 |
| Time (sec): | 80 | 80 | 25 |
| Peak Incident Power (W): | 50 | 50 | 50 |
| Temp (° C.): | 20 | 20 | 20 |

The microtubes are spun down and 50 μL of the fragmented DNA is transferred to PCR plates. 10 μL of RSB is added to each well. The HGCP sample plate is heated at 65° C. for 5 minutes. The ESP and LRP plates are not heated at 65° C. 40 μL of Illumina's ERP is added to each sample plate by pipetting up and down to mix. The plates are sealed. The plates are incubated at 30° C. for 30 minutes. The DNA is purified by adding Ampure XP beads to each plate. For the ESP and HGCP plates, 90 μL of Ampure XP beads are added. For the LRP plate, 50 μL of Ampure XP beads are added. DNA is eluted with 17.5 μL of RSB.

12.5 μL of Illumina's ATL is added to the eluted DNA and transferred to a new plate. The plates with the eluted DNA are incubated at 37° C. for 30 minutes.

Adapters are ligated to the DNA by adding 2.5 μL of RSB, 2.5 μL of Ligation (LIG) mix, and 2.5 μL of adapters to each well. The samples are mixed well and the plate is sealed. The plate is incubated for 10 minutes at 30° C. 5 μL of STL (0.5M EDTA) is added to each well. The samples are mixed thoroughly. The adapter ligated DNA is purified by adding 42.5 μL of Ampure XP beads to each well. Ligated DNA is eluted with 50 μL of RSB. The ligated DNA is purified by adding 50 μL of Ampure beads and eluting the DNA with 20 μL of RSB. The Ampure bead purification and elution is performed twice.

The ligated DNA is amplified by adding 25 μL of 2× kappa hifi polymerase and 5 μL of primer to each ligated DNA sample and by running a PCR with 8 cycles. The amplified DNA is purified with 50 μL of Ampure beads and the DNA is eluted with 30 μL of RSB. The amplified DNA from the three different sample preparations are used to prepare the ESP, HGCP, and LRP libraries.

The ESP, HGCP, and LRP libraries are validated by running each library on a DNA 1000 chip and quantifying with a BR Qubit assay.

Hybrization reactions are performed on the ESP, HGCP, and LRP samples using ESP, HGCP and LRP specific capture probes. 3 independent hybridization reactions are set up according to Table 2.

TABLE 2

| pull down | ESP | HGCP | LRP |
|---|---|---|---|
| DNA library | ESP | HGCP | LRP |
| probe | ESP | HGCP | LRP |

Hybridization reactions are performed according to Agilent's standard SureSelect protocol.

Example 2

Two Independent Workflows for the Production of ESP, HGCP and LRP Libraries This example provides two independent workflows for the preparation of Exome Supplement Plus (ESP), high GC content (HGCP) and specific enrichment pulldown (LRP) libraries from a single nucleic acid sample.

RSB (or 50 mM Sodium Acetate) is added to two different Covaris microtubes containing 1 μg of genomic DNA (DNA) from a single sample to produce 52.5 μL of total volume in each microtube. The microtubes are designated as ESP/HGCP and LRP. The gDNA in the microtube is sheared using the Covaris settings in Table 3.

TABLE 3

| Covaris settings | | |
|---|---|---|
|  | ESP/HGCP | LRP |
| Duty factor: | 20% | 20% |
| Cyc/burst: | 200 | 200 |
| Time (sec): | 80 | 25 |
| Peak Incident Power (W): | 50 | 50 |
| Temp (° C.): | 20 | 20 |

The microtubes are spun down and 50 μL of the fragmented DNA is transferred to PCR plates. 10 μL of RSB is added to each well. The ESP/HGCP sample plate is heated at 65° C. for 5 minutes. Or the ESP/HGCP and LRP plates are not heated at 65° C. 40 μL ERP is added to each sample plate by pipetting up and down to mix. The plates are sealed. The plates are incubated at 30° C. for 30 minutes. The DNA is purified by adding Ampure XP beads to each plate. For the ESP and HGCP plates, 90 μL of Ampure XP beads is added. For the LRP plate, 50 μL of Ampure XP beads is added. DNA is eluted with 17.5 μL of RSB.

12.5 μL of ATL is added to the eluted DNA. The plates with the eluted DNA are incubated at 37° C. for 30 minutes.

Adapters are ligated to the DNA by adding 2.5 μL of RSB, 2.5 μL of Ligation (LIG) mix, and 2.5 μL of adapters to each well. The samples are mixed well and the plate is sealed. The plate is incubated for 10 minutes at 30° C. 5 μL of STL (0.5M EDTA) is added to each well. The samples are mixed thoroughly. The adapter ligated DNA is purified by adding 42.5 μL of Ampure XP beads to each well. Ligated DNA is eluted with 50 μL of RSB. The ligated DNA is purified by adding 50 μL of Ampure beads and eluting the DNA with 20 μL of RSB. The Ampure bead purification and elution are performed twice.

The ligated DNA is amplified by adding 25 μL of 2× kappa hifi polymerase and 5 μL of primer to each ligated DNA sample and by running a PCR with 8 cycles. The amplified DNA is purified with 50 μL of Ampure beads and the DNA is eluted with 30 μL of RSB. The amplified DNA from the sample preparations is used to prepare the ESP, HGCP, and LRP libraries.

The ESP, HGCP, and LRP libraries are validated by running each library on a DNA High-Sensitivity chip and quantifying with a BR Qubit assay.

Hybrization reactions are performed on the ESP, HGCP, and LRP samples using ESP, HGCP and LRP specific capture probes. 3 independent hybridization reactions are set up according to Table 4.

TABLE 4

| pull down | ESP | HGCP | LRP |
|---|---|---|---|
| DNA library | ESP/HGCP | ESP/HGCP | LRP |
| probe | ESP | HGCP | LRP |

Hybridization reactions are performed according to Agilent's standard SureSelect protocol.

Example 3

A Single Workflow for the Production of ESP, HGCP and LRP Libraries

This example provides a single workflow for the preparation of Exome Supplement Plus (ESP), high GC content (HGCP), and specific enrichment pulldown (LRP) libraries from a single nucleic acid sample.

RSB (or 50 mM Sodium Acetate) is added to a Covaris microtube containing 3 μg of genomic DNA (DNA) from a single sample to produce 52.5 μL of total volume. The gDNA in the microtube is sheared using the Covaris settings in Table 5.

TABLE 5

| Covaris settings | |
|---|---|
| Duty factor: | 20% |
| Cyc/burst: | 200 |
| Time (sec): | 25 |
| Peak Incident Power (W): | 50 |
| Temp (° C.): | 20 |

The microtubes are spun down and 50 μL of the fragmented DNA is transferred to a single PCR plate. 10 μL of RSB is added to each well. The sample plate is either heated at 65° C. for 5 minutes or not heated. 40 μL ERP is added to each sample plate by pipetting up and down to mix. The plates are sealed. The plate is incubated at 30° C. for 30 minutes. The DNA is purified by adding Ampure XP beads to each plate. 90 μL of Ampure XP beads is added to the plates. The mixture is incubated for 8 minutes at room temperature. The standard Ampure protocol is performed. Beads are rehydrated in 20 μL of thawed RSB for 2 minutes at room temperature. 17.5 μL of supernatant is transferred to new wells in an Illumina's ALP plate.

12.5 μL of ATL is added to the eluted DNA. The ALP plates are incubated at 37° C. for 30 minutes.

Adapters are ligated to the DNA by adding 2.5 μL of RSB, 2.5 μL of Ligation (LIG) mix, and 2.5 μL of adapters to each well. The samples are mixed well and the plate is sealed. The plate is incubated for 10 minutes at 30° C. 5 μL of STL (0.5M EDTA) is added to each well. The samples are mixed thoroughly. The adapter ligated DNA is purified by adding 42.5 μL of Ampure XP beads to each well. Ligated DNA is eluted with 100 μL of RSB. 50 μL of Ampure XP beads are added to the 100 μL of ligated DNA. The 150 μL of the supernatant is transferred to a new well, leaving the Ampure XP bead bound DNA in the previous wells. DNA is eluted from the Ampure XP beads by adding 20 μL of RSB. The eluted DNA is the LRP subset.

20 μL of Ampure beads are added to the 150 μL of supernatant. The DNA is eluted in 100 μL of RSB. 60 μL of Ampure XP beads are added to the 100 μL of DNA. The 160 μL of supernatant is transferred to a new well, leaving the Ampure XP bead bound DNA in the previous wells. DNA is eluted from the Ampure XP beads by adding 20 μL of RSB. The eluted DNA is the ESP/HGCP subset.

The LRP subset of DNA and the ESP/HGCP subset of DNA are amplified by adding 25 μL of 2× kappa hifi polymerase and 5 μL of primer to each ligated DNA sample and by running a PCR with 8 cycles. The amplified DNA is purified with 50 μL of Ampure XP beads and the beads are rehydrated in 30 μL of RSB. The amplified DNA from the subsets is used to prepare the ESP, HGCP, and LRP libraries.

The ESP, HGCP, and LRP libraries are validated by running each library on a DNA High-Sensitivity chip and quantifying with a BR Qubit assay.

Hybrization reactions are performed on the ESP, HGCP, and LRP samples using ESP, HGCP and LRP specific capture probes. 3 independent hybridization reactions are set up according to Table 6.

TABLE 6

| pull down | ESP | HGCP | LRP |
|---|---|---|---|
| DNA library | ESP/HGCP | ESP/HGCP | LRP |
| probe | ESP | HGCP | LRP |

Hybridization reactions are performed according to Agilent's standard SureSelect protocol.

Example 4

Shear Time and Fragment Sizes

Figure 5:
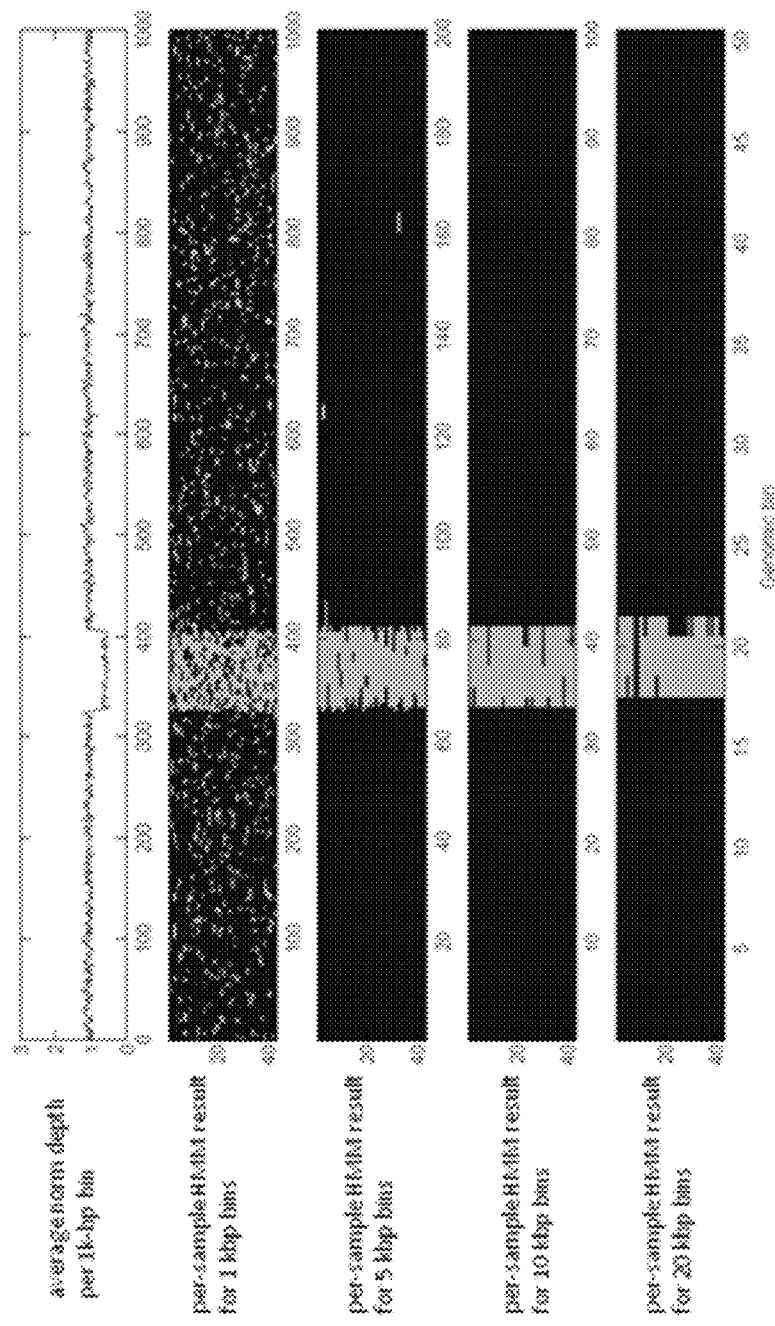
FIG. 5 illustrates the effects of different genomic bin sizes in whole genome sequencing.

Genomic DNA (gDNA) is sheared by varying the shear time of a Covaris setting. The gDNA fragments produced by various shear times are then analyzed. Results are shown in FIG. 5 and Table 7.

TABLE 7

| Shear time and mean fragment size | | |
|---|---|---|
| Number | Shear Time (seconds) | Mean Fragment Size (basepairs) |
| 1 | 375 | 150 |
| 2 | 175 | 200 |
| 3 | 80 | 200 |
| 4 | 40 | 400 |
| 5 | 32 | 500 |
| 6 | 25 | 800 |

Example 5

Bead Ratio and Fragment Size

The ratio of the volume of beads to the volume of the nucleic acid sample is varied and the effects of these ratios on mean fragment size is analyzed. As can be shown in FIG.

6A, varying the ratio of the volume of the beads to the volume of the nucleic acid sample from 0.8 (line 1), 0.7 (line 2), 0.6 (line 3), 0.5 (line 4) and 0.4 (line 5) results in a shift in the mean size of the DNA fragments. Generally, it appears that the lower the ratio, then the larger the mean fragment size.

Example 6

Ligation Reactions and Fragment Size

A combination of two different shear times and three different ligation reactions are conducted on a nucleic acid sample. Sample 1 is sheared for 25 seconds and a ligation reaction is performed on the long insert DNA as prepared by Step 5 of Example 9 (lig-up). Sample 2 is sheared for 32 seconds and a ligation reaction is performed on the long insert DNA as prepared by Step 5 of Example 9 (lig-up). Sample 3 is sheared for 25 seconds and a ligation reaction is performed on the mid insert DNA as prepared by Step 8 of Example 9 (lig-mid). Sample 4 is sheared for 32 seconds and a ligation reaction is performed on the mid insert DNA as prepared by Step 8 of Example 9 (lig-mid). Sample 5 is sheared for 25 seconds and a ligation reaction is performed on the short insert DNA as prepared by Step 11 of Example 9 (lig-low). Sample 6 is sheared for 32 seconds and a ligation reaction is performed on the short insert DNA as prepared by Step 11 of Example 9 (lig-low). FIG. 7 shows the mean fragment size for the six reactions.

Example 7

Rhodobacter Sphaeroides

The *Rhodobacter sphaeroides* ATCC 17025 genome is 4.56 Million basepairs long and the GC content of the genome is analyzed. Results for the analysis are shown in Table 8.

TABLE 8

| Browser Chrom/Plasmid Name | Length (bp) | GC Content (%) | Gene Count | NCBI RefSeq Accession |
|---|---|---|---|---|
| chr | 3217726 | 68.48 | 3181 | NC_009428 |
| plasmid_pRSPA01 | 877879 | 67.69 | 849 | NC_009429 |
| plasmid_pRSPA02 | 289489 | 67.6 | 278 | NC_009430 |
| plasmid_pRSPA03 | 121962 | 69.36 | 114 | NC_009431 |
| plasmid_pRSPA04 | 36198 | 64.05 | 32 | NC_009432 |
| plasmid_pRSPA05 | 13873 | 58.93 | 12 | NC_009433 |

Example 8

Optimization of *Rhodobacter Sphaeroides* DNA (High GC Content)

DNA from *Rhodobacter Sphaeroides* is amplified with a variety of polymerases and amplification conditions. Amplified DNA is then sequenced. High GC flowcell refers to sequencing reactions on DNA samples comprising primarily DNA with high GC content. Mix GC flowcell refers to sequencing reactions on DNA samples comprising a mixture of DNA with high and low GC content. As shown in Table 9, brief heating at 65° C. before ER (end repair) improves coverage of high GC content DNA (see PST-000292).

TABLE 9

| DNA | PCR conditions | PF reads | mapped reads | | ratio (>80% GC, <60% GC) |
|---|---|---|---|---|---|
| 2 × 150, High GC flowcell (primarily High GC content) | | | | | |
| PST-000190 | PCR free | 985736 | 945734 | 95.94% | 73.90% |
| PST-000191 | kapa 10 cycle | 1211930 | 1174309 | 96.90% | 70.80% |
| PST-000192 | kapa 10 cycle + betaine | 1247310 | 1206917 | 96.76% | 70.80% |
| PST-000193 | kapa 10 cycle + DMSO | 1183084 | 1144464 | 96.74% | 70.40% |
| PST-000194 | kapa hifi 10 cycle | 1102832 | 1067306 | 96.78% | 68.30% |
| PST-000195 | kapa hifi 10 cycle + deaza_dGTP | 756856 | 739857 | 97.75% | 2.40% |
| PST-000196 | kapa GC 10 cycle | 1299004 | 1255979 | 96.69% | 70.60% |
| PST-000197 | illumina 10 cycle | 1347780 | 1298231 | 96.32% | 52.10% |
| PST-000198 | illumina 10 cycle, long denature | 1256278 | 1209607 | 96.28% | 50.60% |
| PST-000199 | kapa 8 cycle | 1013116 | 978349 | 96.57% | 69.80% |
| 2 × 150, Mix GC flowcell (high and low GC content) | | | | | |
| PST-000191 | kapa 10 cycle | 909256 | 854341 | 93.96% | 66.80% |
| 2 × 250, Mix GC flowcell (high and low GC content) | | | | | |
| PST-000290 | PCR free | 1009022 | 779191 | 77.22% | 70.80% |

TABLE 9-continued

| DNA | PCR conditions | PF reads | mapped reads | | ratio (>80% GC, <60% GC) |
|---|---|---|---|---|---|
| PST-000291 | PCR free, 60C ER | 1100298 | 863058 | 78.44% | 73.10% |
| PST-000292 | PCR free, 65C ER | 1157944 | 932378 | 80.52% | 78.20% |
| PST-000293 | PCR free, 70C ER | 1200318 | 944391 | 78.68% | 75.10% |

Example 9

Preparation of Genomic DNA

The following steps are used to prepare subsets of nucleic acid molecules from a sample comprising genomic DNA:
1. A sample comprising genomic DNA is sheared with M220 for 15-35 seconds.
2. The fragmented gDNA is purified with SPRI beads after ligation (ratio of the volume of SPRI beads to the DNA sample was 1) and the DNA is eluted into 100 µL of elution buffer (EB).
3. 50 µL of SPRI beads are added to the 100 µL of DNA.
4. The supernatant is transferred to a new tube.
5. The DNA from the remaining bead bound DNA is eluted. This eluted DNA is called the long insert.
6. 10 µL of SPRI beads are added to the supernatant from Step 4.
7. The supernatant from Step 6 is transferred to a new tube.
8. The DNA from the remaining bead bound DNA of Step 6 is eluted. This eluted DNA is called the mid insert.
9. 20 µL of SPRI beads are added to the supernatant from Step 7.
10. The supernatant from Step 9 is transferred to a new tube.
11. The DNA from the remaining bead bound DNA of Step 9 is eluted. This eluted DNA is called the short insert.

Example 10

Segregation and Independent Processing of Interpretable Genomic Content

Illumina TruSeq Exome enrichment followed by Illumina sequencing is a typical example of targeted DNA sequencing. However, this process can fail to target many biomedically interesting non-exomic as well as exomic regions for enrichment and also can fail to adequately sequence many of the regions it does target. Furthermore, many of the sequenced regions may have unacceptably high error rates. It is found that many of these gaps and failures are due to specific problems related to bulk sequencing that may be more adequately addressed by specialized sequencing protocols or technologies.

A large and unique set of medically interpretable content encompassing both proprietary data and numerous publicly available sources, including both exomic and non-exomic regions, as well as non-reference or alternative sequences, has been compiled. Much of this content is not adequately covered in standard exome sequencing. This performance gap has been analyzed, and a multipronged approach has been developed to more completely cover this content by independently processing particular types of problems with specialized sample preparation, amplification, sequencing technology and/or bioinformatics to best recover the underlying sequence. Three targeted subsets and protocols have been developed to address this performance gap.

In content regions skipped by standard exome processing, but still in nominally tractable genomic regions, additional baits have been developed to enrich these regions for standard sequencing. In some cases, non-reference sequences of interest may additionally be targeted (e.g., common normal and/or cancer SV junctions, common InDels or in general sequences in which the reference has a rare allele adversely affects enrichment hybridization performance for most of the population). This Exome Supplement Pulldown (ESP) is pooled with standard exome DNA libraries for very economical sequencing. Table 10 lists proprietary and public data sets of medical and research interest, as well as the anticipated coverage gap with Illumina's TruSeq exome kit. Table 10 shows an exemplary list of nucleic acid molecules in the ESP subset.

TABLE 10

List of content in the ESP subset
Content120924LG.bed

| Priority | Content Name | by Set | | Cumulative | | Missed in TruSeq by Set | | Missed in TruSeq Cumulative | |
|---|---|---|---|---|---|---|---|---|---|
| | | Bases | Ranges | Bases | Ranges | Bases | Ranges | Bases | Ranges |
| 1 | MendelDB_snp_0913_2012.bed | 78,882 | 1,576 | 65,968 | 1,163 | 13,844 | 299 | 13,844 | 299 |
| 2 | PharmGKB_snp_0914_2012.bed | 14,600 | 292 | 80,253 | 1,444 | 8,642 | 178 | 22,486 | 477 |
| 3 | medical_dbSNP_regulome1_Suspect.bed | 22,005 | 440 | 100,522 | 1,836 | 15,796 | 323 | 38,088 | 794 |
| 4 | GeneReview_snp_0913_2012.bed | 61,615 | 1,231 | 114,970 | 2,098 | 11,459 | 249 | 41,520 | 865 |
| 5 | HGMD_ClinVar_snp_0913_2012.bed | 1,062,528 | 21,220 | 779,524 | 12,537 | 197,594 | 3,873 | 219,612 | 4,313 |
| 6 | Clinical_Channel_snp_0913_2012.bed | 771,293 | 15,404 | 928,410 | 15,103 | 219,084 | 4,239 | 324,542 | 6,309 |
| 7 | OMIM_snp_0914_2012.bed | 500,554 | 9,999 | 928,410 | 15,103 | 102,540 | 2,092 | 324,542 | 6,309 |
| 8 | Varimed_multi_ethnic_snp_0914_2012.bed | 89,201 | 1,784 | 1,002,730 | 16,568 | 77,177 | 1,568 | 391,484 | 7,660 |
| 9 | Varimed_highconf_snp_0914_2012.bed | 1,177,673 | 23,553 | 2,032,039 | 36,733 | 1,073,682 | 21,358 | 1,355,991 | 26,787 |
| 10 | HGMD_mut.bed | 4,305,255 | 84,885 | 3,421,232 | 51,658 | 556,284 | 8,900 | 1,698,980 | 31,491 |
| 11 | Exons_VIP-Genes-120713 | 233,123 | 652 | 3,604,514 | 51,812 | 49,783 | 331 | 1,738,877 | 31,691 |

TABLE 10-continued

List of content in the ESP subset
Content120924LG.bed

| Pri-ority | Content Name | by Set | | Cumulative | | Missed in TruSeq by Set | | Missed in TruSeq Cumulative | |
|---|---|---|---|---|---|---|---|---|---|
| | | Bases | Ranges | Bases | Ranges | Bases | Ranges | Bases | Ranges |
| 12 | Regulome1_VIP-Genes-120713 | 3,000 | 60 | 3,606,632 | 51,850 | 2,503 | 54 | 1,740,885 | 31,732 |
| 13 | Exons_MendelDB-Genes-120916 | 14,325,633 | 40,761 | 16,091,103 | 71,703 | 3,726,418 | 19,767 | 5,049,919 | 45,516 |
| 14 | Regulome1_MendelDB-Genes-120916 | 147,553 | 2,951 | 16,201,606 | 73,825 | 125,129 | 2,553 | 5,157,542 | 47,677 |
| 15 | Exons_HGMD-Genes-120913 | 26,801,793 | 74,195 | 29,292,835 | 105,150 | 7,047,052 | 36,440 | 8,633,799 | 64,224 |
| 16 | Regulome1_HGMD-Genes-120913 | 254,356 | 5,087 | 29,381,797 | 106,849 | 214,286 | 4,372 | 8,720,429 | 65,963 |
| 17 | Exons_CancerGeneCensus_gene | 3,786,660 | 9,924 | 31,022,066 | 110,788 | 934,846 | 4,641 | 9,113,184 | 67,842 |
| 18 | Regulome1_CancerGeneCensus_gene | 31,651 | 633 | 31,031,990 | 110,976 | 27,842 | 569 | 9,122,893 | 68,033 |
| 19 | Exons_OMIM_Mendelian_gene | 19,484,727 | 54,285 | 32,499,571 | 114,516 | 5,032,796 | 26,346 | 9,518,418 | 69,854 |
| 20 | Regulome1_OMIM_Mendelian_gene | 210,906 | 4,218 | 32,522,006 | 114,944 | 179,685 | 3,668 | 9,540,226 | 70,290 |
| 21 | Exons_HGMD_Mendelian_gene | 27,988,755 | 77,427 | 35,226,837 | 121,987 | 7,363,878 | 37,504 | 10,174,050 | 73,377 |
| 22 | Regulome1_HGMD_Mendelian_gene | 266,255 | 5,325 | 35,260,944 | 122,647 | 226,927 | 4,632 | 10,207,319 | 74,046 |
| 23 | Exons_HLAclass1 | 5,969 | 24 | 35,260,944 | 122,647 | 3,554 | 26 | 10,207,319 | 74,046 |
| 24 | Regulome1_HLAclass1 | 950 | 19 | 35,260,944 | 122,647 | 743 | 15 | 10,207,319 | 74,046 |
| 25 | Exons_HLAclass2 | 28,398 | 82 | 35,273,022 | 122,664 | 11,750 | 50 | 10,209,818 | 74,060 |
| 26 | Regulome1_HLAclass2 | 350 | 7 | 35,273,098 | 122,665 | 100 | 2 | 10,209,868 | 74,061 |
| 27 | CFTR_Intronic | 603 | 3 | 35,273,651 | 122,667 | 603 | 3 | 10,210,421 | 74,063 |
| 28 | Triallelic_in_Footprint | 7,891 | 154 | 35,280,947 | 122,809 | 7,434 | 150 | 10,217,712 | 74,205 |
| 29 | phastConsElements46way-top0.5percent | 2,662,784 | 7,681 | 36,864,760 | 126,352 | 1,794,961 | 5,994 | 11,753,993 | 78,509 |

In content regions having very high GC content (>70%), standard sequencing typically performs poorly because the elevated $T_m$ (melting temperature) of these areas can cause poor PCR or other amplification due to competition with more numerous lower $T_m$ sequences and sequences with other problematic structures, e.g., hairpins and other secondary structure. These regions are typically either skipped or perform poorly in standard sequencing. A process to target content areas of high GC content (HGCP) and customized sample preparation and sequencing protocols to specifically improve the performance of this library have been developed by optimizing temperatures, incubation times, buffers, and enzymes. An example composition of such a library intersected with the content of the HGCP subset is shown in Table 11.

TABLE 11

Exemplary list of content in the HGCP subset includes 50 bp dilation

| Priority | HGCPmerge100_120924LG.bed Content Name | by Set | | Cumulative | | HGCP by Set | | HGCP Cumulative | |
|---|---|---|---|---|---|---|---|---|---|
| | | Bases | Ranges | Bases | Ranges | Bases | Ranges | Bases | Ranges |
| | MendelDB_snp_0913_2012.bed | 180,101 | 909 | 180,101 | 909 | 12,539 | 89 | 12,539 | 89 |
| | PharmGKB_snp_0914_2012.bed | 42,673 | 266 | 222,474 | 1,173 | 3,092 | 22 | 15,631 | 111 |
| | medical_dbSNP_regulome1_Suspect.bed | 62,226 | 390 | 281,629 | 1,547 | 883 | 7 | 16,387 | 116 |
| | GeneReview_snp_0913_2012.bed | 148,233 | 753 | 322,106 | 1,765 | 11,074 | 77 | 20,586 | 145 |
| | HGMD_ClinVar_snp_0913_2012.bed | 1,881,403 | 8,749 | 1,976,714 | 9,287 | 162,863 | 948 | 166,434 | 971 |
| | Clinical_Channel_snp_0913_2012.bed | 1,553,376 | 7,442 | 2,382,381 | 11,058 | 112,701 | 674 | 185,369 | 1,075 |
| | OMIM_snp_0914_2012.bed | 1,091,353 | 5,527 | 2,382,381 | 11,058 | 92,276 | 563 | 185,369 | 1,075 |
| | Varimed_multi_ethnic_snp_0914_2012.bed | 269,869 | 1,600 | 2,609,304 | 12,341 | 4,066 | 29 | 188,395 | 1,097 |
| | Varimed_highconf_snp_0914_2012.bed | 3,538,004 | 19,531 | 5,749,403 | 29,271 | 26,929 | 203 | 208,093 | 1,244 |
| | HGMD_mut.bed | 4,713,066 | 18,283 | 8,448,253 | 37,978 | 448,145 | 2,157 | 481,839 | 2,386 |
| | Exons_VIP-Genes-120713 | 301,582 | 564 | 8,655,649 | 38,208 | 31,335 | 100 | 506,873 | 2,445 |
| | Regulome1_VIP-Genes-120713 | 9,180 | 48 | 8,661,738 | 28,231 | 0 | 0 | 506,873 | 2,445 |
| | Exons_MendelDB-Genes-120916 | 18,594,872 | 32,943 | 23,550,190 | 57,802 | 1,986,487 | 6,270 | 2,147,437 | 7,091 |
| | Regulome1_MendelDB-Genes-120916 | 445,360 | 2,606 | 23,890,795 | 59,262 | 9,488 | 77 | 2,151,072 | 7,110 |
| | Exons_HGMD-Genes-120913 | 38,574,073 | 60,810 | 40,302,799 | 85,129 | 3,697,923 | 11,625 | 3,918,341 | 12,444 |
| | Regulome1_HGMD-Genes-120913 | 765,607 | 4,447 | 40,572,922 | 86,302 | 14,220 | 115 | 3,921,622 | 12,455 |
| | Exons_CancerGeneCensus.gene | 4,823,472 | 8,240 | 42,627,241 | 89,578 | 526,402 | 1,590 | 4,139,209 | 13,145 |
| | Regulome1_CancerGeneCensus_gene | 95,341 | 581 | 42,657,367 | 89,729 | 2,374 | 17 | 4,140,165 | 13,150 |
| | Exons_OMIM_Mendelian_gene | 25,166,172 | 44,269 | 44,497,746 | 92,630 | 2,702,576 | 8,437 | 4,340,856 | 13,745 |
| | Regulome1_OMIM_Mendelian_gene | 636,246 | 3,726 | 44,567,099 | 92,943 | 14,171 | 111 | 4,342,155 | 13,751 |
| | Exons_HGMD_Mendelian_gene | 36,090,180 | 63,709 | 48,011,279 | 98,805 | 3,871,482 | 12,113 | 4,684,379 | 14,795 |
| | Regulome1_HGMD_Mendelian_gene | 802,747 | 4,700 | 48,116,355 | 99,290 | 17,080 | 133 | 4,685,899 | 14,902 |
| | Exons_HLAclass1 | 8,432 | 9 | 48,116,355 | 99,290 | 3,128 | 3 | 4,685,899 | 14,802 |
| | Regulome1_HLAclass1 | 2,995 | 10 | 48,116,355 | 99,290 | 0 | 0 | 4,685,899 | 14,802 |
| | Exons_HLAclass2 | 38,082 | 65 | 48,130,838 | 99,292 | 1,017 | 6 | 4,686,134 | 14,804 |
| | Regulome1_HLAclass2 | 913 | 5 | 48,130,855 | 99,292 | 0 | 0 | 4,686,134 | 14,804 |

TABLE 11-continued

Exemplary list of content in the HGCP subset

| | | includes 50 bp dilation | | | | | | |
|---|---|---|---|---|---|---|---|---|
| | HGCPmerge100_120924LG.bed | by Set | | Cumulative | | HGCP by Set | | HGCP Cumulative | |
| Priority | Content Name | Bases | Ranges | Bases | Ranges | Bases | Ranges | Bases | Ranges |
| | CFTR_Intronic | 903 | 3 | 48,131,608 | 99,294 | 0 | 0 | 4,686,134 | 14,804 |
| | Triallelic_in_Footprint | 23,509 | 128 | 48,154,196 | 99,400 | 632 | 4 | 4,686,366 | 14,806 |
| | phastConsElements46way-top0.5percent | 3,417,667 | 6,728 | 50,091,253 | 102,331 | 162,245 | 531 | 4,721,759 | 14,903 |

Repetitive elements in the genome and other genomic regions outside of the exome can be difficult to sequence, align and/or assemble, particularly with short read technology (e.g., 2×100 on Illumina HiSeq). Many of these regions in the exome are skipped or perform poorly with standard with standard enrichment strategies. Genomic regions outside the exome (such as introns of HLA) are typically not targeted by exome sequencing. The difficulties in sequencing may be due to poor enrichment efficiency, degenerate mapping of reads and inadequate read length to span common simple tandem repeats or biomedically relevant expanding repeats. These problems are addressed by developing a specific enrichment pulldown (LRP) and protocol to extract primarily these regions for more expensive long paired read sequencing (e.g., 2×250 bp on Illumina MiSeq) or long single read sequencing (e.g., 5 kb single molecule sequencing on PacBio RS or future technologies as available). This longer read sequencing technology is currently 10-fold to several 100-fold more expensive per base than bulk sequencing and is often not currently commercially viable for the entire content regions. Furthermore, in some cases (e.g., PacBio RS), the raw error profile is problematic for general use in SNV calling. However, for some types of important problems, these technologies are required to obtain accurate or clinical quality results that correctly map degenerate sequence or span a repeat sequence. A protocol has been developed in which all such regions are separated into a subset and are sequenced in parallel to achieve a useful economy of scale for the preparation, yet still limit the total amount of sequencing to a practical amount. In addition to sequencing these regions with a different technology, the alignment and other bioinformatic pipeline elements are customized to best leverage these longer reads to improve coverage, accuracy, and characterization (e.g., allelotyping STRs and unstable expanding repeat regions). Phasing and/or haplotyping of HLA and blood typing genes is more tractable using longer reads and longer molecules provided in this library. Reassembly of ambiguous regions is more tractable using the longer molecules and reads from these libraries. An example composition of such a library is listed in Table 12. In addition, the intersection of this library with particular classes of structural problems or genomic content is shown in the final block.

TABLE 12

| | | Includes 100 bp dilation | | | |
|---|---|---|---|---|---|
| | LRPmerge300_120924LG.bed | by Set | | Cumulative | |
| Priority | | Bases | Ranges | Bases | Ranges |
| | Content Name | | | | |
| | MendelDB_snp_0913_2012.bed | 300,380 | 823 | 300,380 | 823 |
| | PharmGKB_snp_0914_2012.bed | 71,926 | 258 | 372,876 | 1,076 |
| | medical_dbSNP_regulome1_Suspect.bed | 107,508 | 371 | 474,890 | 1,433 |
| | GeneReview_snp_0913_2012.bed | 239,363 | 690 | 542,080 | 1,635 |
| | HGMD_ClinVar_snp_0913_2012.bed | 3,074,892 | 7,774 | 3,241,005 | 8,261 |
| | Clinical_Channel_snp_0913_2012.bed | 2,537,774 | 6,684 | 3,880,310 | 9,829 |
| | OMIM_snp_0914_2012.bed | 1,811,109 | 5,019 | 3,880,310 | 9,829 |
| | Varimed_multi_ethnic_snp_0914_2012.bed | 484,477 | 1,439 | 4,295,467 | 10,934 |
| | Varimed_highconf_snp_0914_2012.bed | 6,365,502 | 16,815 | 9,980,716 | 25,215 |
| | HGMD_mut.bed | 7,400,636 | 15,605 | 14,095,445 | 32,199 |
| | Exons_VIP-Genes-120713 | 187,447 | 472 | 14,341,711 | 32,377 |
| | Regulome1_VIP-Genes-120713 | 15,830 | 41 | 14,353,492 | 32,387 |
| | Exons_MendelDB-Genes-120916 | 23,887,624 | 26,913 | 32,552,166 | 47,917 |
| | Regulome1_MendelDB-Genes-120916 | 774,991 | 2,347 | 33,211,287 | 48,852 |
| | Exons_HGMD-Genes-120913 | 44,321,062 | 49,866 | 53,983,227 | 69,498 |
| | Regulome1_HGMD-Genes-120913 | 1,355,456 | 4,013 | 54,494,848 | 70,283 |
| | Exons_CancerGeneCensus.gene | 6,121,488 | 6,826 | 57,070,263 | 72,967 |
| | Regulome1_CancerGeneCensus_gene | 173,742 | 520 | 57,133,995 | 73,058 |
| | Exons_OMIM_Mendelian_gene | 32,224,942 | 36,331 | 59,444,387 | 75,405 |
| | Regulome1_OMIM_Mendelian_gene | 1,129,215 | 3,368 | 59,571,025 | 75,634 |
| | Exons_HGMD_Mendelian_gene | 46,253,280 | 52,403 | 63,975,577 | 80,407 |
| | Regulome1_HGMD_Mendelian_gene | 1,416,254 | 4,273 | 64,173,958 | 80,756 |
| | Exons_HLAclass1 | 10,894 | 3 | 64,173,958 | 80,756 |
| | Regulome1_HLAclass1 | 5,912 | 6 | 64,173,958 | 80,756 |
| | Exons_HLAclass2 | 50,951 | 42 | 64,188,111 | 80,758 |
| | Regulome1_HLAclass2 | 2,196 | 3 | 64,188,111 | 80,758 |
| | CFTR_Intronic | 1,203 | 3 | 64,189,624 | 80,759 |

TABLE 12-continued

| | | | | |
|---|---:|---:|---:|---:|
| Triallelic_in_Footprint | 39,060 | 117 | 64,232,417 | 80,836 |
| phastConsElements46way-top0.5percent | 4,269,414 | 6,189 | 66,642,340 | 83,243 |
| HLA-ClassI | 22,744 | 3 | 66,651,185 | 83,238 |
| HLA-ClassII | 140,811 | 10 | 66,728,362 | 83,207 |
| Blood typingf10k | 206,568 | 3 | 66,902,785 | 83,169 |
| AmylaseRegion | 300,200 | 1 | 67,200,752 | 83,169 |
| ImportantCompression | 192,112 | 3 | 67,379,340 | 83,156 |
| SMN1_SMN2 | 57,657 | 2 | 67,428,632 | 83,146 |
| Problem Name | | | | |
| v3NoCoverage | 51,511,046 | 26,632 | 51,506,246 | 26,608 |
| ShortPEReadMappability | 131,941,961 | 31,071 | 135,610,684 | 40,898 |
| SingleReadMappability | 239,094,172 | 149,523 | 241,428,271 | 156,194 |
| ValidatedCompressions | 3,262,543 | 36 | 244,073,867 | 155,934 |
| SegmentalDuplications | 162,351,720 | 5,902 | 287,784,823 | 145,772 |
| STR > 50 bp | 128,885,115 | 201,050 | 395,004,522 | 297,226 |
| GRCh37patches | 61,247,019 | 134 | 433,409,533 | 292,018 |
| v3LowCoverage | 746,244,957 | 688,267 | 966,704,005 | 689,651 |
| HLA-ClassI | 22,744 | 3 | 966,704,005 | 689,651 |
| HLA-ClassII | 140,811 | 10 | 966,704,005 | 689,651 |
| BloodTypingf10k | 206,568 | 3 | 966,723,788 | 689,642 |
| AmylaseRegion | 300,200 | 1 | 966,815,712 | 689,618 |
| ImportantCompression | 192,112 | 3 | 966,817,041 | 689,617 |
| SMN1_SMN2 | 57,657 | 2 | 966,817,041 | 689,617 |

| | Includes 100 bp dilation | | | |
|---|---:|---:|---:|---:|
| LRPmerge300_120924LG.bed | LRP by Set | | LRP Cumulative | |
| Priority | Bases | Ranges | Bases | Ranges |
| Content Name | | | | |
| MendelDB_snp_0913_2012.bed | 83,107 | 238 | 83,107 | 238 |
| PharmGKB_snp_0914_2012.bed | 17,087 | 65 | 100,722 | 302 |
| medical_dbSNP_regulome1_Suspect.bed | 77,284 | 267 | 173,712 | 560 |
| GeneReview_snp_0913_2012.bed | 77,372 | 210 | 194,354 | 624 |
| HGMD_ClinVar_snp_0913_2012.bed | 945,906 | 2,543 | 1,022,992 | 2,782 |
| Clinical_Channel_snp_0913_2012.bed | 723,269 | 2,045 | 1,162,383 | 3,154 |
| OMIM_snp_0914_2012.bed | 554,960 | 1,605 | 1,162,383 | 3,154 |
| Varimed_multi_ethnic_snp_0914_2012.bed | 153,156 | 419 | 1,299,826 | 3,485 |
| Varimed_highconf_snp_0914_2012.bed | 1,574,979 | 3,476 | 2,671,355 | 6,283 |
| HGMD_mut.bed | 2,199,289 | 4,999 | 3,861,157 | 8,525 |
| Exons_VIP-Genes-120713 | 147,078 | 194 | 3,958,330 | 8,621 |
| Regulome1_VIP-Genes-120713 | 5,972 | 14 | 3,962,756 | 8,624 |
| Exons_MendelDB-Genes-120916 | 7,780,357 | 11,130 | 10,049,097 | 16,057 |
| Regulome1_MendelDB-Genes-120916 | 150,309 | 470 | 10,133,001 | 16,215 |
| Exons_HGMD-Genes-120913 | 14,883,355 | 21,110 | 17,258,590 | 25,544 |
| Regulome1_HGMD-Genes-120913 | 266,188 | 794 | 17,324,858 | 25,670 |
| Exons_CancerGeneCensus.gene | 2,045,184 | 2,809 | 18,218,353 | 26,867 |
| Regulome1_CancerGeneCensus_gene | 27,135 | 94 | 18,229,400 | 26,886 |
| Exons_OMIM_Mendelian_gene | 10,505,055 | 15,008 | 18,976,117 | 27,934 |
| Regulome1_OMIM_Mendelian_gene | 191,633 | 620 | 18,989,192 | 29,963 |
| Exons_HGMD_Mendelian_gene | 15,161,059 | 21,685 | 20,193,619 | 29,734 |
| Regulome1_HGMD_Mendelian_gene | 248,193 | 810 | 20,221,296 | 29,790 |
| Exons_HLAclass1 | 10,894 | 3 | 20,221,296 | 29,790 |
| Regulome1_HLAclass1 | 5,912 | 6 | 20,221,296 | 29,790 |
| Exons_HLAclass2 | 50,951 | 42 | 20,235,449 | 29,792 |
| Regulome1_HLAclass2 | 2,196 | 8 | 20,235,449 | 29,792 |
| CFTR_Intronic | 0 | 0 | 20,235,449 | 29,792 |
| Triallelic_in_Footprint | 36,957 | 109 | 20,276,075 | 29,864 |
| phastConsElements46way-top0.5percent | 1,011,328 | 1,857 | 20,709,245 | 30,497 |
| HLA-ClassI | 22,744 | 3 | 20,718,090 | 30,492 |
| HLA-ClassII | 140,811 | 10 | 20,795,267 | 30,461 |
| Blood typingf10k | 206,588 | 3 | 20,972,246 | 30,428 |
| AmylaseRegion | 300,200 | 1 | 21,271,226 | 30,427 |
| ImportantCompression | 192,117 | 3 | 21,449,546 | 30,416 |
| SMN1_SMN2 | 57.657 | 2 | 21,498,838 | 30,406 |
| Problem Name | | | | |
| vBNoCoverage | 756,946 | 947 | 756,946 | 947 |
| ShortPEReadMappability | 1,415,767 | 1,581 | 1,445,847 | 1,660 |
| SingleReadMappability | 2,364,928 | 3,258 | 2,382,194 | 3,311 |
| ValidatedCompressions | 54,267 | 71 | 2,427,518 | 3,363 |
| SegmentalDuplications | 4,084,205 | 4,129 | 4,393,421 | 4,945 |
| STR-50bp | 1,209,546 | 2,883 | 5,359,052 | 7,494 |
| GRCh37patches | 3,302,971 | 3,265 | 7,821,274 | 9,930 |
| yellowCoverage | 15,671,569 | 25,812 | 20,709,245 | 30,497 |
| HLA-ClassI | 22,744 | 3 | 20,718,090 | 30,492 |

TABLE 12-continued

| | | | | |
|---|---|---|---|---|
| HLA-ClassII | 140,811 | 10 | 20,795,267 | 30,461 |
| BloodTypingf10k | 206,568 | 3 | 20,972,246 | 30,428 |
| AmylaseRegion | 300,200 | 1 | 21,271,226 | 30,427 |
| ImportantCompression | 192,112 | 3 | 21,449,546 | 30,416 |
| SMN1_SMN2 | 57,657 | 2 | 21,498,838 | 30,406 |

All three of these libraries have preliminary data combining standard TruSeq Exome and ESP to produce libraries which are called Exome+, Extended Exome, and ACE (Accuracy and Content Enhanced) Exome (Tables 13-14). These libraries significantly improve coverage of the RefSeq exons, our customized Exome, as well as dramatically improve the coverage of customized Variants (as many of these are outside the exome).

TABLE 13

| | Product Category<br>Product Type | Set Size | | Whole Genome<br>Full Flowcell (PL 2.0)<br>Personalis<br>92× | | Whole Exome<br>TruSeqExome (PL 2.0) B<br>Personalis<br>54× | |
|---|---|---|---|---|---|---|---|
| | ~Price Point | Size | Unit | A | B | A | B |
| Bronze<br>Genome | NEMAR corrections<br>NEMAR.DegappedGenome | 1,102 | kbp | 765,476 | 64,324 | 25,409 | 3,170 |
| | NEMAR.RefSeqExons | 17,999 | kbp | 12,488 | 1,059 | 10,436 | 1,045 |
| | NEMAR.RefSeqCodingExons | 86,692 | kbp | 4,713 | 383 | 4,460 | 419 |
| | NEMAR.RefSeqUTR | 11,307 | kbp | 7,775 | 676 | 5,976 | 526 |
| | NEMAR.PersonalisExome | 7,394 | kbp | 5,029 | 435 | 4,356 | 446 |
| | NEMAR.PersonalisVariants | 4,050 | kbp | 2,171 | 360 | 376 | 72 |
| | NEMAR.PersonalisNetContent<br>Reference | 11,080 | kbp | 7,005 | 769 | 4,547 | 489 |
| | DegappedGenome | 2,861 | Mbp | 98.7% | 51 | 3.7% | 50 |
| | RefSeqExome | 70,467 | kbp | 98.7% | 52 | 77.9% | 49 |
| | RefSeqCodingExons | 33,365 | kbp | 99.0% | 53 | 85.4% | 49 |
| | RefSeqUTR | 37,101 | kbp | 98.4% | 52 | 69.1% | 50 |
| | PersonalisExome | 29,056 | kbp | 98.2% | 53 | 81.3% | 49 |
| | PersonalisVariants | 172 | kbp | 99.8% | 49 | 83.0% | 49 |
| | PersonalisNetContent | 29,095 | kbp | 99.3% | 53 | 80.0% | 49 |
| | Content.RefSeqFirstCodingExons | 2,389 | kbp | 99.1% | 53 | 74.0% | 47 |
| | Content.GCgf70 | 1,639 | kbp | 99.0% | 53 | 38.2% | 48 |
| | Content.NoMapPE0 | 903 | kbp | 71.0% | 46 | 54.0% | 38 |
| | Content.Segmental_Duplications | 2,046 | kbp | 89.1% | 43 | 71.9% | 38 |
| | Content.HomopolymerFlank | 136 | kbp | 97.2% | 44 | 57.7% | 41 |
| | Content.STRgf50f50<br>SNPs | 453 | kbp | 94.0% | 42 | 66.8% | 34 |
| | DegappedGenome | 2,861 | Mbp | 95.3% | 0.34% | 1.9% | 1.65% |
| | RefSeqExons | 70,467 | kbp | 95.8% | 0.21% | 61.9% | 1.60% |
| | RefSeqCodingExons | 33,386 | kbp | 95.0% | 0.19% | 69.7% | 1.61% |
| | RefSeqUTR | 37,101 | kbp | 96.3% | 0.22% | 57.2% | 1.60% |
| | PersonalisExome | 29,056 | kbp | 95.6% | 0.21% | 64.0% | 1.50% |
| | PersonalisVariants | 172 | kbp | 99.8% | 0.02% | 12.6% | 0.31% |
| | PersonalisNetContent | 29,095 | kbp | 97.0% | 0.14% | 44.1% | 1.44% |
| | Content.RefSeqFirstCodingExons | 2,389 | kbp | 92.8% | 0.10% | 60.5% | 1.17% |
| | Content.GCgf70 | 1,639 | kbp | 91.2% | 0.11% | 24.3% | 1.21% |
| | Content.NoMapPE0 | 903 | kbp | 65.4% | 1.06% | 46.3% | 10.98% |
| | Content.Segmental_Duplications | 2,046 | kbp | 83.6% | 0.97% | 56.2% | 7.00% |
| | Content.HomopolymerFlank | 136 | kbp | 81.8% | 1.28% | 23.1% | 13.64% |
| | Content.STRgf50f50 | 453 | kbp | 78.6% | 1.29% | 59.1% | 9.90% |

| | Product Category<br>Product Type | | | Whole Exome<br>Extended Exome<br>(E+, ESP)<br>(Alpha demo<br>in P1) A<br>Personalis<br>56× | | Description of<br>comparison metrics | |
|---|---|---|---|---|---|---|---|
| | ~Price Point | | | A | B | A | B |
| Bronze<br>Genome | NEMAR corrections<br>NEMAR DegappedGenome | | | 31,894 | 3,522 | Homozygous major<br>allele "variants" | Homozygous minor<br>allele variants |
| | NEMAR RefSeqExons | | | 11,224 | 1,046 | removed | called |
| | NEMAR RefSeqCodingExons | | | 4,573 | 393 | | |
| | NEMAR RefSeqUTR | | | 6,551 | 653 | | |
| | NEMAR PersonalisExome | | | 4,915 | 468 | | |
| | NEMAR PersonalisVariants | | | 1,851 | 371 | | |
| | NEMAR PersonalisNetContent | | | 6,573 | 812 | | |

TABLE 13-continued

| Reference | | | | |
|---|---|---|---|---|
| DegappedGenome | 5.1% | 49 | Coverage % | Error: |
| RefSeqExome | 88.1% | 48 | of target | −10log 10(#Errors/ |
| RefSeqCodingExons | 94.7% | 48 | reported | SetSize) |
| RefSeqUTR | 80.3% | 48 | (GC > 50, | (1-Specificity) |
| PersonalisExome | 94.2% | 48 | not LowQual) | (GQ > 50, |
| PersonalisVariants | 96.0% | 47 | | not LowQual) |
| PersonalisNetContent | 93.9% | 48 | | |
| Content.RefSeqFirstCodingExons | 89.0% | 48 | | |
| Content.GCgf70 | 65.6% | 47 | | |
| Content.NoMapPE0 | 61.1% | 36 | | |
| Content.Segmental_Duplications | 77.5% | 37 | | |
| Content.HomopolymerFlank | 77.3% | 37 | | |
| Content.STRgf50f50 | 77.2% | 33 | | |
| SNPs | | | | |
| DegappedGenome | 3.0% | 1.26% | Coverage: % of | Error: |
| RefSeqExons | 78.5% | 1.46% | target reported | % Discordance/ |
| RefSeqCodingExons | 85.4% | 1.50% | (GQ > 50, | VariantLoci |
| RefSeqUTR | 71.3% | 1.44% | not LowQual) | (1-Sensitivity) |
| PersonalisExome | 83.3% | 1.30% | | (GO > 50, |
| PersonalisVariants | 72.7% | 0.10% | | not LowQual) |
| PersonalisNetContent | 79.1% | 0.93% | | |
| Content.RefSeqFirstCodingExons | 76.5% | 0.74% | | |
| Content.GCgf70 | 47.9% | 0.82% | | |
| Content.NoMapPE0 | 58.1% | 0.72% | | |
| Content.Segmental_Duplications | 65.0% | 7.01% | | |
| Content.HomopolymerFlank | 50.3% | 7.84% | | |
| Content.STRgf50f50 | 68.1% | 9.94% | | |

TABLE 14

| Genomic Region | Library | Reference Loci | | Variant Loci | | All Loci | | Region Definition |
|---|---|---|---|---|---|---|---|---|
| | | HQ Cov | Phred Error | HQ Cov | Error % | HQ Cov | Phred Error | |
| RefSeq | TruSeq | 79.6% | 49 | 64.0% | 1.55% | 78.6% | 46 | All exons and UTRs |
| | Exome+ | 88.1% | 48 | 76.6% | 1.46% | 87.3% | 46 | |
| Interpretable Exome | TruSeq | 83.2% | 49 | 65.8% | 1.43% | 82.3% | 47 | 46 PharmGKB VIP genes |
| | Exome+ | 94.2% | 48 | 83.3% | 1.30% | 93.6% | 46 | 1,803 MendelDB genes |
| | | | | | | | | 3,502 HGMD genes |
| | | | | | | | | 488 Cancer genes |
| | | | | | | | | 2,896 OMIM Mendelian genes |
| | | | | | | | | 3,493 HGMD Mendelian genes |
| | | | | | | | | (90-95% of symbols covered in ESP v1) |
| Interpretable Variants | TruSeq | 85.2% | 46 | 13.3% | 0.24% | 78.6% | 43 | MendelDB SNP |
| | Exome+ | 96.0% | 47 | 72.7% | 0.10% | 93.9% | 41 | PharmGKB SNP |
| | | | | | | | | Medical dbSNP Regulome1 suspect |
| | | | | | | | | GeneReview SNP |
| | | | | | | | | HGMD Clinvar SNP |
| | | | | | | | | Clinical Channel SNP |
| | | | | | | | | OMIM SNP |
| | | | | | | | | Varimed Multiethnic SNP |
| | | | | | | | | Varimed High Confidence SNP |

Example 11

Detection of Genome-wide Copy Number Variations with Single Reads Whole Genome Sequencing Data A nucleic acid sample is obtained from a subject and further analyzed by whole genome sequencing to identify the copy number variations in the genome. Single run whole genome sequencing is conducted on the nucleic acid sample 43 times, resulting in 43 single runs of whole genome sequencing data. The single run whole genome sequencing covers 3 gigabasepairs. Paired 100 bp molecules are used. Each of the single run whole genome sequencing data is analyzed using a Hidden Markov Model to detect copy number variations. Genomic bins of 1 kbp, 5 kbp, 10 kbp, and 20 kbp are used for measurement of the number of sequence reads per bin.

Figure 3:
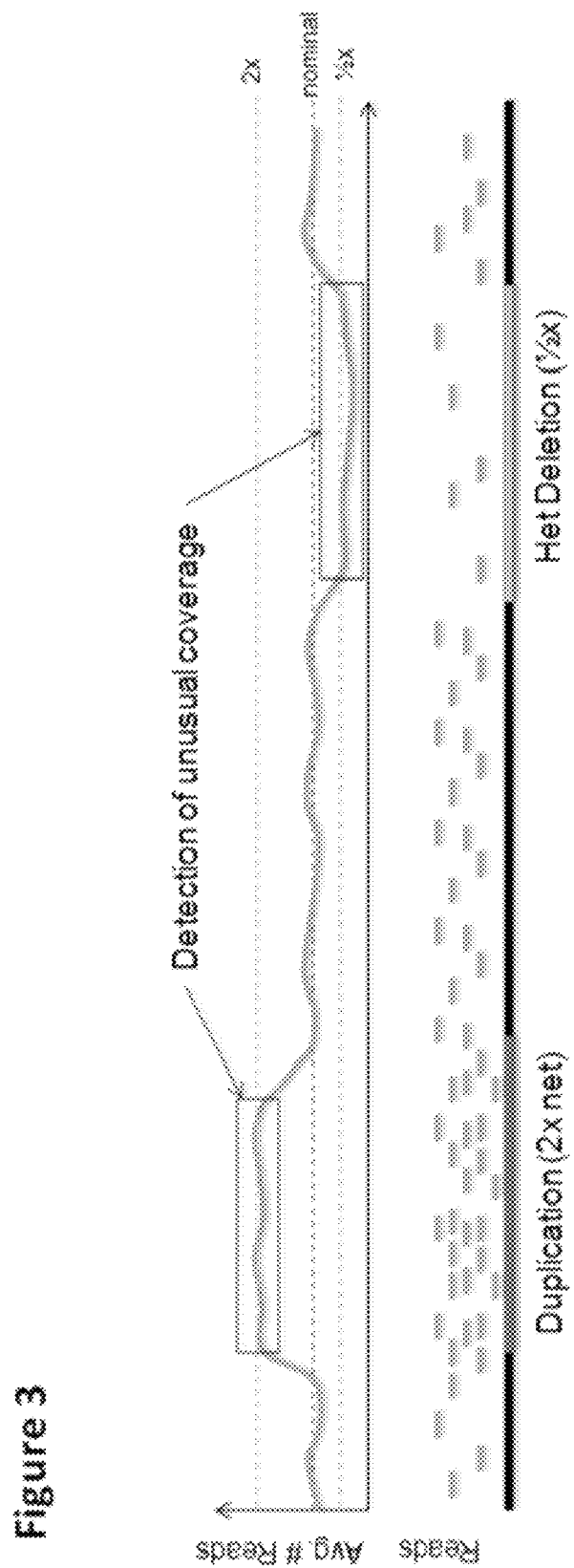
FIG. 3 illustrates a statistical model on sensitivity vs. coverage of genomic regions with single run whole genome sequencing data.
Figure 4:
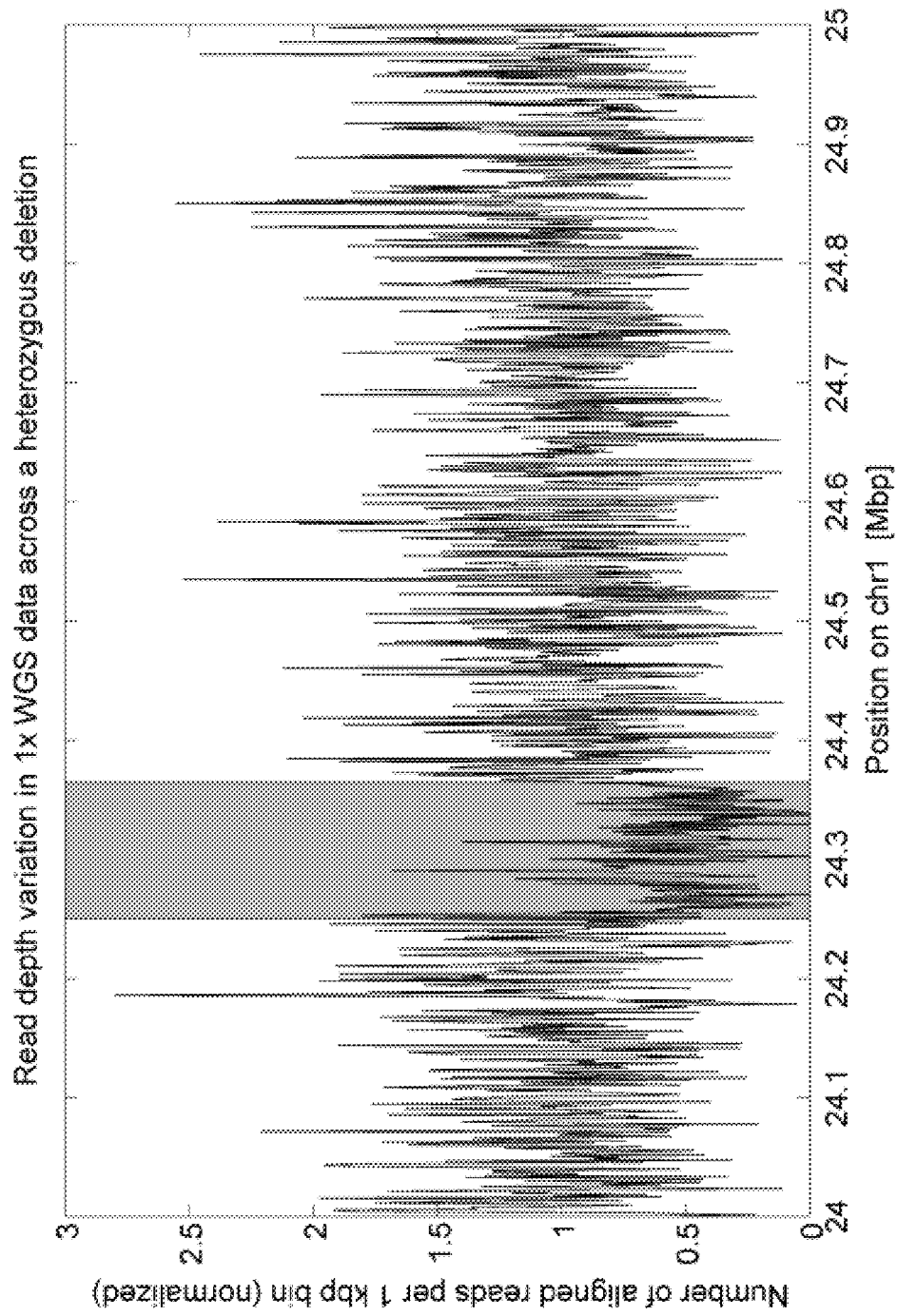
FIG. 4 illustrates a successful detection of a heterozygous deletion in a single run whole genome sequencing data using the Hidden Markov Model.

A single run whole genome sequencing data with paired 100 bp molecules produces an average of n=250 molecules in a given 50 kb region. This quantity is nominally a Poisson random variate (neglecting non-fundamental noise sources). The SNR of a heterozygous deletion is roughly 10~sqrt(n/2) in this example. As shown in FIG. 3, duplications and other copy number increases are found to have a higher SNR. As shown in FIG. 4, successful detection of a heterozygous deletion in the single runs whole genome sequencing data is achieved.

As shown in FIG. 5, the sensitivity to small copy number variations increases as the size of genomic bin gets smaller.

However, the false positive detection of copy number variations decreases as the size of the genomic bins increases.

Example 12

Detection of Systematic Read-depth Variation with Single Reads Whole Genome Sequencing Data Other factors can lead to systematic read-depth variation, besides the presence of copy number variations. Many of these factors tend to be systematic across samples.

Figure 6:
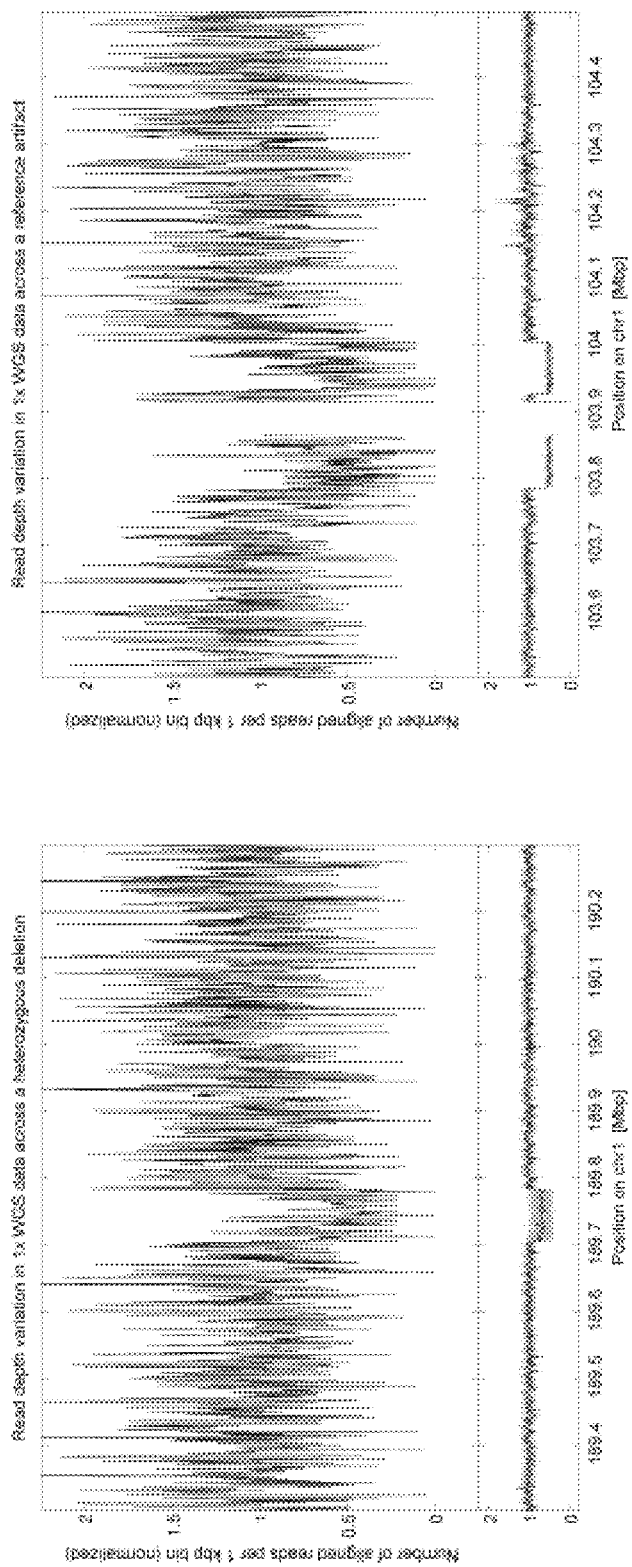
FIG. 6 illustrates other factors that can lead to systematic read-depth variation, besides the presence of copy number variations.

Single run whole genome sequencing data is obtained for a plurality of samples and analyzed using a Hidden Markov Model. The signal read-depth of each read is averaged across 5 samples or more than 5 samples. Many of the factors can be systematic across samples. As shown in FIG. 6, by accumulating a database of the average read depth across many samples, as well as the variance across samples, these systematic regions are identified and filtered out, which would otherwise correspond to false positive CNV detections, in a naïve application of the Hidden Markov Model method.

Example 13

Whole Exome Sequencing Supplemented with Single Reads Whole Genome Sequencing Data Whole exome sequencing is conducted and analyzed using methods described in earlier Examples. Low coverage whole genome sequencing is used as a supplement to targeted exome sequencing. The low coverage genome data covers 1-10 gigabasepairs and is analyzed for coverage in genomic bins of 100-1,000,000 basepairs to assess CNV of the sequence in the sample. A single run low coverage whole genome sequencing data covering 3 gigabasepairs adds $100-$200 to the exome sequencing costs and delivers genome-wide SV sensitivity from <50 kb upwards. In addition, variants detected in the low coverage whole genome data can be used to identify known haplotype blocks and impute variants over the whole genome with or without exome data.

Example 14

Detection of Genome-wide Copy Number Variations with Off-Target Whole Exome Sequencing Data Whole exome sequencing is conducted, enriched and analyzed using methods described in earlier Examples. The exonic and non-exonic sequence data of the whole exome sequencing data is annotated. It is observed that about 10% or more of the whole exome sequencing data comprises non-exonic data or off-target reads. Furthermore, it is observed that these non-exonic data are spread fairly uniformly across the entire genome.

Non-exonic data is analyzed using a Hidden Markov Model. Certain regions that are affected by enrichment are excluded from the analysis. Copy number variations and structural variants are detected using the remaining set of reads distributed over the entire genome.

Example 15

Detection of Genome-wide Copy Number Variations with Off-target Whole Exome Sequencing Data and a Low Coverage Whole Genome Sequencing Data Whole exome sequencing is conducted using a nucleic acid sample. Data is enriched and analyzed using methods described in earlier Examples. A 0.5 read of whole genome sequencing is conducted on the same nucleic acid sample. The exonic and non-exonic sequence data of the whole exome sequencing data is annotated. Non-exonic data and the 0.5 read whole genome sequencing data are combined and analyzed using a Hidden Markov Model. Certain regions that are affected by enrichment are excluded from the analysis. Copy number variations and structural variants are detected over the entire genome.

As used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

Methods and systems of the present disclosure can be combined with and/or modified by other methods and systems, such as those described in U.S. Patent Publication No. 2014/0200147 ("Methods and Systems for Genetic Analysis"), which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for genetic analysis of a biological sample of a subject, comprising:
   (a) sequencing a first nucleic acid sample from said biological sample of said subject to generate untargeted sequencing data, wherein said untargeted sequencing data comprises less than about 90 gigabases;
   (b) sequencing a second nucleic acid sample from said biological sample of said subject to generate target-specific sequencing data;

(c) combining, with the aid of a computer processor, said untargeted sequencing data and said target-specific sequencing data to produce a combined data set; and (d) generating, with the aid of a computer processor, an output from at least a portion of said combined data set, wherein said output is indicative of a presence or absence of one or more polymorphisms in a genome of said subject or a portion of said genome.

2. The method of claim 1, wherein said generating in (d) comprises (1) mapping said untargeted sequencing data onto a first reference sequence to generate a first alignment, and (2) mapping said target-specific sequencing data onto a second reference sequence to generate a second alignment.

3. The method of claim 2, wherein said first reference sequence and said second reference sequence are the same sequence.

4. The method of claim 2, further comprising (i) combining said first alignment and said second alignment to yield a combined sequence, and (ii) mapping said combined sequence onto a reference sequence.

5. The method of claim 1, wherein said target-specific sequencing data is based on targeted sequencing of an exome, specific genes, genomic regions, or a combination thereof.

6. The method of claim 1, wherein said untargeted sequencing data is generated using one or more random primers or hybridization probes, and wherein said target-specific sequencing data is generated using one or more non-random primers or hybridization probes.

7. The method of claim 6, wherein said non-random primers comprise primers targeting one or more genes, exons, untranslated regions, or a combination thereof.

8. The method of claim 1, wherein said untargeted sequencing data is whole genome sequencing data.

9. The method of claim 8, wherein said whole genome sequencing data comprises single reads, paired-end reads, or mate-pair reads.

10. The method of claim 1, wherein said target-specific sequencing data comprises a specific portion and a non-specific portion, and wherein at least a portion of said untargeted sequencing data is included in said non-specific portion of said target-specific sequencing data.

11. The method of claim 10, wherein said untargeted sequencing data is included in said non-specific portion of said target-specific sequencing data.

12. The method of claim 1, wherein each of said untargeted sequencing data and said target-specific sequencing data comprises variant data, and wherein said combining comprises combining variant data from said untargeted sequencing data and variant data from said target-specific sequencing data into said combined data set.

13. The method of claim 12, wherein said untargeted sequencing data comprises copy number or structural variant data, and wherein said target-specific sequencing data comprises single nucleotide variations (SNV) or insertion deletion polymorphism (indel) data.

14. The method of claim 1, wherein said untargeted sequencing data comprises up to about 10 gigabases.

15. The method of claim 1, wherein said first nucleic acid sample and said second nucleic acid sample are separately subjected to untargeted sequencing and target-specific sequencing, respectively.

16. The method of claim 1, wherein said combining comprises removing any redundant sequences.

17. The method of claim 1, wherein generating said output comprises using a computer processor to identify said one or more polymorphisms at a sensitivity greater than or equal to 90%, wherein said one or more polymorphisms include structural variants that are less than 100,000 bases in length.

18. The method of claim 1, wherein said target-specific sequencing data comprises sequencing data corresponding to less than or equal to about 180,000 exons in an exome of said subject.

19. The method of claim 1, wherein said biological sample is a blood sample or a tissue biopsy.

20. The method of claim 1, wherein said sequencing of (a) and/or (b) is massively parallel sequencing.

21. The method of claim 1, wherein said untargeted sequencing data of (a) and said target-specific sequencing data of (b) comprise sequencing reads, and wherein said combining of (c) comprises combining said sequencing reads.

22. The method of claim 1, wherein said untargeted sequencing data comprises up to about 50 gigabases.

23. The method of claim 1, wherein said untargeted sequencing data is at least about 100 megabases.

24. A system for genetic analysis of a biological sample of a subject, comprising:
at least one computer memory comprising untargeted sequencing data and target-specific sequencing data, wherein said untargeted sequencing data is generated by sequencing a first nucleic acid sample from said biological sample of said subject and said target-specific sequencing data is generated by sequencing a second nucleic acid sample from said biological sample of said subject, wherein said untargeted sequencing data comprises less than about 90 gigabases;
a computer processor coupled to said at least one computer memory and programmed to (i) combine said untargeted sequencing data and said target-specific sequencing data to produce a combined data set, and (ii) generate an output from at least a portion of said combined data set, wherein said output is indicative of a presence or absence of one or more polymorphisms in a genome of said subject or a portion of said genome; and
an electronic data storage unit coupled to said computer processor, wherein said electronic data storage unit comprises said combined data set or said output.

25. The system of claim 24, wherein each of said untargeted sequencing data and said target-specific sequencing data comprises variant data, and wherein said computer processor is programmed to combine variant data from said untargeted sequencing data and variant data from said target-specific sequencing data into said combined data set.

26. The system of claim 25, wherein said untargeted sequencing data comprises copy number or structural variant data, and wherein said target-specific sequencing data comprises single nucleotide variations (SNV) or insertion deletion polymorphism (indel) data.

27. The system of claim 24, further comprising an electronic display coupled to said computer processor, wherein said electronic display provides said output for display.

28. The system of claim 24, wherein said computer processor is programmed to (1) map said untargeted sequencing data onto a first reference sequence in computer memory to generate a first alignment, and (2) map said target-specific sequencing data onto a second reference sequence in computer memory to generate a second alignment.

29. The system of claim 24, wherein said computer processor is programmed to generate said combined data set by (1) combining said untargeted sequencing data and said target-specific sequencing data and (2) removing any redundant sequences.

30. The system of claim 24, wherein said untargeted sequencing data comprises up to about 10 gigabases.

31. The system of claim 24, wherein said target-specific sequencing data comprises sequencing data corresponding to less than or equal to about 180,000 exons in an exome of said subject.

32. The system of claim 24, wherein said computer processor is programmed to generate said output, that is indicative of the presence or absence of said one or more polymorphisms, at a sensitivity greater than or equal to 90%, wherein said one or more polymorphisms include structural variants that are less than 100,000 bases in length.

33. The system of claim 24, wherein said sequencing of a first nucleic acid sample and/or said sequencing of a second nucleic acid sample is massively parallel sequencing.

34. The system of claim 24, wherein said untargeted sequencing data and said target-specific sequencing data comprise sequencing reads, and wherein said combining of said untargeted sequencing data and said target-specific sequencing comprises combining said sequencing reads.

35. The system of claim 24, wherein said untargeted sequencing data comprises up to about 50 gigabases.

36. The system of claim 24, wherein said untargeted sequencing data is at least about 100 megabases.

* * * * *